(12) United States Patent
Moffat et al.

(10) Patent No.: US 8,962,825 B2
(45) Date of Patent: Feb. 24, 2015

(54) HYDROXAMATES AS INHIBITORS OF HISTONE DEACETYLASE

(75) Inventors: David Charles Festus Moffat, Abingdon (GB); Sanjay Ratilal Patel, Abingdon (GB); Francesca Ann Day, Abingdon (GB); Andrew James Belfield, Abingdon (GB); Alistair David Graham Donald, Abingdon (GB); Alan Hornsby Davidson, Abingdon (GB); Alan Hastings Drummond, Abingdon (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 445 days.

(21) Appl. No.: 12/446,267

(22) PCT Filed: Oct. 30, 2006

(86) PCT No.: PCT/GB2006/004034
§ 371 (c)(1),
(2), (4) Date: Nov. 16, 2009

(87) PCT Pub. No.: WO2008/053131
PCT Pub. Date: May 8, 2008

(65) Prior Publication Data
US 2010/0317678 A1 Dec. 16, 2010

(51) Int. Cl.
*C07D 345/00* (2006.01)
*C07D 239/42* (2006.01)

(52) U.S. Cl.
CPC ................................. *C07D 239/42* (2013.01)
USPC ............................................................. 540/1

(58) Field of Classification Search
CPC . A61K 31/455; A61K 31/451; A61K 31/506; C07D 211/26; C07D 239/42
USPC ........................................................... 540/1
See application file for complete search history.

(56) References Cited

U.S. PATENT DOCUMENTS 4,254,220 A 3/1981 Meiattini
5,369,108 A 11/1994 Breslow et al.
(Continued)

FOREIGN PATENT DOCUMENTS

EP 0505321 A2 9/1992
WO 01/18171 A2 3/2001
(Continued)

OTHER PUBLICATIONS

Han, J. 'Advances in Characterization of Pharmaceutical Hydrates' Trends in Bio/Pharmaceutical Industry, vol. 3, p. 25-29, 2006.*

Vippagunta et al 'Crystalline Solids' Advanced Drug Delivery Reviews, vol. 48, p. 3-26, 2001.*
International Search Report Issued Jul. 5, 2007 for PCT/GB2006/004034 (WO 2008/053131 A 1).
Berger, Shelley L., "An embarrassment of niches: the many covalent modifications of histones in transcriptional regulation", Oncogene, 2001, vol. 20, pp. 3007-3013.
(Continued)

*Primary Examiner* — Wu-Cheng Winston Shen
*Assistant Examiner* — Christopher R Stone
(74) *Attorney, Agent, or Firm* — Duke M. Fitch; John Lemanowicz; William R. Majarian

(57) ABSTRACT

Compounds of formula (I), and salts, N-oxides, hydrates and solvates thereof are histone deacetylase inhibitors and are useful in the treatment of cell proliferative diseases, including cancers:

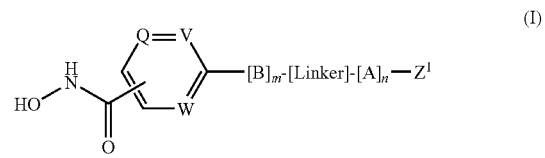

wherein Q, V and W independently represent —N═ or —C═; B is a divalent radical selected from (B1), (B2), (B3), (B4), (B5) and (B6).

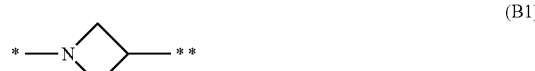

(B1)

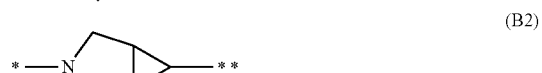

(B2)

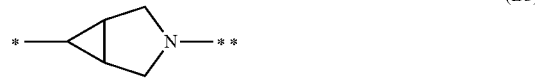

(B3)

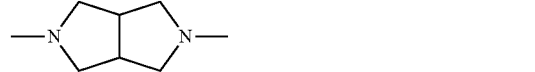

(B4)

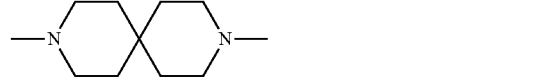

(B5)

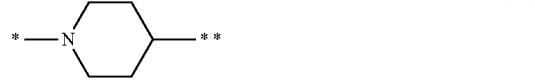

(B6)

wherein the bond marked * is linked to the ring containing Q, V and W through -[Linker1]- and the bond marked ** is linked to A through -[Linker2]-; A is an optionally substituted mono-, bi- or tri-cyclic carbocyclic or heterocyclic ring system; -[Linker1]- and -[Linker2]- independently represent a bond, or a divalent linker radical; and R is (a) a radical of formula $R_1R_2CHNH-Y-L^1-X^1-(CH_2)_z-$ or (b) a radical of formula $R-L^1-Y^1-(CH_2)_z-$.

28 Claims, No Drawings

(56) References Cited

U.S. PATENT DOCUMENTS

| | | | |
|---|---|---|---|
| 7,932,246 | B2 | 4/2011 | Moffat et al. |
| 7,939,666 | B2 | 5/2011 | Davidson et al. |
| 7,973,181 | B2 | 7/2011 | Davidson et al. |
| 8,044,211 | B2 | 10/2011 | Moffat et al. |
| 8,148,531 | B2 | 4/2012 | Davidson et al. |
| 8,211,900 | B2 | 7/2012 | Davidson |
| 8,217,050 | B2 | 7/2012 | Moffat et al. |
| 2004/0072735 | A1 | 4/2004 | Richon et al. |
| 2004/0092558 | A1 | 5/2004 | Klimko et al. |
| 2009/0203711 | A1 | 8/2009 | Moffat |
| 2009/0215800 | A1 | 8/2009 | Davidson et al. |
| 2010/0004250 | A1 | 1/2010 | Philips et al. |
| 2010/0010010 | A1 | 1/2010 | Davidson et al. |
| 2010/0010057 | A1 | 1/2010 | Moffat et al. |
| 2010/0216802 | A1 | 8/2010 | Moffat et al. |
| 2010/0317678 | A1 | 12/2010 | Moffat et al. |
| 2013/0116318 | A1 | 5/2013 | Davidson et al. |
| 2013/0197042 | A1 | 8/2013 | Davidson et al. |

FOREIGN PATENT DOCUMENTS

| | | | |
|---|---|---|---|
| WO | 01/38322 | A1 | 5/2001 |
| WO | 01/70675 | A2 | 9/2001 |
| WO | 0222577 | A2 | 3/2002 |
| WO | 02/26696 | A1 | 4/2002 |
| WO | 02/26703 | A1 | 4/2002 |
| WO | 02/30879 | A2 | 4/2002 |
| WO | 02/069947 | A2 | 9/2002 |
| WO | 03011851 | A2 | 2/2003 |
| WO | 03/066579 | A | 8/2003 |
| WO | 03066579 | A2 | 8/2003 |
| WO | 03/076395 | A | 9/2003 |
| WO | 03075929 | A1 | 9/2003 |
| WO | 03076395 | A1 | 9/2003 |
| WO | 03076400 | A1 | 9/2003 |
| WO | 03076401 | A1 | 9/2003 |
| WO | 03076421 | A1 | 9/2003 |
| WO | 03076422 | A1 | 9/2003 |
| WO | 03076430 | A1 | 9/2003 |
| WO | 03/082288 | A1 | 10/2003 |
| WO | 03087057 | A1 | 10/2003 |
| WO | 03092686 | A1 | 11/2003 |
| WO | 2004/013130 | A1 | 2/2004 |
| WO | 2004043940 | A1 | 5/2004 |
| WO | 2004062601 | A2 | 7/2004 |
| WO | 2004/092115 | A2 | 10/2004 |
| WO | 2004092145 | A1 | 10/2004 |
| WO | 2004/110989 | A1 | 12/2004 |
| WO | 2005/004861 | A1 | 1/2005 |
| WO | 2005/007091 | A2 | 1/2005 |
| WO | 2005/013958 | A1 | 2/2005 |
| WO | 2005/014588 | A1 | 2/2005 |
| WO | 2005/018578 | A2 | 3/2005 |
| WO | 2005/019174 | A1 | 3/2005 |
| WO | 2005/028447 | A1 | 3/2005 |
| WO | 2005/030704 | A1 | 4/2005 |
| WO | 2005/037272 | A1 | 4/2005 |
| WO | 2005/046575 | A2 | 5/2005 |
| WO | 2006117548 | A1 | 11/2006 |
| WO | 2006117549 | A1 | 11/2006 |
| WO | 2006117567 | A2 | 11/2006 |
| WO | 2006123121 | A1 | 11/2006 |
| WO | 2008040934 | A1 | 4/2008 |

OTHER PUBLICATIONS

Grunstein, Michael, "Histone acelyation in chromatin structure and transcription", Nature, Sep. 1997, vol. 389, pp. 349-352.

Wolffe, Alan P., "Histone Deacetylase: A Regulator of Transcription", Science, Apr. 19, 1996, vol. 272, pp. 371-372.

Wade, et al, "Histone acetylation: chromatin in action", Trends Biochem Sci, Apr. 1997, vol. 22, pp. 128-132.

Gray et al., "Histone Acetylation/Deacetylation and Cancer: An "Open" and "Shut" Case?", Current Molecular Medicine, 2001, vol. 1, pp. 401-429.

Kelly et al., "Histone deacetylase inhibitors: from target to clinical trials", Expert Opinion Investig. Drugs, 2002, vol. 11, pp. 1695-1713.

Kramer et al., "Histone deacetylase as a therapeutic target" Trends Endocrinology & Metabolism, Sep. 2001, vol. 12, No. 7, pp. 294-300.

Vigushin et al., "Histone deacetylase inhibitors in cancer treatment", Anticancer Drugs, 2002, vol. 13, pp. 1-13.

Hughes, Robert E., "Polyglutamine Disease: Acetyltransferases Awry", Current Biology, Feb. 19, 2002, vol. 12, pp. R141-R143.

McCampbell et al., "Histone deacetylase inhibitors reduce polyglutamine toxicity", Proc. Soc. Natl. Acad. Sci., Dec. 18, 2001, vol. 98, No. 26, pp. 15179-15184.

Hockly et al., "Suberoylanilide hydroxamic acid, a histone deacetylase inhibitor, ameliorates motor deficits in a mouse model of Huntington's disease", Proc. Soc. Natl. Acad. Sci., Feb. 18, 2003, vol. 100, No. 100, pp. 2041-2046.

Hempen et al., Reduction of Acetylated a-Tubulin Immunoreactivity in Neurofibrillary Tangle-bearing Neurons in Alzheimer's Disease, Journal of Neuropathology and Experimental Neurology, Sep. 1996, vol. 55, No. 9, pp. 964-972.

Skov et al., "Histone deacetylase inhibitors: a new class of immunosuppressors targeting a novel signal pathway essential for CD154 expression", Blood, Feb. 15, 2001, vol. 101, No. 4, pp. 1430-1438.

Mishra et al., "Histone deacetylase inhibitors modulate renal disease in the MRL-1pr/1pr mouse", Journal of Clinical Investigation, Feb. 2003, vol. 111, No. 4, pp. 539-552.

Mosley et al., "Glucose Regulates INsulin Gene Transcription by Hyperacetylation in HIstone H4", The Journal of Biological Chemistry, May 30, 2003, vol. 278, No. 22, pp. 19660-19666.

Darkin-Rattray et al., "Apicidin: A novel antiprotozoal agent that inhibits parasite histone deacetylase", Proc. Soc. Natl. Acad. Sci., Nov. 1996, vol. 93, pp. 13143-13147.

Witt et al., "Induction of fetal hemoglobin expression by the histone deacetylase inhibitor apicidin", Blood, Mar. 1, 2003, vol. 101, No. 5, pp. 2001-2007.

Van Roon et al., "Selective Elimination of Synovial Inflammatory Macrophages in Rheumatoid Arthritis by an Fcg Receptor I-Directed Immunotoxin", Arthritis and Rheumatism, May 2003, vol. 48, No. 5, pp. 1229-1238.

Naldini et al., "Role of Inflammatory Mediators in Angiogenesis", Current Drug Targets—Inflammation & Allergy, 2005, vol. 4, pp. 3-8.

Wittich et al., "Structure—Activity Relationships on Phenylalanine-Containing Inhibitors of Histone Deacetylase: In Vitro Enzyme Inhibition, Induction of Differentiation, and Inhibition of Proliferation of Friend Leukemic Cells", Journal of Medicinal Chemistry, 2002, vol. 45, pp. 3296-3309.

Jung et al., "Analogues of Trichostatin A and Trapoxin B as Histone Deacytelase Inhibitors", Bioorganic & Medicinal Chemistry Letters, 1997, vol. 7, No. 13, pp. 1655-1658.

Dutta et al., "Inhibitors of Human Renin, Cyclic Peptide Analogues Containing a D-Phe-Lys-D-Trp Sequence", Journal of Medicinal Chemistry, 1990, vol. 33, pp. 2560-2568.

Jensen et al., "Backbone Amide Linker (BAL) Strategy for Solid-Phase Synthesis of C-Terminal-Modified and Cyclic Peptides", Journal of the American Chemical Society, 1998, vol. 120, pp. 5441-5452.

Blanchard et al., "Histone deacetylase inhibitors: new drugs for the treatment of inflammatory diseases?", Drug Discovery Today, 2005, vol. 10, No. 3, pp. 197-204.

Van De Waterbeemd et al., "Property-Based Design: Optimization of Drug Absorption and Pharmacokinetics" Journal of Medicinal Chemistry, Apr. 26, 2001, vol. 44, No. 9, pp. 1313-1333.

Cahard et al., "Aryloxy Phosphoramidate Triesters as Pro-Tides", Mini-reviews in Medicinal Chemistry, 2004, vol. 4, No. 4, pp. 371-381.

* cited by examiner

HYDROXAMATES AS INHIBITORS OF HISTONE DEACETYLASE

CROSS REFERENCE TO RELATED APPLICATIONS

This application is a National Stage application of co-pending PCT application PCT/GB2006/004034 filed Oct. 30, 2006. This application is incorporated herein by reference in its entirety.

This invention relates to compounds which inhibit members of the histone deacetylase family of enzymes and to their use in the treatment of cell proliferative diseases, including cancers, polyglutamine diseases, for example Huntingdon disease, neurodegenerative diseases for example Alzheimer disease, autoimmune disease for example rheumatoid arthritis and organ transplant rejection, diabetes, haematological disorders, inflammatory disease, cardiovascular disease, atherosclerosis, and the inflammatory sequelae of infection.

BACKGROUND TO THE INVENTION

In eukaryotic cells DNA is packaged with histones, to form chromatin. Approximately 150 base pairs of DNA are wrapped twice around an octamer of histones (two each of histones 2A, 2B, 3 and 4) to form a nucleosome, the basic unit of chromatin. The ordered structure of chromatin needs to be modified in order to allow transcription of the associated genes. Transcriptional regulation is key to differentiation, proliferation and apoptosis, and is, therefore, tightly controlled. Control of the changes in chromatin structure (and hence of transcription) is mediated by covalent modifications to histones, most notably of the N-terminal tails. Covalent modifications (for example methylation, acetylation, phosphorylation and ubiquitination) of the side chains of amino acids are enzymatically mediated (A review of the covalent modifications of histones and their role in transcriptional regulation can be found in Berger S L 2001 Oncogene 20, 3007-3013; See Grunstein M 1997 Nature 389, 349-352; Wolffe A P 1996 Science 272, 371-372; and Wade P A et al 1997 Trends Biochem Sci 22, 128-132 for reviews of histone acetylation and transcription).

Acetylation of histones is associated with areas of chromatin that are transcriptionally active, whereas nucleosomes with low acetylation levels are, typically, transcriptionally silent. The acetylation status of histones is controlled by two enzyme classes of opposing activities; histone acetyltransferases (HATs) and histone deacetylases (HDACs). In transformed cells it is believed that inappropriate expression of HDACs results in silencing of tumour suppressor genes (For a review of the potential roles of HDACs in tumorigenesis see Gray S G and Teh B T 2001 Curr Mol Med 1, 401-429). Inhibitors of HDAC enzymes have been described in the literature and shown to induce transcriptional reactivation of certain genes resulting in the inhibition of cancer cell proliferation, induction of apoptosis and inhibition of tumour growth in animals (For review see Kelly W K et al 2002 Expert Opin Investig Drugs 11, 1695-1713). Such findings suggest that HDAC inhibitors have therapeutic potential in the treatment of proliferative diseases such as cancer (Kramer O H et al 2001 Trends Endocrinol 12, 294-300, Vigushin D M and Coombes R C 2002 Anticancer Drugs 13, 1-13).

In addition, others have proposed that aberrant HDAC activity or histone acetylation is implicated in the following diseases and disorders; polyglutamine disease, for example Huntingdon disease (Hughes R E 2002 Curr Biol 12, R141-R143; McCampbell A et al 2001 Proc Soc Natl Acad Sci 98, 15179-15184; Hockly E et al 2003 Proc Soc Natl Acad Sci 100, 2041-2046), other neurodegenerative diseases, for example Alzheimer disease (Hempen B and Brion J P 1996, J Neuropathol Exp Neurol 55, 964-972), autoimmune disease and organ transplant rejection (Skov S et al 2003 Blood 101, 14 30-1438; Mishra N et al 2003 J Clin Invest 111, 539-552), diabetes (Mosley A L and Ozcan S 2003 J Biol Chem 278, 19660-19666) and diabetic complications, infection (including protozoal infection (Darkin-Rattray, S J et al 1996 Proc Soc Natl Acad Sci 93, 13143-13147)) and haematological disorders including thalassemia (Witt O et al 2003 Blood 101, 2001-2007). The observations contained in these manuscripts suggest that HDAC inhibition should have therapeutic benefit in these, and other related, diseases Many types of HDAC inhibitor compounds have been suggested, and several such compounds are currently being evaluated clinically, for the treatment of cancers. For example, the following patent publications disclose such compounds:

| | |
|---|---|
| U.S. Pat. No. 5,369,108 and WO 01/18171 | WO 03/076400 |
| U.S. Pat. No. 4,254,220 | WO 03/076401 |
| WO 01/70675 | WO 03/076421 |
| WO 01/38322 | WO 03/076430 |
| WO 02/30879 | WO 03/076422 |
| WO 02/26703 | WO 03/082288 |
| WO 02/069947 | WO 03/087057 |
| WO 02/26696 | WO 03/092686 |
| WO 03/082288 | WO 03/066579 |
| WO 02/22577 | WO 03/011851 |
| WO 03/075929 | WO 04/013130 |
| WO 03/076395 | WO 04/110989 |
| WO 04/092115 | WO 05/007091 |
| WO 04/0224991 | WO 05/030704 |
| WO 05/014588 | WO 05/013958 |
| WO 05/018578 | WO 05/028447 |
| WO 05/019174 | WO 05/02690 |
| WO 05/004861 | |

Many of the HDAC inhibitors known in the art have a structural template, which may be represented as in formula (A):

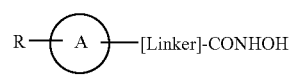

(A)

wherein ring A is a carbocyclic or heterocyclic ring system with optional substituents R, and [Linker] is a linker radical of various types. The hydroxamate group functions as a metal binding group, interacting with the metal ion at the active site of the HDAC enzyme, which lies at the base of a pocket in the folded enzyme structure. The ring or ring system A lies within or at the entrance to the pocket containing the metal ion, with the -[Linker]- radical extending deeper into that pocket linking A to the metal binding hydroxamic acid group. In the art, and occasionally herein, the ring or ring system A is sometimes informally referred to as the "head group" of the inhibitor.

International Patent application No. PCT/GB2006/001779 describes and claims a new class of HDAC inhibitors whose structures fit the generalised template (A). That new class consists of compounds of formula (B) and their salts, N-oxides, hydrates and solvates:

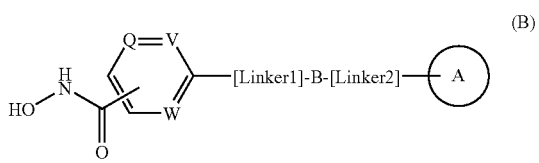

wherein
Q, V and W independently represent —N= or —C=;
B is a divalent radical selected from (B1), (B2), (B3), (B4), and (B5).

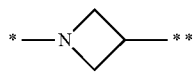

(B1)

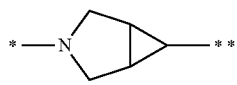

(B2)

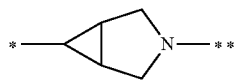

(B3)

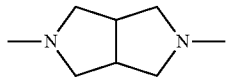

(B4)

(B5)

wherein the bond marked * is linked to the ring containing Q, V and W through -[Linker1]- and the bond marked ** is linked to A through -[Linker2]-; A is an optionally substituted mono-, bi- or tri-cyclic carbocyclic or heterocyclic ring system; and -[Linker1]- and -[Linker2]- independently represent a bond, or a divalent linker radical.

BRIEF DESCRIPTION OF THE INVENTION

This invention is based on the finding that the introduction of an alpha amino acid ester grouping into the HDAC inhibitor molecular template (B) and certain structurally similar templates, facilitates penetration of the agent through the cell membrane, and thereby allows intracellular carboxylesterase activity to hydrolyse the ester to release the parent acid. Being charged, the acid is not readily transported out of the cell, where it therefore accumulates to increase the intracellular concentration of active HDAC inhibitor. This leads to increases in potency and duration of action. The invention therefore makes available a class of compounds which are alpha amino acid conjugates of structures (B) and certain related structures. The alpha amino acid ester moiety is a substrate for intracellular carboxylesterase (also referred to herein as an "esterase motif"). Such conjugates, and the corresponding de-esterified parent acids, have pharmaceutical utility in the treatment of diseases such as cancers which benefit from intracellular inhibition of HDAC.

DETAILED DESCRIPTION OF THE INVENTION

According to the invention there is provided a compound of formula (I), or a salt, N-oxide, hydrate or solvate thereof:

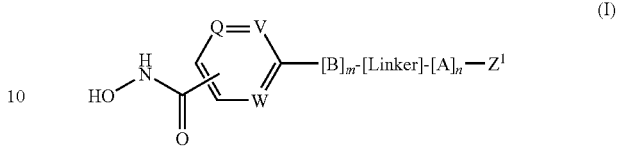

(I)

wherein
m and n are independently 0 or 1, provided that at least one of m and n is 1;
Q, V and W independently represent —N= or —C=;
B is a divalent radical selected from (B1), (B2), (B3), (B4), (B5) and (B6):

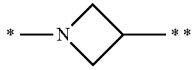

(B1)

(B2)

(B3)

(B4)

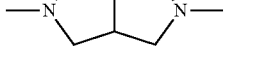

(B5)

(B6)

wherein the bond marked * is linked to the ring containing Q, V and W;
A is an optionally substituted mono-, bi- or tri-cyclic carbocyclic or heterocyclic ring system;
-[Linker]- represents a bond, or a divalent linker radical;
$Z^1$ is (a) a radical of formula $R_1R_2CHNH$—Y-$L^1$-$X^1$—$(CH_2)_z$— or (b) a radical of formula R-$L^1$-$Y^1$—$(CH_2)_z$—, wherein:
R is a radical of formula (X) or (Y)

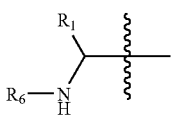

(X)

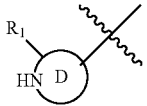

(Y)

$R_1$ is a carboxylic acid group (—COOH), or an ester group which is hydrolysable by one or more intracellular esterase enzymes to a carboxylic acid group;

$R_6$ is hydrogen; or optionally substituted $C_1$-$C_6$ alkyl, $C_3$-$C_7$ cycloalkyl, aryl or heteroaryl or —(C=O)$R_3$, —(C=O)O$R_3$, or —(C=O)N$R_3$ wherein $R_3$ is hydrogen or optionally substituted ($C_1$-$C_6$)alkyl.

$R_2$ is the side chain of a natural or non-natural alpha amino acid;

Y is a bond, —C(=O)—, —S(=O)$_2$—, —C(=O)O—, —C(=O)N$R_3$—, —C(=S)—N$R_3$—, —C(=NH)—N$R_3$ or —S(=O)$_2$N$R_3$— wherein $R_3$ is hydrogen or optionally substituted $C_1$-$C_6$ alkyl;

$Y^1$ is a bond, —(C=O)—, —S(O$_2$)—, —C(=O)O—, —OC(=O)—, —(C=O)N$R_3$—, —N$R_3$(C=O)—, —S(O$_2$)N$R_3$—, —N$R_3$S(O$_2$)—, or —N$R_3$(C=O)N$R_4$—, wherein $R_3$ and $R_4$ are independently hydrogen or optionally substituted ($C_1$-$C_6$)alkyl, $L^1$ is a divalent radical of formula -(Alk$^1$)$_m$(Q)$_n$(Alk$^2$)$_p$— wherein m, n and p are independently 0 or 1, Q is (i) an optionally substituted divalent mono- or bicyclic carbocyclic or heterocyclic radical having 5-13 ring members, or (ii), in the case where p is 0, a divalent radical of formula -Q$^1$-X$^2$— wherein X$^2$ is —O—, —S— or NR$^A$— wherein R$^A$ is hydrogen or optionally substituted $C_1$-$C_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^A$—) link wherein R$^A$ is hydrogen or optionally substituted $C_1$-$C_3$ alkyl;

$X^1$ is a bond, —C(=O)—; or —S(=O)$_2$—; —NR$_4$C(=O)—, —C(=O)NR$_4$—, —NR$_4$C(=O)—NR$_5$—, —NR$_4$S(=O)$_2$—, or —S(=O)$_2$NR$_4$— wherein R$_4$ and R$_5$ are independently hydrogen or optionally substituted $C_1$-$C_6$ alkyl; and z is 0 or 1.

Although the above definition potentially includes molecules of high molecular weight, it is preferable, in line with general principles of medicinal chemistry practice, that the compounds with which this invention is concerned should have molecular weights of no more than 600.

In another broad aspect the invention provides the use of a compound of formula (I) as defined above, or an N-oxide, salt, hydrate or solvate thereof in the preparation of a composition for inhibiting the activity of histone deacetylase.

The compounds with which the invention is concerned may be used for the inhibition of histone deacetylase activity, ex vivo or in vivo.

In one aspect of the invention, the compounds of the invention may be used in the preparation of a composition for the treatment of cell-proliferation disease, for example cancer cell proliferation and autoimmune diseases.

In another aspect, the invention provides a method for the treatment of the foregoing disease types, which comprises administering to a subject suffering such disease an effective amount of a compound of formula (I) as defined above.

TERMINOLOGY

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" means a hydrocarbon chain having from a to b carbon atoms, at least one double bond, and two unsatisfied valences.

As used herein the term "$C_a$-$C_b$ alkynyl" wherein a and b are integers refers to straight chain or branched chain hydrocarbon groups having from a to b carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_a$-$C_b$)alkynylene radical" wherein a and b are integers refers to a divalent hydrocarbon chain having from a to b carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, ($C_1$-$C_6$) alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, phenyl, halo (including fluoro, bromo and chloro), trifluoromethyl, trifluoromethoxy, nitro, nitrile (—CN), oxo, —COON, —COOR$^A$, —COR$^A$, —SO$_2$R$^A$, —CONH$_2$, —SO$_2$NH$_2$, —CONHR$^A$, —SO$_2$NHR$^A$, CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a ($C_1$-$C_6$)alkyl, ($C_3$-$C_6$) cycloalkyl, phenyl or monocyclic heteroaryl having 5 or 6 ring atoms, or R$^A$ and R$^B$ when attached to the same nitrogen atom form a cyclic amino group (for example morpholino, piperidinyl, piperazinyl, or tetrahydropyrrolyl). An "optional substituent" may be one of the foregoing substituent groups.

As used herein, the term "nitrogen substituent" means a substituent on a nitrogen atom which is selected from the following:
amino $C_{1-6}$ alkyl eg aminoethyl, $C_{1-3}$ alkylamino $C_{1-6}$ alkyl, $C_{1-3}$ dialkylamino $C_{1-6}$ alkyl, hydroxy $C_{1-6}$ alkyl eg hydroxyethyl, $C_{1-3}$ alkoxy $C_{1-6}$ alkyl eg methoxyethyl, mercapto $C_{1-3}$ alkyl, $C_{1-3}$ alkylmercapto $C_{1-6}$ alkyl, carboxamido $C_{1-6}$ alkyl e.g. —CH$_2$CONH$_2$, aminosulphonyl $C_{1-6}$ alkyl e.g. —CH$_2$SO$_2$NH$_2$, $C_{1-3}$ alkylaminosulphonyl $C_{1-6}$ alkyl e.g. —CH$_2$SO$_2$NHMe, $C_{1-3}$ dialkylaminosulphonyl $C_{1-6}$ alkyl e.g. —CH$_2$SO$_2$NMe$_2$, $C_{1-6}$ alkanoyl, $C_{1-6}$ alkylsulphonyl, aminosulphonyl (—SO$_2$NH$_2$), $C_{1-6}$ alkylaminosulphonyl e.g. —SO$_2$NHMe, $C_{1-6}$ dialkylaminosulphonyl e.g. —SO$_2$NMe$_2$, optionally substituted phenylaminosulphonyl, carboxamido (—CONH$_2$), $C_{1-6}$ alkylaminocarbonyl, $C_{1-6}$ dialkylaminocarbonyl, morpholinyl $C_{1-6}$ alkyl, imidazolyl $C_{1-6}$ alkyl, triazolyl $C_{1-6}$ alkyl, or monocyclic heterocycloalkyl $C_{1-6}$ alkyl, optionally substituted in the imidazolyl, triazolyl or heterocyclyl ring, eg piperidinyl $C_{1-6}$ alkyl, piperazinyl $C_{1-6}$ alkyl or 4-($C_{1-6}$ alkyl)piperazinyl $C_{1-6}$ alkyl.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

Compounds of the invention which contain one or more actual or potential chiral centres, because of the presence of asymmetric carbon atoms, can exist as a number of enantiomers or diastereoisomers with R or S stereochemistry at each chiral centre. The invention includes all such enantiomers or diastereoisomers and mixtures thereof.

In the compounds of the invention, in any compatible combination, and bearing in mind that the compounds preferably have a molecular weight of less than 600:

The Hydroxamate Group —C(═O)NHOH

In the compounds of the invention, the hydroxamate group functions as a metal binding group, interacting with the metal ion at the active site of the HDAC enzyme, which lies at the base of a pocket in the folded enzyme structure.

The Ring Containing Q, V and W

Each of Q, V and W may be —C═, or at least one of Q, V and W may be —N═, or Q may be —C═ and V and W may each be —N═; Currently preferred is the case where Q is —C═, V and W are each be —N═ and the HONHC(═O)— radical is attached to the 5-position of the resultant pyrimidin-2-yl radical.

The Ring A

Ring A radicals may be, for example, optionally substituted aromatic carbocyclic such as optionally substituted phenyl and naphthyl, or optionally substituted heteroaromatic such as optionally substituted pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,3,4-triazolyl, 1,2,5-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, indanyl, 3H-indolyl, benzimidazolyl, indazolyl, imidazo[1,2-a]pyridyl, benzothiazolyl, benzoxazolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl radicals.

Ring A radicals may also be, for example, optionally substituted non aromatic carbocyclic and heterocyclic, such as optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, 2,4-cyclopentadien-1-yl, 3,5-cyclohexadien-1-yl, tetrahydrofuranyl, pyrroline, eg 2- or 3-pyrrolinyl, pyrrolidinyl, dioxolanyl, eg 1,3-dioxolanyl, imidazolinyl, eg 2-imidazolinyl, imidazolidinyl, pyrazolinyl, eg 2-pyrazolinyl, pyrazolidinyl, pyranyl, eg 2- or 4-pyranyl, piperidinyl, 1,4-dioxanyl, morpholinyl, 1,4-dithianyl, thiomorpholinyl, piperazinyl, 1,3,5-trithianyl, oxazinyl, eg 2H-1, 3-, 6H-1,3-, H-1,2-, 2H-1,2- or 4H1,4-oxazinyl, 1,2,5-oxathiazinyl, isoxazinyl, oxathiazinyl, eg 1,2,5 or 1,2,6-oxathiazinyl, or 1,3,5-oxadiazinyl radicals.

Specific ring A radicals include the following ring systems, optionally substituted:

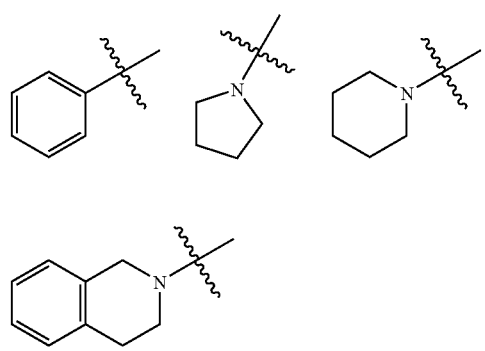

-continued
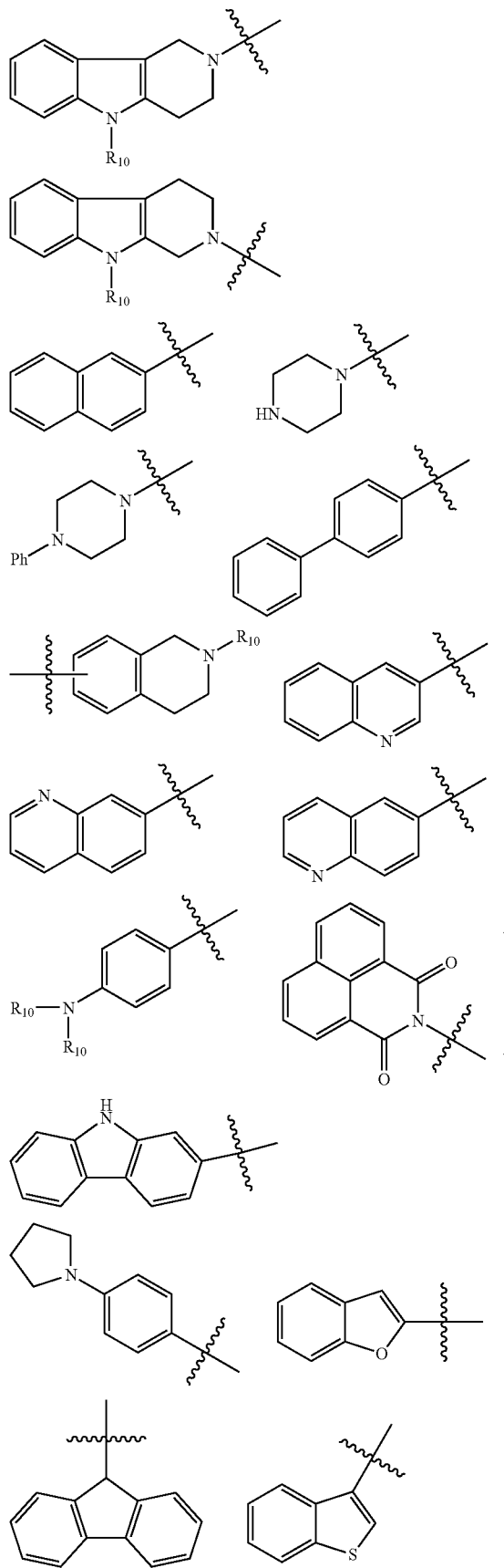
-continued
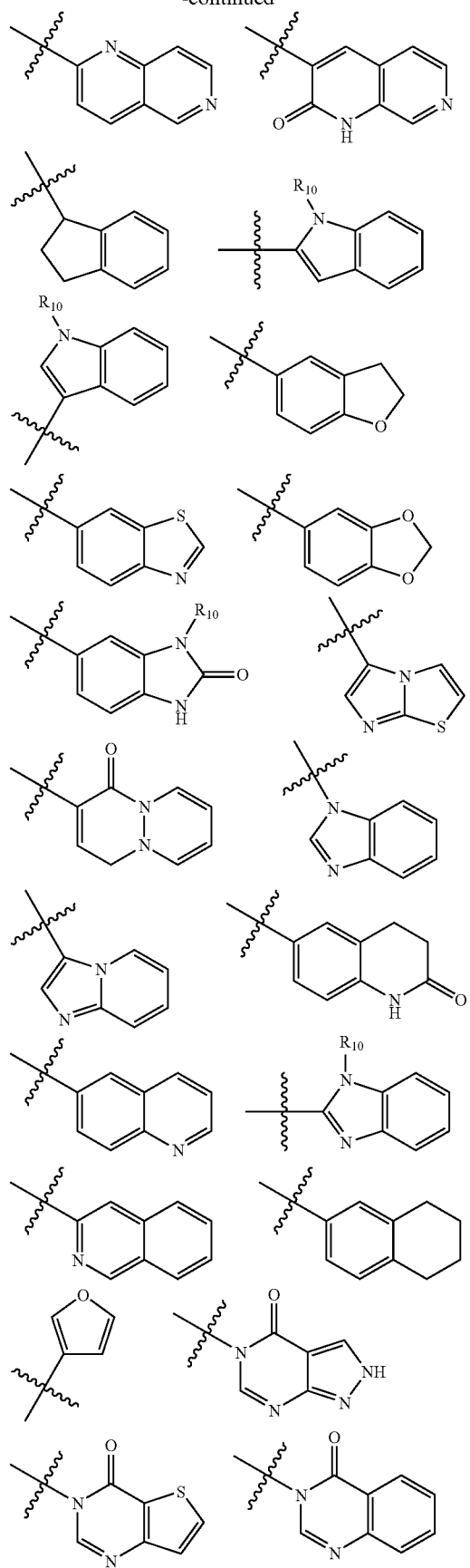

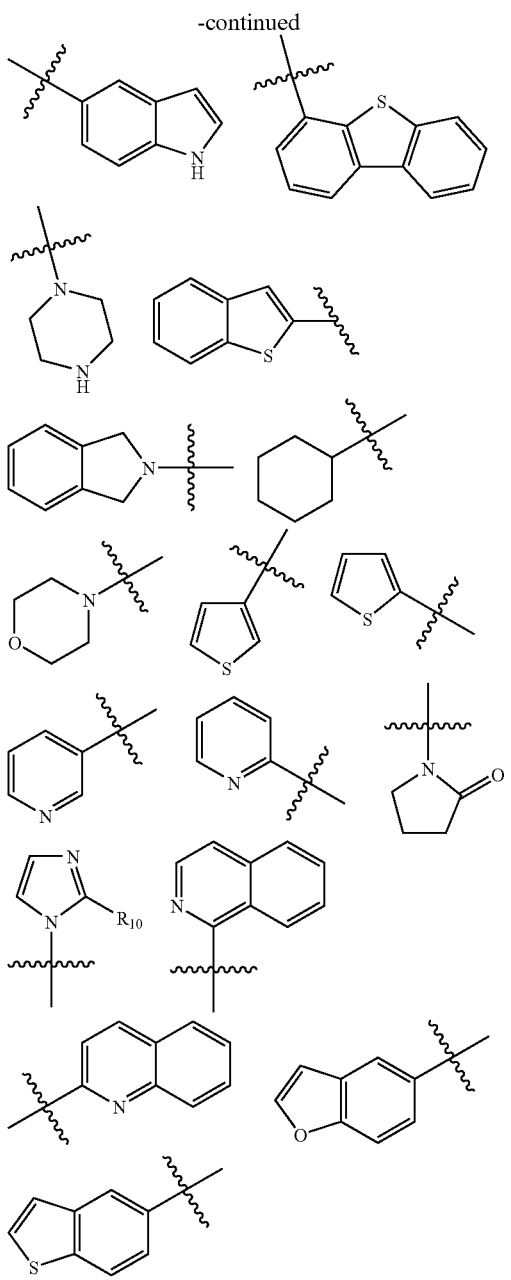

wherein $R_{10}$ is hydrogen or $C_1$-$C_6$ alkyl, the bond intersected by the wavy line connects to the -[Linker]- radical and the radical R in formula (I) is attached to any available ring atom.

Optional substituents in A may be, for example methyl, ethyl, n-propyl, isopropyl, fluorine, chlorine, bromine or iodine atoms, or a methylamino, ethylamino, hydroxymethyl, hydroxyethyl, methylthio, ethylthio, methoxy, ethoxy, n-propoxy, 2-hydroxyethoxy, 3-hydroxypropoxy, 2-aminoethoxy, 3-aminopropoxy, 2-(methylamino)ethoxy, 2-(dimethylamino)ethoxy, 3-(dimethylamino)propoxy, cyclopentyl, cyclohexyl, cyclohexylamino, trifluoromethyl, trifluoromethoxy, amino (—NH$_2$), aminomethyl, aminoethyl, dimethylamino, diethylamino, ethyl(methyl)amino, propyl(methyl)amino, 2-hydroxyethylamino, 3-hydroxypropylamino, 2-aminoethylamino, 3-aminopropylamino, 2-(methylamino) ethylamino, 2-(ethylamino)ethylamino, 2-(isopropylamino) ethylamino, 3-(isopropylamino)propylamino, 2-(dimethylamino)ethylamino, 2-(diethylamino)ethylamino, 2-(methylamino)ethyl(methyl)amino, 3-(methylamino)propyl(methyl)amino, nitro, cyano, hydroxyl, formyl, carboxyl (—CO$_2$H), —CH$_2$CO$_2$H, —OCH$_2$CO$_2$H, —CO$_2$CH$_3$, —CO$_2$CH$_2$CH$_3$, —CH$_2$CO$_2$CH$_2$CH$_3$, —CH$_2$CO$_2$CH$_2$Ph, t-butoxycarbonylmethoxy, acetyl, phenacyl, thio, thiomethyl, thioethyl, sulphonyl, methylsulphonyl, methylaminosulphonyl, ethylaminosulphonyl, dimethylaminosulphonyl, carboxamido, methylaminocarbonyl, ethylaminocarbonyl, dimethylaminocarbonyl, diethylaminocarbonyl, methylaminocarbonylmethyl, —NHC(S)NH$_2$, sulphonylamino (—NHSO$_2$H), methylsulphonylamino, dimethylsulphonylamino, aminosulphonylamino, (—NHSO$_2$NH$_2$), methylaminosulphonylamino, dimethylaminosulphonylamino, methylaminocarbonylamino, dimethylaminocarbonylamino, acetylamino, phenylcarbonylamino, aminomethylcarbonylamino, acetylaminomethyl, methoxycarbonylamino, t-butoxycarbonylamino, pyrrolidinyl, piperidynyl, piperazinyl, 4-methylpiperazinyl, homopiperazinyl, morpholinyl, imidazolyl, 1,2,4-triazolyl, 1,2,3-triazolyl, 1,3,4-triazolyl, 1,2,5-triazolyl, $C_{1-6}$ straight or branched chain alkyl, amino $C_{1-6}$ alkyl eg aminoethyl, $C_{1-3}$ alkylamino $C_{1-6}$ alkyl, $C_{1-3}$ dialkylamino $C_{1-6}$ alkyl, hydroxyl $C_{1-6}$ alkyl eg hydroxyethyl, $C_{1-3}$ alkoxyl $C_{1-6}$ alkyl eg methoxyethyl, thiol $C_{1-3}$ alkyl $C_{1-6}$, $C_{1-3}$ alkylthiol $C_{1-6}$ alkyl, $C_{1-6}$ alkanoyl, $C_{1-6}$ alkylsulphonyl, aminosulphonyl (—SO$_2$NH$_2$), $C_{1-6}$ alkylaminosulphonyl e.g. —SO$_2$NHMe, $C_{1-6}$ dialkylaminosulphonyl e.g. —SO$_2$NMe$_2$, optionally substituted phenylaminosulphonyl, carboxamido (—CONH$_2$), carboxamido $C_{1-6}$ alkyl e.g. CH$_2$CONH$_2$, $C_{1-6}$ alkylaminocarbonyl, $C_{1-6}$ dialkylaminocarbonyl, aminosulphonyl $C_{1-6}$ alkyl e.g. CH$_2$SO$_2$NH$_2$, $C_{1-3}$ alkylaminosulphonyl $C_{1-6}$ alkyl e.g. CH$_2$SO$_2$NHMe, $C_{1-3}$ dialkylaminosulphonyl $C_{1-6}$ alkyl e.g. CH$_2$SO$_2$NMe$_2$, $C_{1-6}$ morpholinyl $C_{1-6}$ alkyl, optionally substituted imidazolyl $C_{1-6}$ alkyl, optionally substituted triazolyl $C_{1-6}$ alkyl, optionally substituted hetero $C_{3-6}$ cycloalkyl $C_{1-6}$ alkyl eg piperidinyl $C_{1-6}$ alkyl, piperazinyl $C_{1-6}$ alkyl, and 4-($C_{1-6}$ alkyl)piperazinyl $C_{1-6}$ alkyl.

Currently preferred rings A include optionally substituted phenyl, cyclohexyl, naphthyl, quinolin-2-yl, and 1,3-dihydro-isoindol-2-yl. Substituents which may be present in such preferred rings A include halogen, particularly fluoro and chloro. Specifically the radical -A- in formula (I) above, when present, may be 1,4-phenylene or 1,4-cyclohexylene.

The [Linker] Radical

-[Linker]- serves to link the divalent B radical to the ring A, when present. Thus, it may be selected from the following examples:

(i) a bond. This will normally be the case when ring A is not present;

(ii) —O—, —S—, —C(=O)—, —S(=O)$_2$—, —NR$^C$—, —C(=O)NR$^C$—, —S(=O)$_2$NR$^C$—, —NR$^C$C (=O)—, —NR$^C$S(=O)$_2$—, —NR$^C$(CH$_2$)$_m$—, —NR$^C$C(=O)(CH$_2$)$_m$—, —NR$^C$S(=O)$_2$(CH$_2$)$_m$, —NR$^D$C(=O)NR$^C$—, —NR$^C$C(=O)(CH$_2$)$_m$Ar—, or —NR$^C$S(=O)$_2$(CH$_2$)$_m$Ar— wherein R$^C$ and R$^D$ are independently hydrogen, $C_1$-$C_4$ alkyl, or a nitrogen substituent, m is 0, 1, 2, 3, 4 or 5 and Ar is a divalent phenyl radical or a divalent mono-, or bi-cyclic heteroaryl radical having 5 to 13 ring members; and (iii) an optionally substituted, straight or branched, $C_1$-$C_6$ alkylene, $C_2$-$C_6$ alkenylene or $C_2$-$C_6$ alkynylene radical which may optionally contain or terminate in an ether (—O—), thioether (—S—) or amino (—NR$^A$—) link wherein R$^A$ is hydrogen, $C_1$-$C_3$ alkyl, or a nitrogen substituent;

When —Ar— is present in -[Linker]- it may be a divalent radical selected from the following:

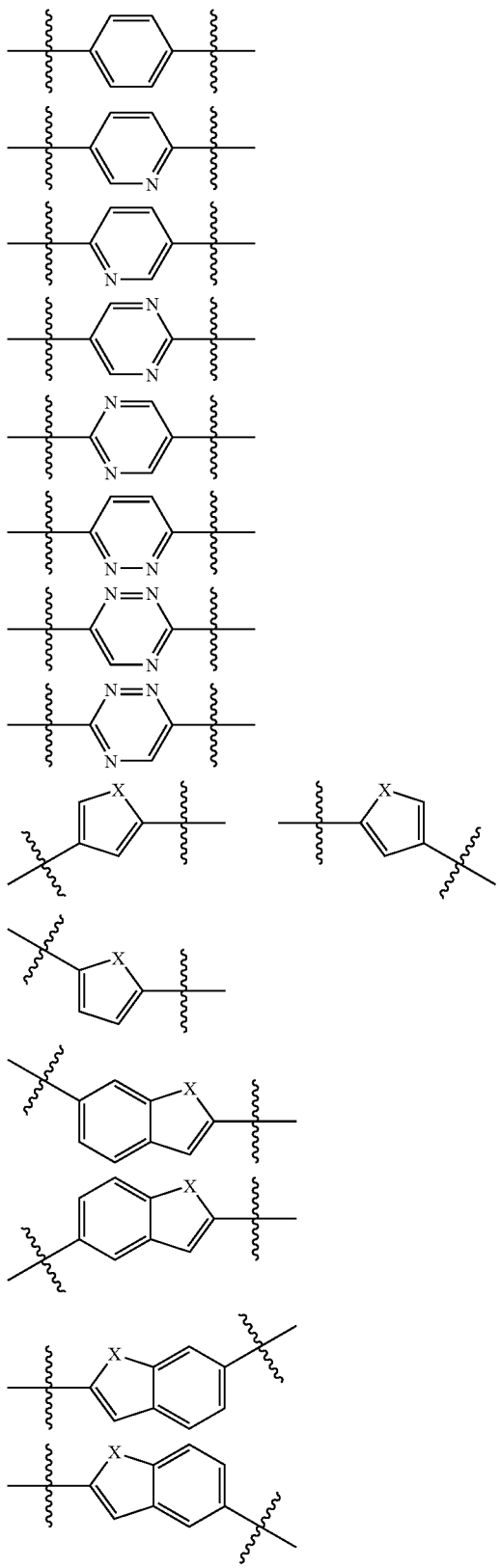

wherein X is O, S or NH. For example, —Ar— when present in -[Linker]- may be a divalent phenylene, such as a 1,4-phenylene, radical.

Examples of -[Linker]- include those present in the compounds of the specific examples herein.

The Group $Z^1$

Case (a): $Z^1$ is a Radical of Formula —$(CH_2)_z$—$X^1$-$L^1$-Y—NHCHR$_1$R$_2$ In Group R$_1$ in $Z^1$ Case (a)

The ester group R$_1$ must be one which in the compound of the invention is hydrolysable by one or more intracellular carboxyesterase enzymes to a carboxylic acid group. Intracellular carboxyesterase enzymes capable of hydrolysing the ester group of a compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxyesterase hydrolyses the free amino acid ester to the parent acid it will, subject to the N-carbonyl dependence of hCE-2 and hCE-3 discussed above, also hydrolyse the ester motif when covalently conjugated to the HDAC inhibitor. Hence, the broken cell assay and/or the isolated carboxyesterase assay described herein provide a straightforward, quick and simple first screen for esters which have the required hydrolysis profile. Ester motifs selected in that way may then be re-assayed in the same carboxyesterase assay when conjugated to the inhibitor via the chosen conjugation chemistry, to confirm that it is still a carboxyesterase substrate in that background.

Subject to the requirement that they be hydrolysable by intracellular carboxyesterase enzymes, examples of particular ester groups R$_1$ include those of formula —(C=O)OR$_9$ wherein R$_9$ is R$_7$R$_8$CH— wherein (i) R$_7$ is hydrogen or optionally substituted (C$_1$-C$_3$)alkyl-(Z$^1$)$_a$-[(C$_1$-C$_3$)alkyl]$_b$— or (C$_2$-C$_3$)alkenyl-(Z$^1$)$_a$-[(C$_1$-C$_3$)alkyl]$_b$— wherein a and b are independently 0 or 1 and $Z^1$ is —O—, —S—, or —NR$_{10}$— wherein R$_{10}$ is hydrogen or C$_1$-C$_3$ alkyl, and R$_8$ is hydrogen or (C$_1$-C$_3$) alkyl-;

(ii) R$_7$ is hydrogen or optionally substituted R$_{10}$R$_{11}$N—(C$_1$-C$_3$)alkyl- wherein R$_{10}$ is hydrogen or C$_1$-C$_3$ alkyl and R$_{11}$ is hydrogen or C$_1$-C$_3$ alkyl; or R$_{10}$ and R$_{11}$ together with the nitrogen to which they are attached form an optionally substituted monocyclic heterocyclic ring of 5- or 6-ring atoms or bicyclic heterocyclic ring system of 8 to 10 ring atoms, and R$_8$ is hydrogen or (C$_1$-C$_3$)alkyl-; or (iii) R$_7$ and R$_8$ taken together with the carbon to which they are attached form an optionally substituted monocyclic carbocyclic ring of from 3 to 7 ring atoms or bicyclic carbocyclic ring system of 8 to 10 ring atoms.

Within these classes, R$_9$ may be, for example, methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl, methoxyethyl, indanyl, norbornyl, dimethylaminoethyl, morpholinoethyl. Currently preferred is where R$_{90}$ is cyclopentyl.

Macrophages are known to play a key role in inflammatory disorders through the release of cytokines in particular TNFα and IL-1 (van Roon et al Arthritis and Rheumatism, 2003, 1229-1238). In rheumatoid arthritis they are major contributors to the maintenance of joint inflammation and joint destruction. Macrophages are also involved in tumour growth and development (Naldini and Carraro, Curr Drug Targets Inflamm Allergy, 2005, 3-8). Hence agents that selectively target macrophage cell proliferation could be of value in the treatment of cancer and autoimmune disease. Targeting specific cell types would be expected to lead to reduced side-effects. The inventors have discovered a method of targeting inhibitors to macrophages which is based on the observation that the way in which the esterase motif is linked to the inhibitor determines whether it is hydrolysed, and hence whether or not it accumulates in different cell types. Specifically it has been found that macrophages contain the human carboxylesterase hCE-1 whereas other cell types do not. In the general formula (I) when the nitrogen of the esterase motif $R_1CH(R_2)NH$— is not directly linked to a carbonyl (—C(=O)—), ie when Y is not a —C(=O), —C(=O)O— or —C(=O)$NR_3$— radical, the ester will only be hydrolysed by hCE-1 and hence the inhibitors will only accumulate in macrophages.

The Amino Acid Side Chain $R_2$ in $Z^1$ Case (a)

Subject to the requirement that the ester group $R_1$ be hydrolysable by intracellular carboxylesterase enzymes, the identity of the side chain group $R_2$ is not critical.

Examples of amino acid side chains include:

$C_1$-$C_6$ alkyl, phenyl, 2, -3-, or 4-hydroxyphenyl, 2, -3-, or 4-methoxyphenyl, 2, -3-, or 4-pyridylmethyl, benzyl, phenylethyl, 2-, 3-, or 4-hydroxybenzyl, 2, -3-, or 4-benzyloxybenzyl, 2, -3-, or 4-$C_1$-$C_6$ alkoxybenzyl, and benzyloxy($C_1$-$C_6$alkyl)- groups;

the characterising group of a natural α amino acid, in which any functional group may be protected;

groups -[Alk]$_n R_6$ where Alk is a ($C_1$-$C_6$)alkyl or ($C_2$-$C_6$) alkenyl group optionally interrupted by one or more —O—, or —S— atoms or —N($R_7$)— groups [where $R_7$ is a hydrogen atom or a ($C_1$-$C_6$)alkyl group], n is 0 or 1, and $R_6$ is an optionally substituted cycloalkyl or cycloalkenyl group;

a benzyl group substituted in the phenyl ring by a group of formula —OCH$_2$COR$_8$ where $R_8$ is hydroxyl, amino, ($C_1$-$C_6$) alkoxy, phenyl($C_1$-$C_6$)alkoxy, ($C_1$-$C_6$)alkylamino, di(($C_1$-$C_6$)alkyl)amino, phenyl($C_1$-$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid;

a heterocyclic($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$) alkylamino, di-($C_1$-$C_6$)alkylamino, mercapto, ($C_1$-$C_6$)alkylthio, hydroxy($C_1$-$C_6$)alkyl, mercapto($C_1$-$C_6$)alkyl or ($C_1$-$C_6$)alkylphenylmethyl; and a group —C$R_a R_b R_c$ in which:

each of $R_a$, $R_b$ and $R_c$ is independently hydrogen, ($C_1$-$C_6$) alkyl, ($C_2$-$C_6$)alkenyl, ($C_2$-$C_6$)alkynyl, phenyl($C_1$-$C_6$) alkyl, ($C_3$-$C_8$)cycloalkyl; or $R_c$ is hydrogen and $R_a$ and $R_b$ are independently phenyl or heteroaryl such as pyridyl; or $R_c$ is hydrogen, ($C_1$-$C_6$)alkyl, ($C_2$-$C_6$)alkenyl, ($C_2$-$C_6$) alkynyl, phenyl($C_1$-$C_6$)alkyl, or ($C_3$-$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$-$C_6$)alkyl, ($C_2$-$C_6$) alkenyl, ($C_2$-$C_6$)alkynyl, phenyl($C_1$-$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$-$C_4$)perfluoroalkyl, —CH$_2$OH, —CO$_2$($C_1$-$C_6$)alkyl, —O($C_1$-$C_6$)alkyl, —O($C_2$-$C_6$)alkenyl, —S($C_1$-$C_6$) alkyl, —SO($C_1$-$C_6$)alkyl, —SO$_2$($C_1$-$C_6$)alkyl, —S($C_2$-$C_6$)alkenyl, —SO($C_2$-$C_6$)alkenyl, —SO$_2$($C_2$-$C_6$)alkenyl or a group -Q-W wherein Q represents a bond or —O—, —S—, —SO— or —SO$_2$— and W represents a phenyl, phenylalkyl, ($C_3$-$C_8$)cycloalkyl, ($C_3$-$C_8$)cycloalkylalkyl, ($C_4$-$C_8$)cycloalkenyl, ($C_4$-$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$-$C_6$)alkyl, —CONH$_2$, —CONH($C_1$-$C_6$)alkyl, —CONH($C_1$-$C_6$alkyl)$_2$, —CHO, —CH$_2$OH, ($C_1$-$C_4$)perfluoroalkyl, —O($C_1$-$C_6$)alkyl, —S($C_1$-$C_6$)alkyl, —SO($C_1$-$C_6$)alkyl, —SO$_2$($C_1$-$C_6$)alkyl, —NO$_2$, —NH$_2$, —NH($C_1$-$C_6$) alkyl, —N(($C_1$-$C_6$)alkyl)$_2$, —NHCO($C_1$-$C_6$)alkyl, ($C_1$-$C_6$)alkyl, ($C_2$-$C_6$)alkenyl, ($C_2$-$C_6$)alkynyl, ($C_3$-$C_8$)cycloalkyl, ($C_4$-$C_8$)cycloalkenyl, phenyl or benzyl.

Examples of particular $R_2$ groups include hydrogen (the glycine "side chain"), benzyl, phenyl, cyclohexylmethyl, cyclohexyl, pyridin-3-ylmethyl, tert-butoxymethyl, iso-butyl, sec-butyl, tert-butyl, 1-benzylthio-1-methylethyl, 1-methylthio-1-methylethyl, 1-mercapto-1-methylethyl, and phenylethyl. Presently preferred $R_2$ groups include phenyl, benzyl, and iso-butyl, cyclohexyl and t-butoxymethyl.

For compounds of the invention which are to be administered systemically, esters with a slow rate of carboxylesterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. In the compounds of this invention, if the carbon adjacent to the alpha carbon of the alpha amino acid ester is monosubstituted, ie $R_2$ is CH$_2 R^z$ ($R^z$ being the mono-substituent) then the esters tend to be cleaved more rapidly than if that carbon is di- or tri-substituted, as in the case where $R_2$ is, for example, phenyl or cyclohexyl.

The Radical —Y-$L^1 X^1$-[CH$_2$]$_z$— in $Z^1$ Case (a)

This radical (or bond) arises from the particular chemistry strategy chosen to link the amino acid ester motif $R_1$CH($R_2$) NH— to the ring A (when present), or ring B (via the -[Linker]- radical). Clearly the chemistry strategy for that coupling may vary widely, and thus many combinations of the variables Y, $L^1$, $X^1$ and z are possible. However, when the inhibitor is bound to the HDAC enzyme at its active site, the rings B and/or A are located at the top of, or within, the metal-ion-containing pocket of the enzyme, so by linking the amino acid ester motif to those rings it generally extends in a direction away from that pocket, and thus minimises or avoids interference with the binding mode of the inhibitor. Hence the precise combination of variables making up the linking chemistry between the amino acid ester motif and the rings B and/or A will often be irrelevant to the primary binding mode of the compound as a whole. On the other hand, that linkage chemistry may in some cases pick up additional binding interactions with the enzyme at the top of, or adjacent to, the metal ion-containing pocket, thereby enhancing binding.

It should also be noted that the benefits of the amino acid ester motif described above (facile entry into the cell, carboxylesterase hydrolysis within the cell, and accumulation within the cell of active carboxylic acid hydrolysis product) are best achieved when the linkage between the amino acid ester motif and the rings B and/or A is not a substrate for peptidase activity within the cell, which might result in cleavage of the amino acid from the molecule. Of course, stability to intracellular peptidases is easily tested by incubating the compound with disrupted cell contents, and analysing for any such cleavage.

With the foregoing general observations in mind, taking the variables making up the radical —Y-$L^1$-$X^1$—[$CH_2$]$_z$— in turn:

z may be 0 or 1, so that a methylene radical linked to the ring A or the ring B is optional;

specific preferred examples of Y when macrophage selectivity is not required include —(C=O)—, —(C=O)NH—, and —(C=O)O—; Where macrophage selectivity is required any of the other options for Y, including the case where Y is a bond, are appropriate.

In the radical $L^1$, examples of $Alk^1$ and $Alk^2$ radicals, when present, include —$CH_2$—, —$CH_2CH_2$— —$CH_2CH_2CH_2$—, —$CH_2CH_2CH_2CH_2$—, —CH=CH—, —CH=CHCH$_2$—, —$CH_2$CH=CH—, $CH_2$CH=CHCH$_2$—C≡C—, —C≡CCH$_2$—, $CH_2$C≡C—, and $CH_2$C≡CCH$_2$. Additional examples of $Alk^1$ and $Alk^2$ include —$CH_2$W—, —$CH_2CH_2$W— —$CH_2CH_2$WCH$_2$—, —$CH_2CH_2$WCH(CH$_3$)—, —$CH_2$WCH$_2$CH$_2$—, —$CH_2$WCH$_2$CH$_2$WCH$_2$—, and —WCH$_2$CH$_2$— where W is —O—, —S—, —NH—, —N(CH$_3$)—, or —$CH_2CH_2$N($CH_2CH_2$OH)$CH_2$—. Further examples of $Alk^1$ and $Alk^2$ include divalent cyclopropyl, cyclopentyl and cyclohexyl radicals.

In $L^1$, when q is 0, the radical is a hydrocarbon chain (optionally substituted and perhaps having an ether, thioether or amino linkage). Presently it is preferred that there be no optional substituents in $L^1$. When both p and r are O, C is a divalent mono- or bicyclic carbocyclic or heterocyclic radical with 5-13 ring atoms (optionally substituted). When n is 1 and at least one of p and r is 1, $L^1$ is a divalent radical including a hydrocarbon chain or chains and a mono- or bicyclic carbocyclic or heterocyclic radical with 5-13 ring atoms (optionally substituted). When present, $Q^1$ may be, for example, a divalent phenyl, naphthyl, cyclopropyl, cyclopentyl, or cyclohexyl radical, or a mono-, or bi-cyclic heterocyclicl radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention, $L^1$, p and r may be 0 with q being 1. In other embodiments, q and r may be 0 with p being 1. In further embodiments, p, q and r may be all 0. In still further embodiments p may be 0, q may be 1 with $Q^1$ being a monocyclic heterocyclic radical, and r may be 0 or 1. $Alk^1$ and $Alk^2$, when present, may be selected from —$CH_2$—, —$CH_2CH_2$—, and —$CH_2CH_2CH_2$— and $Q^1$ may be 1,4-phenylene.

Specific examples of the radical —Y-$L^1$-$X^1$—[$CH_2$]$_z$— include —C(=O)— and —C(=O)NH— as well as —(CH$_2$)$_v$—, —(CH$_2$)$_v$O—, —C(=O)—(CH$_2$)$_v$—, —C(=O)—(CH$_2$)$_v$O—, —C(=O)—NH—(CH$_2$)$_w$—, —C(=O)—NH—(CH$_2$)$_w$O—

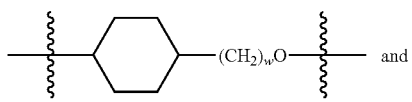 and

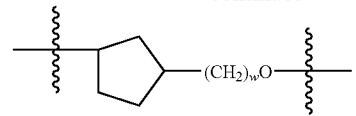

wherein v is 1, 2, 3 or 4 and w is 1, 2 or 3, such as —CH$_2$—, —CH$_2$O—, —C(=O)—CH$_2$—, —C(=O)—CH$_2$O—, —C(=O)—NH—CH$_2$—, and —C(=O)—NH—CH$_2$O—.

Case (b): $Z^1$ is a Radical of Formula —(CH$_2$)$_z$—$Y^1$-$L^1$-R

The Radical R in $Z^1$ Case (b)

R is a radical of formula (X) or (Y)

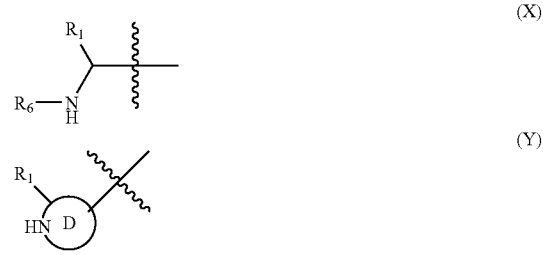

In formula (X) and (Y), $R_1$ is a carboxylic acid group or an ester group which is hydrolysable by one or more intracellular carboxylesterase enzymes to a carboxylic acid group, as defined and discussed above with reference to $Z^1$ case (a).

The Ring D in $Z^1$ Case (b)

When R is a group of formula (Y), examples of R include:

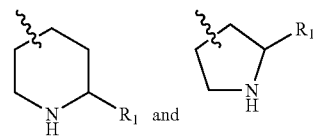

wherein $R_1$ is as defined and discussed above.

The Group $R_6$ in $Z^1$ Case (b)

The group $R_6$ is present in the compounds of the invention in this case when R is a radical of formula (X)

As mentioned above, if the modulator is intended to act only in cell types where hCE-1 is present, such as macrophages, the amino group of the carboxylesterase motif should be directly linked to a group other than carbonyl. In such cases $R_6$ may be optionally substituted $C_1$-$C_6$ alkyl, $C_3$-$C_7$cycloalkyl, aryl or heteroaryl, for example methyl, ethyl, n- or isopropyl, cyclopropyl, cyclopentyl, cyclohexyl, phenyl, or pyridyl. In cases where macrophage specificity is not required, $R_6$ may be hydrogen or —(C=O)$R^D$, wherein $R^D$ is optionally substituted ($C_1$-$C_6$)alkyl such as methyl, ethyl, n- or isopropyl, or n-, iso- or sec-butyl, ($C_3$-$C_7$)cycloalkyl such as cyclopropyl, cyclopentyl, cyclohexyl, phenyl, pyridyl, thienyl, phenyl($C_1$-$C_6$ alkyl)-, thienyl($C_1$-$C_6$ alkyl)- or pyridyl($C_1$-$C_6$ alkyl)- such as benzyl, 4-methoxyphenylmethylcarbonyl, thienylmethyl or pyridylmethyl.

$R_6$ may also be, for example —(C=O)O$R^D$, or —(C=O)NH$R^D$ wherein $R^D$ is hydrogen or optionally substituted ($C_1$-$C_6$)alkyl such as methyl, ethyl, or n- or isopropyl.

For compounds of the invention which are to be administered systemically, esters with a slow rate of esterase cleavage are preferred, since they are less susceptible to pre-systemic metabolism. Their ability to reach their target tissue intact is therefore increased, and the ester can be converted inside the cells of the target tissue into the acid product.

However, for local administration, where the ester is either directly applied to the target tissue or directed there by, for example, inhalation, it will often be desirable that the ester has a rapid rate of esterase cleavage, to minimise systemic exposure and consequent unwanted side effects. If a carbon atom to which the group R is attached is unsubstituted, ie R is attached to a methylene (—$CH_2$)— radical, then the esters tend to be cleaved more rapidly than if that carbon is substituted, or is part of a ring system such as a phenyl or cyclohexyl ring.

The Radical -$L^1$-$Y^1$—[$CH_2$]$_z$— in $Z^1$ Case (b)

As in the $Z^1$ case (a), this radical (or bond) arises from the particular chemistry strategy chosen to link the amino acid ester motif R in substituent Y to the rest of the molecule. Clearly the chemistry strategy for that coupling may vary widely, and thus many combinations of the variables $Y^1$, $L^1$, and z are possible. However, when the inhibitor is bound to the enzyme at its active site, the amino acid ester motif generally extends in a direction away from the enzyme, and thus minimises or avoids interference with the binding mode of the inhibitor. Hence the precise combination of variable making up the linking chemistry between the amino acid ester motif and the rest of the molecule will often be irrelevant to the primary binding mode of the compound as a whole.

With the foregoing general observations in mind, taking the variables making up the radical -$L^1$-$Y^1$—-[$CH_2$]$_z$— in turn:

z may be 0 or 1, so that a methylene radical linked to the rest of the molecule is optional;

$Y^1$ may be, for example, —$NR_3$—, —S—, —O—, —C(=O)$NR_3$—, —$NR_3$C(=O)—, or —C(=O)O—, wherein $R_3$ is hydrogen or optionally substituted $C_1$-$C_6$ alkyl such as —$CH_2CH_2OH$;

In the radical $L^1$, examples of $Alk^1$ and $Alk^2$ radicals, when present, include —$CH_2$—, —$CH_2CH_2$— —$CH_2CH_2CH_2$—, —$CH_2CH_2CH_2CH_2$—, —CH=CH—, —CH=CHCH$_2$—, —$CH_2$CH=CH—, $CH_2$CH=CHCH$_2$—, —C≡C—, —C≡CCH$_2$—, $CH_2$C≡C—, and $CH_2$C≡CCH$_2$. Additional examples of $Alk^1$ and $Alk^2$ include —$CH_2$W—, —$CH_2CH_2$W— —$CH_2CH_2WCH_2$—, —$CH_2CH_2WCH(CH_3)$—, —$CH_2WCH_2CH_2$—, —$CH_2WCH_2CH_2WCH_2$—, and —$WCH_2CH_2$— where W is —O—, —S—, —NH—, —N(CH$_3$)—, or —$CH_2CH_2N(CH_2CH_2OH)CH_2$—. Further examples of $Alk^1$ and $Alk^2$ include divalent cyclopropyl, cyclopentyl and cyclohexyl radicals.

$Alk^1$ and $Alk^2$ when present may also be branched chain alkyl such as —CH(CH$_3$)—, —C(CH$_3$)$_2$—, or in either orientation —$CH_2$CH(CH$_3$)—, —$CH_2$C(CH$_3$)$_2$—.

In $L^1$, when n is 0, the radical is a hydrocarbon chain (optionally substituted and perhaps having an ether, thioether or amino linkage). Presently it is preferred that there be no optional substituents in $L^1$. When both m and p are O, C is a divalent mono- or bicyclic carbocyclic or heterocyclic radical with 5-13 ring atoms (optionally substituted). When n is 1 and at least one of m and p is 1, $L^1$ is a divalent radical including a hydrocarbon chain or chains and a mono- or bicyclic carbocyclic or heterocyclic radical with 5-13 ring atoms (optionally substituted). When present, Q may be, for example, a divalent phenyl, naphthyl, cyclopropyl, cyclopentyl, or cyclohexyl radical, or a mono-, or bi-cyclic heterocyclic radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention, $L^1$, m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. $Alk^1$ and $Alk^2$, when present, may be selected from —$CH_2$—, —$CH_2CH_2$—, and —$CH_2CH_2CH_2$— and Q may be 1,4-phenylene.

Specific examples of the radical -$L^1$-$Y^1$—[$CH_2$]$_z$ include —(CH$_2$)$_3$NH—, —$CH_2$C(=O)NH—, —$CH_2CH_2$C(=O)NH—, —$CH_2$C(O)O—, —$CH_2$S—, —$CH_2CH_2$C(O)O—, —(CH$_2$)$_4$NH—, —$CH_2CH_2$S—, —$CH_2$O, —$CH_2CH_2$O—,

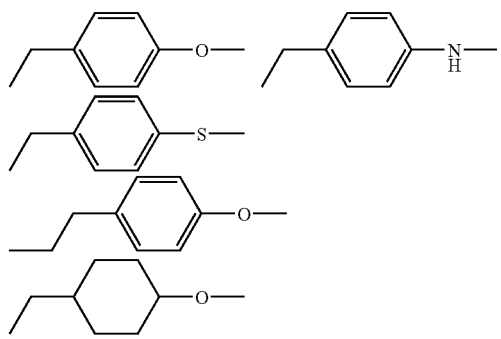

As mentioned above, the compounds with which the invention is concerned are HDAC inhibitors, and may therefore be of use in the treatment of cell proliferative disease, such as cancer, in humans and other mammals.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced organic chemistry*", 4*th* Edition (Wiley), J March, "*Comprehensive Organic Transformation*", 2*nd* Edition (Wiley), R. C. Larock, "*Handbook of Heterocyclic Chemistry*", 2*nd* Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*". The synthetic routes used in the preparation of the compounds of the Examples below may be adapted for the preparation of analogous compounds.

ABBREVIATIONS

MeOH=methanol
EtOH=ethanol
EtOAc=ethyl acetate
Boc=tert-butoxycarbonyl
DCM=dichloromethane
DMF=dimethylformamide
DMSO=dimethyl sulfoxide
TFA=trifluoroacetic acid
THF=tetrahydrofuran
$Na_2CO_3$=sodium carbonate
$K_2CO_3$=potassium carbonate
HCl=hydrochloric acid
aq=aqueous solution
DIPEA=diisopropylethylamine
NaH=sodium hydride
NaOH=sodium hydroxide
$NaHCO_3$=sodium hydrogen carbonate
Pd/C=palladium on carbon
TBME=tert-butyl methyl ether
$N_2$=nitrogen
PyBop=benzotriazole-1-yl-oxy-tris-pyrrolidino-phosphonium hexafluorophosphate
$Na_2SO_4$=sodium sulphate
$Et_3N$=triethylamine
$NH_3$=ammonia
TMSCl=trimethylchlorosilane
$NH_4Cl$=ammonium chloride
$LiAlH_4$=lithium aluminium hydride
PyBrOP=bromo-tris-pyrrolidino phosphoniumhexafluorophosphate
$MgSO_4$=magnesium sulfate
$^nBuLi$=n-butyllithium
$CO_2$=carbon dioxide
EDCl=N-(3-dimethylaminopropyl)-N'-ethylcarbodiimide hydrochloride
$Et_2O$=diethyl ether
LiOH=lithium hydroxide
HOBt=1-hydroxybenzotriazole
TLC=thin layer chromatography
LCMS=liquid chromatography/mass spectrometry
mL=milliliter(s)
g=gram(s)
mg=milligram(s)
mol=moles
mmol=millimole(s)
HPLC=high performance liquid chromatography
NMR=nuclear magnetic resonance
RT=room temperature
h=hour(s)

The following Examples illustrate the preparation of specific compounds of the invention, and the HDAC inhibitory properties thereof:

Preparation of Aminoacid Esters (Intermediates A to D)

Scheme 1

Route I. Used for the preparation of Intermediate A and Intermediate B

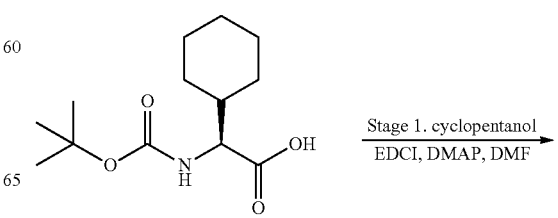

Stage 1. cyclopentanol
EDCI, DMAP, DMF

23
-continued

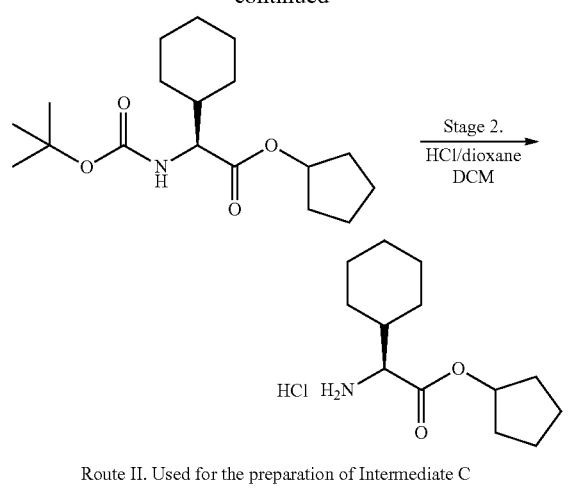

Route II. Used for the preparation of Intermediate C

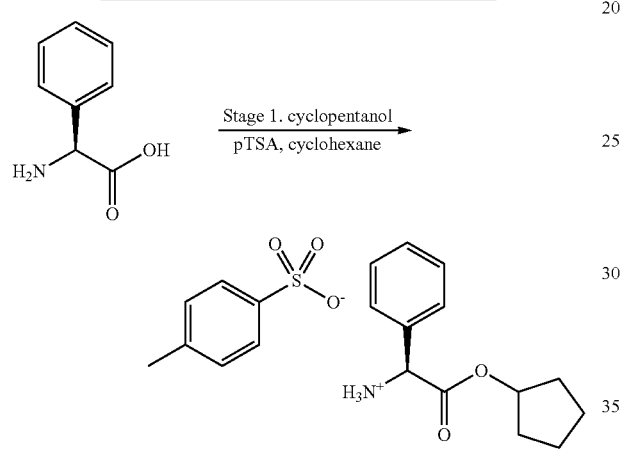

Route III. Used for the preparation of Intermediate D

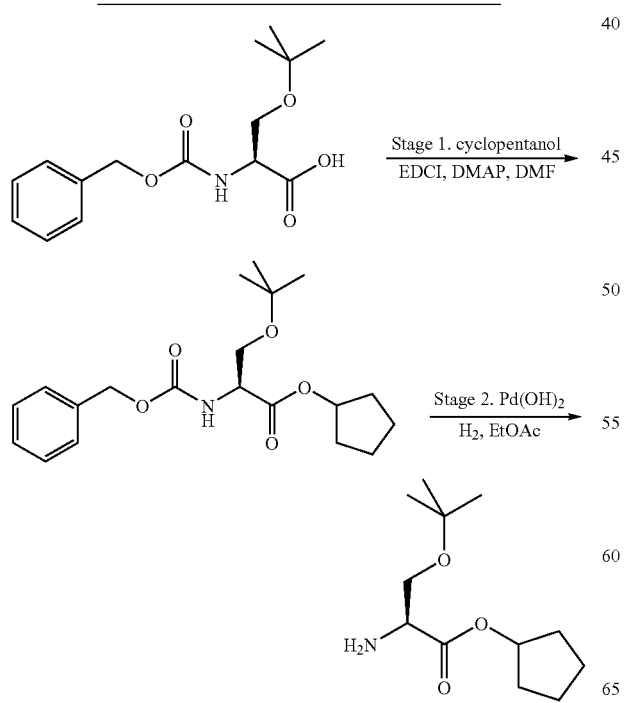

24
Compounds Prepared:

FIG. 1

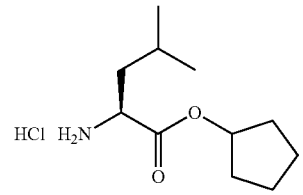

Intermediate A

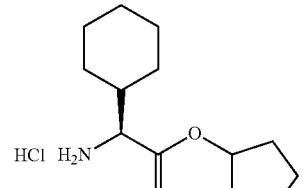

Intermediate B

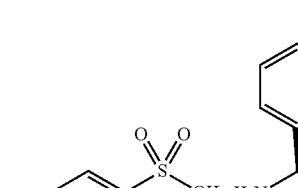

Intermediate C

Intermediate D

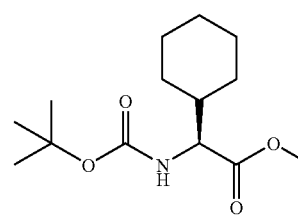

Synthesis of Compounds Outlined in FIG. 1
Route I (Exemplified for Intermediate B)
Stage 1—Ester Formation To a solution of (S)-2-tert-butoxycarbonylamino-3-cyclohexyl-propionic acid (5 g, 19.4 mmol) in DMF (50 mL) at 0° C. was added cyclopentanol (8.8 mL, 97.15 mmol), EDCl (4.09 g, 21.37 mmol) and finally DMAP (237 mg, 1.94 mmol). The reaction mixture was warmed to RT and stirred for 18 h.

The DMF was removed in vacuo to give a clear oil. This was separated between water and EtOAc. The organic phase was dried (MgSO₄) and concentrated in vacuo. The crude extract was purified by column chromatography (25% EtOAC in heptane) to yield the desired product as a clear oil (14.87 g, 55%). ¹H NMR (300 MHz, d₆-DMSO) δ: 7.09 (1H, d), 5.08 (1H, t), 3.76 (1H, t), 1.50-1.85 (10H, br m), 1.39 (9H, s), 1.00-1.25 (9H, br m).

Stage 2—Boc Deprotection to Yield Cyclopentyl (2S)-amino (cyclohexyl)acetate Hydrochloride (Intermediate B)

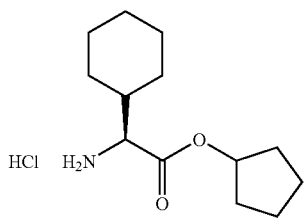 [SMILES: Cl ; N[C@H](C(=O)OC1CCCC1)C1CCCCC1]

Stage 1 product (14.87 g, 45.69 mmol) was dissolved in DCM (100 mL) and treated with 4M HCl/dioxane (22.8 mL, 91.38 mmol) and the reaction mixture was stirred at RT for 24 h. The crude mixture was concentrated under reduced pressure to give an orange oil. This was triturated with Et₂O to give a white precipitate. This was further washed with Et₂O to give the desired product as a white powder (7.78 g, 65%). ¹H NMR (300 MHz, d₅-DMSO) δ: 8.45 (3H, br s), 5.22 (1H, t), 3.28 (1H, d), 1.95-1.50 (10H, br m), 1.30-0.90 (9H, br m).

Route II

Stage 1—Ester Formation to Yield (1S)-2-(cyclopentyloxy)-2-oxo-1-phenylethanaminium 4-methylbenzenesulfonate (Intermediate C)

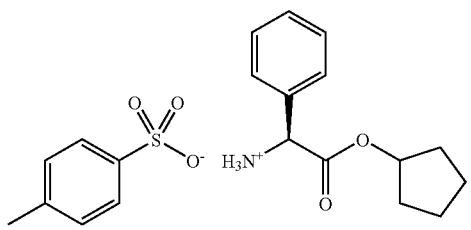 [SMILES: Cc1ccc(S(=O)(=O)[O-])cc1 ; [NH3+][C@H](C(=O)OC1CCCC1)c1ccccc1]

To a slurry of (S)-phenylglycine (5 g, 33.1 mmol) in cyclohexane (150 mL) was added cyclopentanol (29.84 mL, 331 mmol) and p-toluene sulfonic acid (6.92 g, 36.4 mmol). The reaction was fitted with a Dean-Stark receiver and heated to 135° C. for complete dissolution. After 12 h, the reaction was cooled to RT leading to the precipitation of a white solid. The solid was filtered and washed with EtOAc before drying under reduced pressure to give the required product as a white powder (11.01 g, 85%). ¹H NMR (300 MHz, d₆-DMSO) δ 8.82 (2H, br s), 8.73 (1H, br s), 7.47 (7H, m), 7.11 (2H, d), 5.25 (1H, br s), 5.18° (1H, m), 2.29 (3H, s), 1.87-1.36 (8H, m).

Route III

Stage 1—Ester Formation

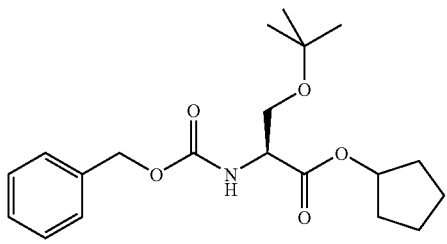 [SMILES: CC(C)(C)OC[C@H](NC(=O)OCc1ccccc1)C(=O)OC1CCCC1]

To a solution of (S)-2-benzyloxycarbonylamino-3-tert-butoxy-propionic acid (25 g, 84.65 mmol) in DMF (250 mL) at 0° C. was added cyclopentanol (15.36 mL, 169.3 mmol), EDCl (17.85 g, 93.11 mmol) and finally DMAP (1.03 g, 8.46 mmol). The reaction mixture was warmed to RT and stirred for 18 h.

The DMF was removed in vacuo to give a yellow oil. This was partitioned between water and EtOAc. The organic phase was dried (MgSO₄) and concentrated in vacuo. The crude extract was purified by column chromatography (25% EtOAC in heptane) to yield the desired product as a clear oil. This was used directly in the next stage without characterization.

Stage 2—Cbz Deprotection to Yield Cyclopentyl O-tert-butyl-L-serinate (Intermediate D)

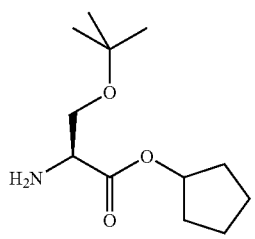 [SMILES: CC(C)(C)OC[C@H](N)C(=O)OC1CCCC1]

Stage 1 product was dissolved in EtOAc (150 mL), treated with Pd(OH)₂ (10 mol %) and stirred under an atmosphere of hydrogen for 32 h. Upon completion, the catalyst was removed by filtration through celite and the filtrate concentrated in vacuo to yield the desired product as a clear oil (15.96 g, 82% over two steps). ¹H NMR (300 MHz, d₆-DMSO) δ: 5.17 (1H, t), 3.45 (1H, m), 3.34 (2H, q), 1.90-1.50 (9H, br m), 1.08 (9H, s).

Preparation of O-(1-isobutoxyethyl)hydroxylamine (Intermediate E)

Scheme 2

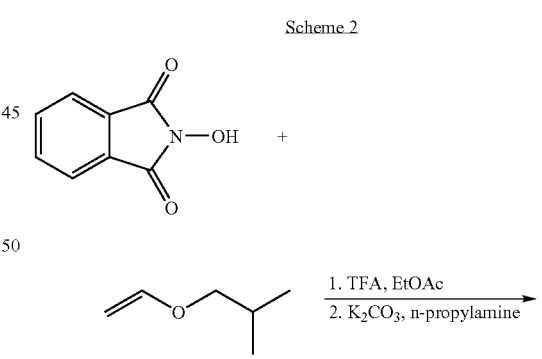

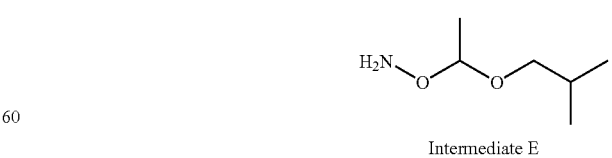

Intermediate E

Intermediate E was prepared following the methodology described in WO 01/60785. ¹H NMR (300 MHz, d₆-DMSO) δ: 0.85 (6H, d), 1.15 (3H, d), 1.75 (1H, m), 3.18 (1H, dd), 3.42 (1H, dd), 4.53 (1H, q), 5.82 (2H, s).

Preparation of Ethyl 2-(methylsulfonyl)pyrimidine-5-carboxylate (Intermediate F)

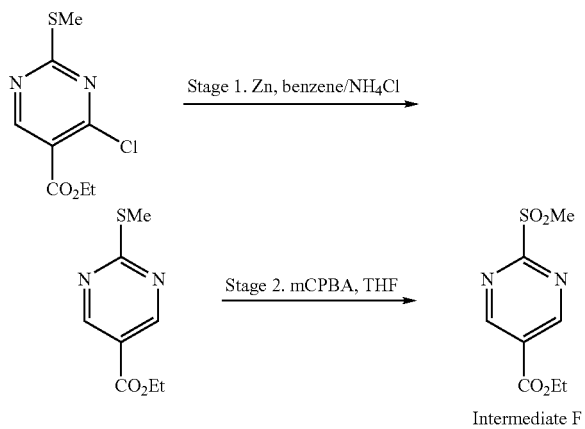

Stage 1—Chloro Reduction

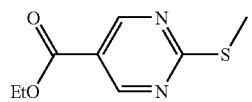

Ethyl 4-chloro-2-methylthio-5-pyrimidine carboxylate (12.5 g, 53.88 mmol) and Zn powder (14.1 g, 215.52 mmol) were combined and benzene (60 mL) and 3M NH$_4$Cl (140 mL) were added. The suspension was stirred vigorously and heated to 80° C. for 30 h. The reaction mixture was filtered through celite and washed with EtOAc (200 mL). The filtrate was concentrated in vacuo to about 50 mL and then partitioned between H$_2$O (400 mL) and EtOAc (400 mL). The aqueous layer was further extracted with EtOAc (250 mL). The combined organic layers were dried (MgSO$_4$) and concentrated in vacuo to a dark oil. This was purified by column chromatography (neat heptane followed by 1:1:1 heptane/CH$_2$Cl$_2$/Et$_2$O and finally 2:2:0.5 heptane/CH$_2$Cl$_2$/Et$_2$O). The desired product was obtained as a colourless oil (13 g, 61%). m/z=199 [M+H]$^+$, $^1$H NMR (300 MHz, d$_6$-DMSO) δ: 1.30 (3H, t), 2.60 (3H, s), 4.35 (2H, q), 9.0 (2H, s).

Stage 2—Sulfide Oxidation to Yield Ethyl 2-(methylsulfonyl)pyrimidine-5-carboxylate (Intermediate F)

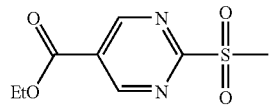

To a stirred solution of stage 1 product (13 g, 47.59 mmol) in dry THF (250 mL) was slowly added over 30 minutes a solution of mCPBA (47.59 g, 275.76 mmol) in THF (150 mL) at 0° C. under N$_2$. The reaction mixture was allowed to warm to RT and stirred for 2 h. The reaction mixture was then concentrated in vacuo to about 100 mL and the product/benzoic acid mixture pre-absorbed onto silica gel. Purification was achieved via column chromatography (neat hexane initially, then 1:5:3 CH$_2$Cl$_2$/heptane/Et$_2$O, followed by 1:1:1 CH$_2$Cl$_2$/heptane/Et$_2$O). The desired compound was obtained as a white solid (10 g, 66%). m/z=231 [M+H]$^+$, $^1$H NMR (300 MHz, d$_6$-DMSO) δ: 1.40 (3H, t), 3.50 (3H, s), 4.40 (2H, q), 9.50 (2H, s).

Preparation of 3-azabicyclo[3.1.0]hex-6-ylmethanol (Intermediate G)

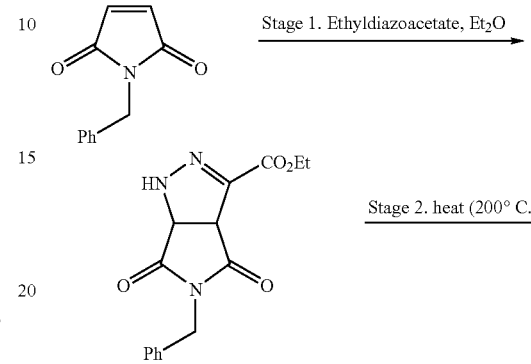

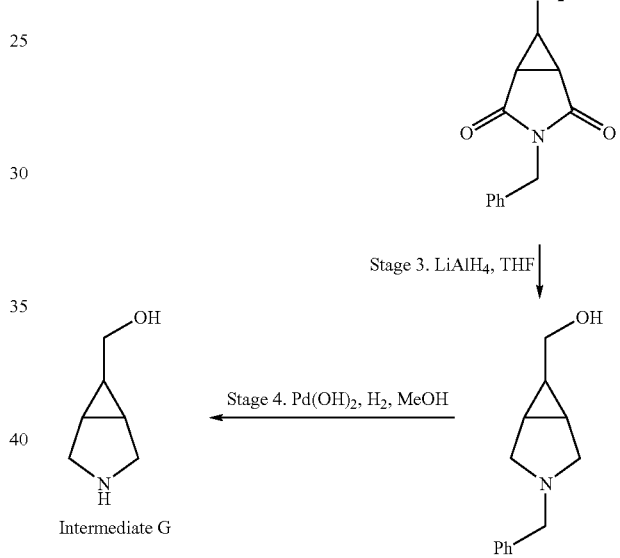

Stage 1—Diels Alder Reaction

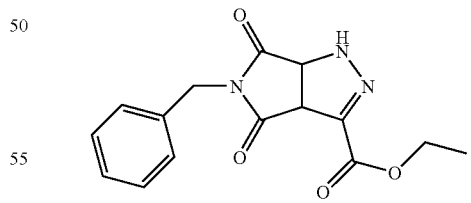

N-Benzylmaleimide (50 g, 267.1 mmol) was dissolved in Et$_2$O (600 mL), treated with ethyldiazoacetate (31 mL, 293.8 mmol) and stirred at RT under nitrogen atmosphere for 36 h. A white precipitate had formed so it was isolated by filtration, washed with ice-cold Et$_2$O and dried to give the desired compound as a white solid (72 g, 89%). m/z=302 [M+H]$^+$, $^1$H NMR (300 MHz, d$_6$-DMSO) δ: 1.20 (3H, t), 4.15 (2H, q), 4.55 (2H, s), 4.60 (1H, d), 5.00 (1H, d), 7.15-7.35 (5H, m), 9.60 (1H, s).

Stage 2—Condensation

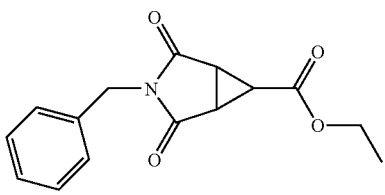 [SMILES: CCOC(=O)C1C2C(=O)N(Cc3ccccc3)C(=O)C12]

Stage 1 product (72 g, 239.2 mmol) was heated to 160° C. until it melted to a yellow oil. The oil was heated further to 200° C. and bubbling started. The oil was heated at 200° C. for 30 minutes until the bubbling had subsided. The now amber-coloured oil was cooled to RT and triturated with ice-cold $Et_2O$. The resulting precipitate was filtered and washed with more ice-cold $Et_2O$ to give the product as a cream solid (37.2 g, 57%). $^1$H NMR (300 MHz, $d_6$-DMSO) δ: 1.20 (3H, t), 2.80 (1H, t), 3.00 (2H, d), 4.15 (2H, q), 4.35 (2H, s), 7.20-7.40 (5H, m).

Stage 3—Reduction

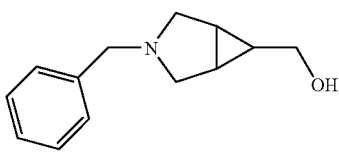 [SMILES: OCC1C2CN(Cc3ccccc3)CC12]

Stage 2 product (37.2 g, 136.3 mmol) was dissolved in dry THF (400 mL). This solution was added dropwise at 0° C. to a suspension of $LiAlH_4$ (20.7 g, 545.3 mmol) in dry THF (200 mL). The resulting brown suspension was heated to 60° C. under nitrogen atmosphere for 36 h. The mixture was then cooled to 0° C. and quenched carefully with saturated $NH_4Cl_{aq}$. A grey solid formed and more THF was added to allow adequate stirring. Solid $Na_2SO_4$ was added to the mixture which was stirred at RT for 30 minutes. The mixture was then filtered through celite to give a pale yellow solution. This was concentrated in vacuo to give the desired product as an orange oil (14.1 g, 51%). m/z=204 [M+H]$^+$, $^1$H NMR (300 MHz, $d_6$-DMSO) δ: 2.25 (2H, d), 2.85 (2H, d), 3.20 (2H, t), 3.55 (2H, s), 4.35 (1H, t), 7.20-7.40 (5H, m).

Stage 4—Nitrogen Deprotection to Yield 3-azabicyclo[3.1.0]hex-6-ylmethanol (Intermediate G)

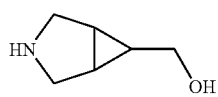

Stage 3 product (7.5 g, 37.0 mmol) was dissolved in dry MeOH (250 mL) at RT. $Pd(OH)_2$ (1.5 g) was added to the solution and the reaction fitted with a hydrogen balloon. The reaction was degassed twice and flushed with $H_2$. The reaction was allowed to stir for 6 h and flushed with a fresh hydrogen balloon and allowed to stir for a further 64 h. The reaction mixture was then filtered through celite. The solvent was removed in vacuo and the residue dried to give the product as a white solid (4.1 g, 98%). m/z=114 [M+H]$^+$, $^1$H NMR (300 MHz, $CDCl_3$) δ: 0.94 (1H, septet, J=3.3 Hz), 1.37 (2H, m), 2.89 (2H, d, J=11.4 Hz), 3.02 (2H, d, J=11.4 Hz), 3.54 (2H, d, J=6.9 Hz).

Example 1

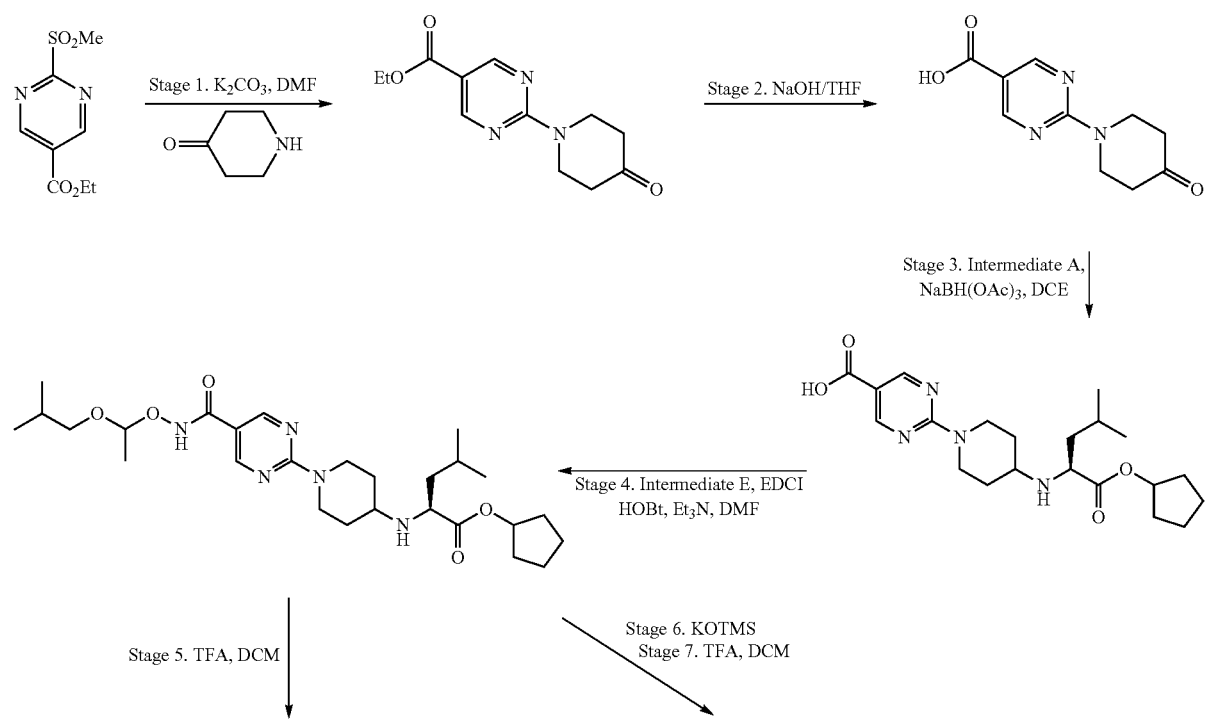

Scheme 5

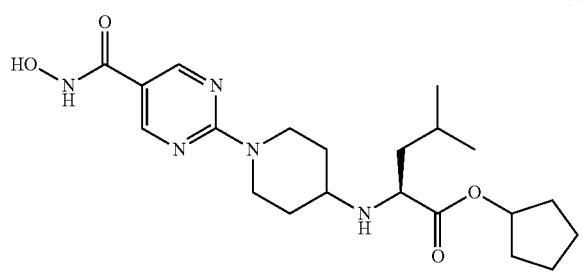

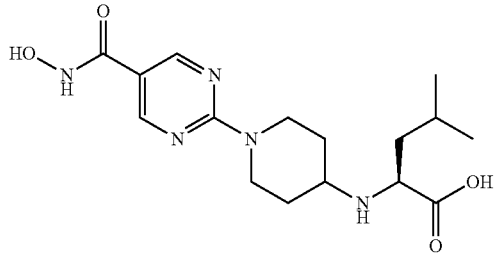

Compounds Prepared:

FIG. 2

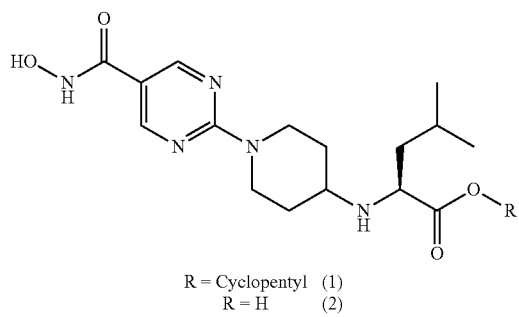

R = Cyclopentyl (1)
R = H (2)

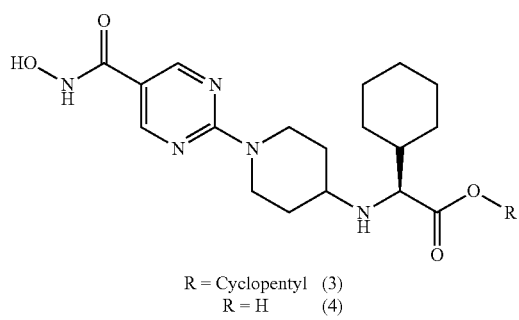

R = Cyclopentyl (3)
R = H (4)

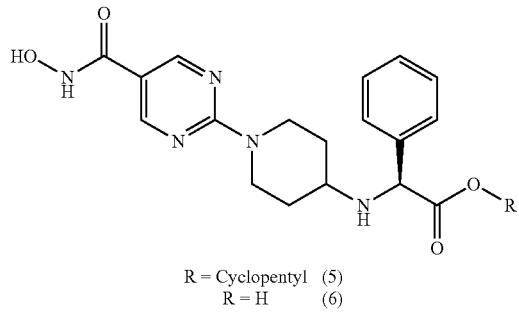

R = Cyclopentyl (5)
R = H (6)

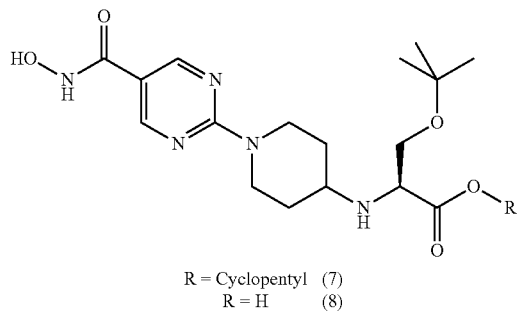

R = Cyclopentyl (7)
R = H (8)

-continued

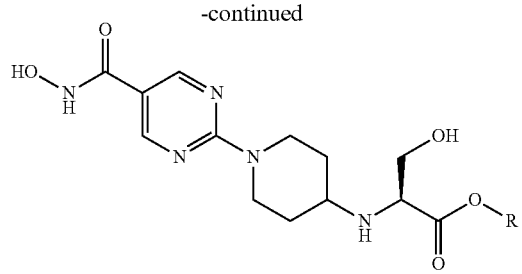

R = Cyclopentyl (9)

Synthesis of Compounds Outlined in FIG. 2 Exemplified for (1) and (2)

Stage 1—Coupling

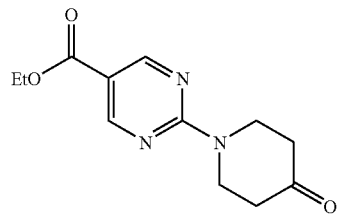 [SMILES: CCOC(=O)c1cnc(N2CCC(=O)CC2)nc1]

A suspension of piperidine-4-one HCl salt (1.16 g, 8.5 mmol) and $K_2CO_3$ (11.70 g, 85.0 mmol) was stirred in DMF (50 mL) at RT under a nitrogen atmosphere for 10 minutes. Intermediate F (1.97 g, 8.5 mmol) was then added and stirring continued for a further 10 minutes. The reaction was then diluted with water (150 mL) and extracted with EtOAc (2×200 mL). The combined organic layers were dried ($MgSO_4$) and the solvent removed in vacuo to give the product as a yellow solid which was used in the next step without further purification. m/z=250 [M+H]$^+$.

Stage 2—Ester Hydrolysis

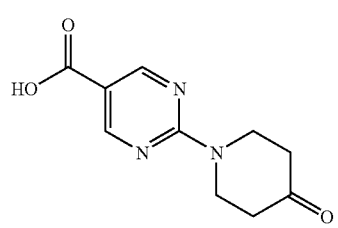 [SMILES: O=C1CCN(c2ncc(C(=O)O)cn2)CC1]

Stage 1 product was stirred in 1M NaOH$_{aq}$ (30 mL) and THF (30 mL) at RT for 4 days. The reaction was then acidified to pH ~3 with 1M HCl$_{aq}$ and this was extracted with DCM (2×200 mL). The combined organic layers were dried (Na$_2$SO$_4$) and the solvent removed in vacuo to give the product as a yellow solid, (665 mg, 35% over 2 steps). m/z=222 [M+H]$^+$.

Stage 3—Reductive Amination

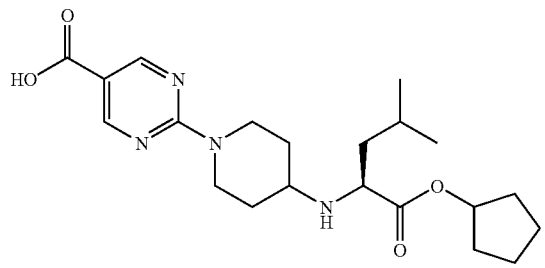 [SMILES: CC(C)C[C@H](NC1CCN(c2ncc(C(=O)O)cn2)CC1)C(=O)OC1CCCC1]

Stage 2 product (100 mg, 0.45 mmol) was stirred in DCE (10 mL) with intermediate A (106 mg, 0.45 mmol) and NaBH(OAc)$_3$ (142 mg, 0.67 mmol) at RT under a nitrogen atmosphere for 3 days. The reaction was then diluted with water (50 mL) and extracted with DCM (2×100 mL). The combined organic layers were dried (Na$_2$SO$_4$) and the solvent removed in vacuo to give the product as a yellow solid which was used in the next step without further purification. m/z=405 [M+H]$^+$.

Stage 4—Protected Hydroxamate Formation

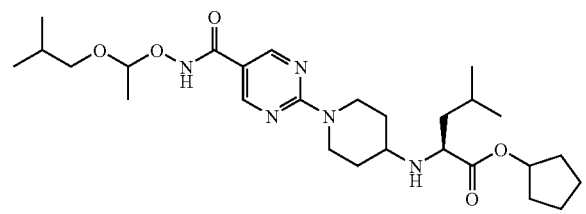 [SMILES: CC(C)COC(C)ONC(=O)c1cnc(N2CCC(N[C@@H](CC(C)C)C(=O)OC3CCCC3)CC2)nc1]

Stage 3 product (182 mg, 0.45 mmol) was stirred in DMF (10 mL) with EDCl (103 mg, 0.54 mmol), HOBt (73 mg, 0.54 mmol), Et$_3$N (314 µL, 2.25 mmol) and intermediate E (310 µL, 2.25 mmol) for 16 h at RT under a nitrogen atmosphere. The reaction was then diluted with water (50 mL) and extracted with DCM (2×100 mL). The combined organic layers were then dried (MgSO$_4$) and the solvent removed in vacuo. The residue was purified by column chromatography (0 to 15% MeOH in DCM) to give the product as a yellow oil (110 mg, 47%). m/z=520 [M+H]$^+$.

Stage 5—Hydroxamate Deprotection to Yield Cyclopentyl N-{1-[5-(hydroxycarbamoyl)pyrimidin-2-yl]piperidin-4-yl}-L-leucinate (1)

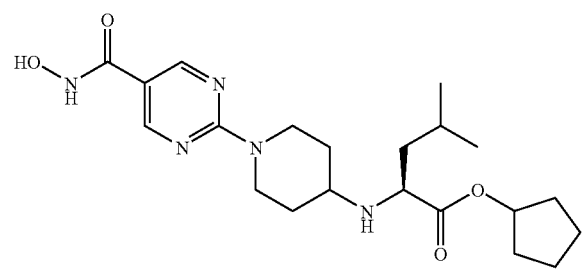 [SMILES: CC(C)C[C@H](NC1CCN(c2ncc(C(=O)NO)cn2)CC1)C(=O)OC1CCCC1]

Stage 4 product (110 mg, 0.21 mmol) was stirred in DCM (20 mL) with TFA (0.5 mL) for 1 h at RT. The solvent was then removed in vacuo and the residue purified by preparative HPLC to give the product as a purple solid (12 mg, 11%). LCMS purity 99%, m/z=420 [M+H]$^+$, $^1$H NMR (300 MHz, CD$_3$OD) δ: 0.91 (6H, m), 1.46-1.84 (13H, m), 2.05 (2H, m), 2.90 (2H, m), 3.42 (2H, m), 4.01 (1H, m), 4.91 (1H, m), 5.27 (1H, m), 8.58 (2H, m).

Stage 6—Ester Hydrolysis

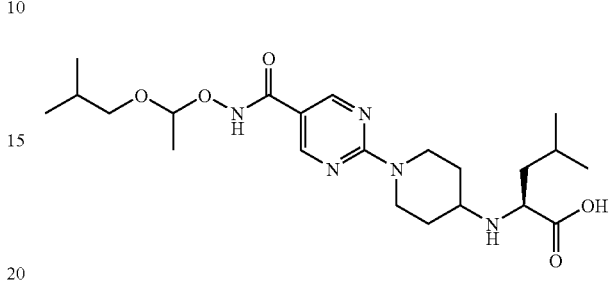

Stage 4 product (182 mg, 0.45 mmol) was stirred in THF (10 mL) with KOTMS (115 mg, 0.9 mmol) for 4 days at RT under a nitrogen atmosphere. After this time the solvent was removed in vacuo and the residue used in the next step without further purification. m/z=452 [M+H]+.

Stage 7—Hydroxamate Deprotection to Yield N-{1-[5-(hydroxycarbamoyl)pyrimidin-2-yl]piperidin-4-yl}-L-leucine (2)

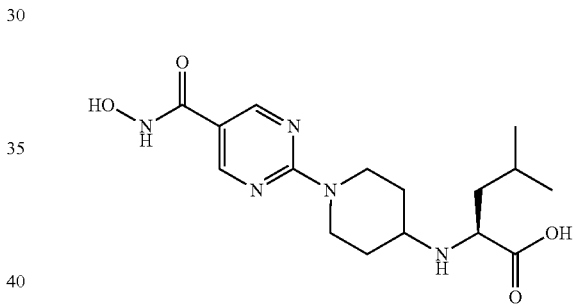

Stage 6 product (0.45 mmol) was stirred in DCM (10 mL) with TFA (1 mL) at RT for 30 minutes. The solvent was then removed in vacuo and the residue purified by preparative HPLC to give the product as a pink solid (7 mg, 5% over two steps). LCMS purity 95%, m/z=352 [M+H]$^+$, insoluble in NMR solvents.

The analogues outlined in FIG. 2 were prepared by the procedure described for (1) and (2). Data for each analogue is given.

(3)

LCMS purity 97%, m/z=440 [M+H]$^+$, $^1$H NMR (300 MHz, CD$_3$OD) δ: 1.30-1.61 (9H, m), 1.78-1.90 (4H, m), 2.23 (2H, m), 2.90 (2H, m), 5.00 (1H, m), 5.33 (1H, m), 7.53 (5H, m), 8.69 (2H, s).

(4)

LCMS purity 98%, m/z=378 [M+H]$^+$, insoluble in NMR solvents.

(5)

LCMS purity 97%, m/z=446 [M+H]$^+$, $^1$H NMR (300 MHz, CD$_3$OD) δ: 0.80-1.82 (24H, m), 2.04 (2H, m), 2.94 (2H, m), 4.86 (1H, m), 5.23 (1H, m), 8.58 (2H, s).

(6)

LCMS purity 95%, m/z=372 [M+H]$^+$, $^1$H NMR (300 MHz, CD$_3$OD) δ: 1.20 (2H, m), 1.50 (2H, m), 2.15 (2H, m), 2.80 (3H, m), 4.88 (1H, m), 7.37-7.46 (5H, m), 8.56 (2H, s).

(7)
LCMS purity 98%, m/z=450 [M+H]$^+$, $^1$H NMR (300 MHz, CD$_3$OD) δ: 1.25 (9H, s), 1.58-1.77 (8H, br m), 1.96 (2H, m), 2.22 (2H, m), 3.02 (2H, m), 3.55 (1H, m), 3.87 (1H, dd, J=10.8, 2.7 Hz), 3.99 (1H, dd, J=10.8, 2.7 Hz), 4.45 (1H, m), 5.03 (2H, m), 5.35 (1H, m), 8.70 (2H, s).
(8)
LCMS purity 98%, m/z=382 [M+H]$^+$, $^1$H NMR (300 MHz, CD$_3$OD) δ: 1.25 (9H, s), 1.65 (2H, m), 2.25 (2H, m), 3.01 (2H, t, J=13.2 Hz), 3.57 (1H, m), 3.91 (1H, dd, J=10.5, 2.7 Hz), 4.00 (1H, dd, J=10.5, 2.7 Hz), 4.38 (1H, m), 5.05 (2H, m), 8.70 (2H, s).
(9)
LCMS purity 95%, m/z=394 [M+H]$^+$, $^1$H NMR (300 MHz, CD$_3$OD) δ: 1.52-1.98 (11H, m), 2.10 (2H, m), 2.87 (3H, m), 3.44 (1H, m), 3.95 (2H, m), 4.18 (1H, m), 5.25 (1H, m), 8.58 (2H, m).
Example 2
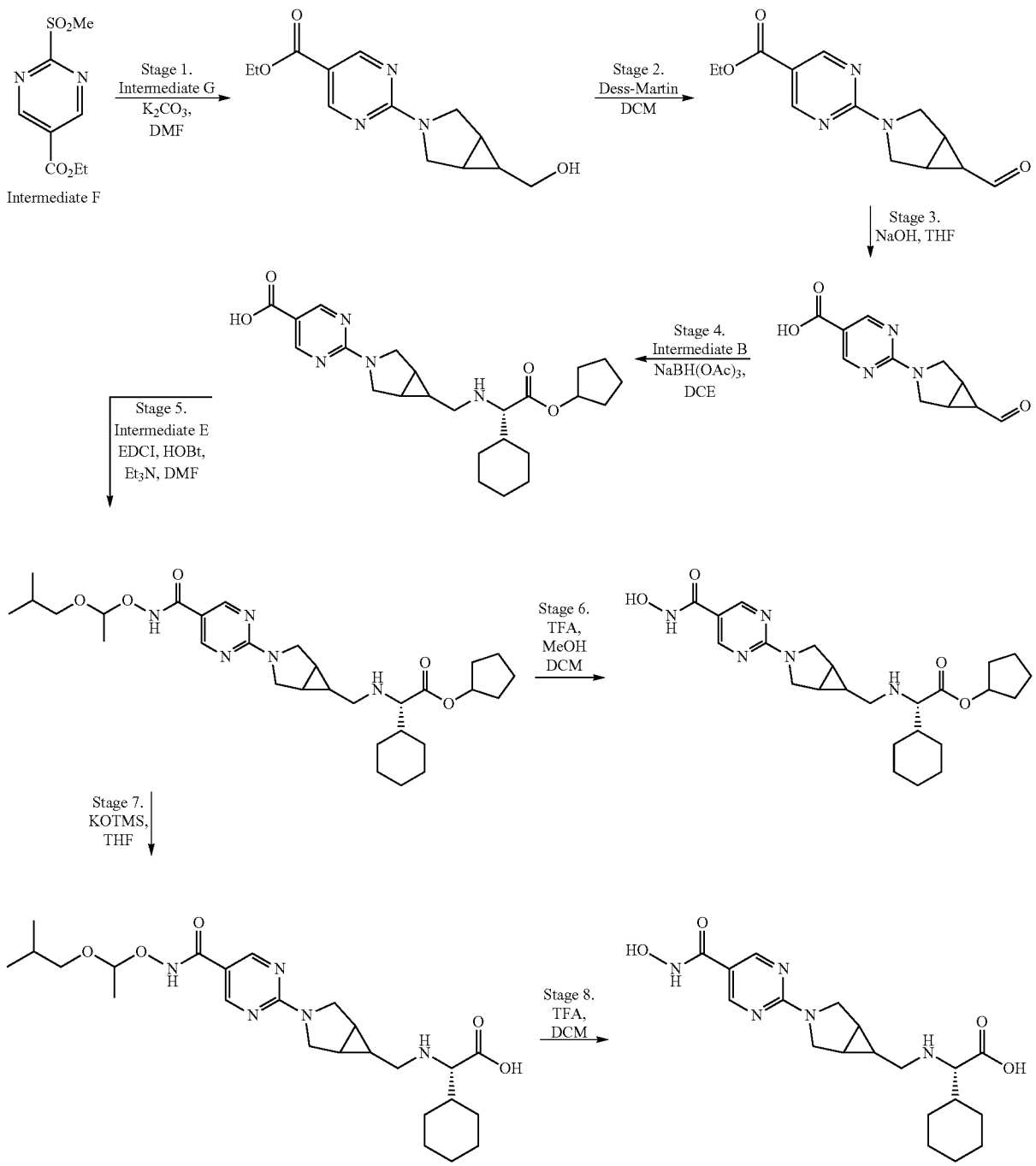
Scheme 6

Compounds Prepared:

FIG. 3

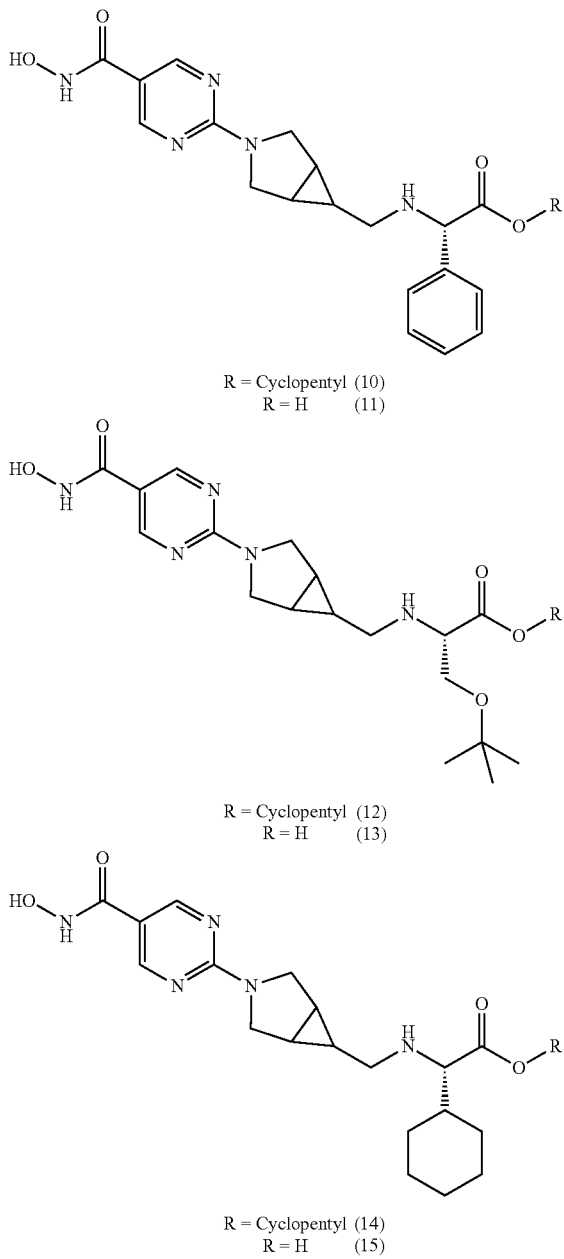

R = Cyclopentyl (10)
R = H (11)

R = Cyclopentyl (12)
R = H (13)

R = Cyclopentyl (14)
R = H (15)

Synthesis of Compounds Outlined in FIG. 3 Exemplified for (14) and (15)

Stage 1—Coupling

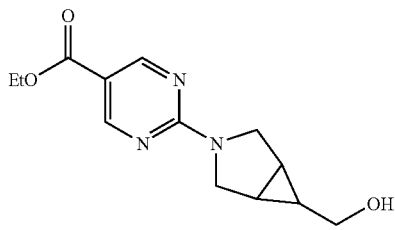 [SMILES: CCOC(=O)c1cnc(N2CC3C(CO)C3C2)nc1]

Intermediate G (0.97 g, 8.62 mmol) was stirred in DMF (20 mL) and MeCN (20 mL) with $K_2CO_3$ (5.96 g, 43.10 mmol) at RT under a nitrogen atmosphere for 10 minutes. Intermediate F (2.00 g, 8.62 mmol) was then added and the reaction allowed to stir for a further 20 minutes. The reaction was then diluted with water (100 mL) and extracted with EtOAc (2×100 mL). The combined organic layers were dried ($MgSO_4$) and the solvent removed in vacuo to give the product as a light yellow solid which was used in the next step without further purification (1.8 g, 78%). m/z=264 $[M+H]^+$.

Stage 2—Alcohol Oxidation

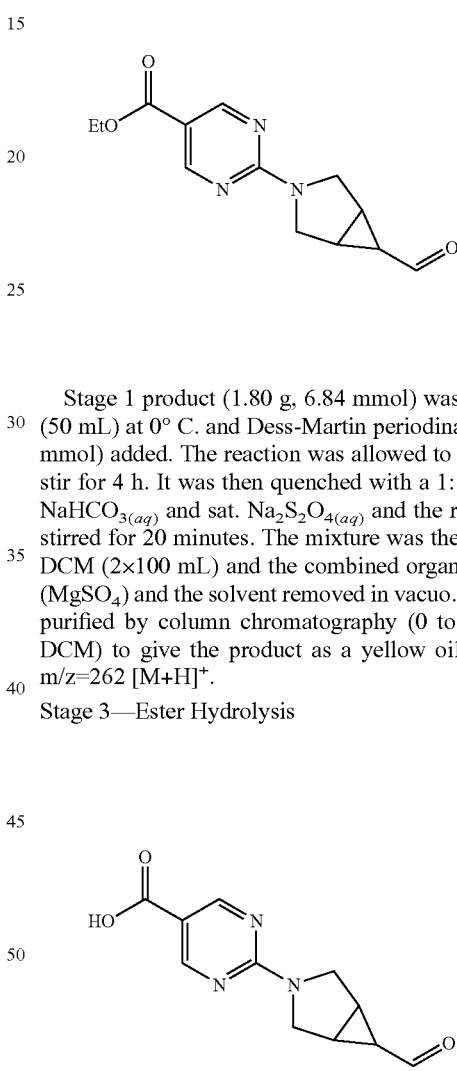

Stage 1 product (1.80 g, 6.84 mmol) was stirred in DCM (50 mL) at 0° C. and Dess-Martin periodinane (3.50 g, 8.22 mmol) added. The reaction was allowed to warm to RT and stir for 4 h. It was then quenched with a 1:1 mixture of sat. $NaHCO_{3(aq)}$ and sat. $Na_2S_2O_{4(aq)}$ and the resulting mixture stirred for 20 minutes. The mixture was then extracted with DCM (2×100 mL) and the combined organic extracts dried ($MgSO_4$) and the solvent removed in vacuo. The residue was purified by column chromatography (0 to 10% MeOH in DCM) to give the product as a yellow oil (1.35 g, 72%). m/z=262 $[M+H]^+$.

Stage 3—Ester Hydrolysis

Stage 2 product (1.35 g, 5.17 mmol) was stirred in 1M $NaOH_{aq}$ (20 mL) and THF (20 mL) at RT for 3 h. The reaction was then acidified to pH ~3 with 1M $HCl_{aq}$ which caused a white solid to precipitate out. This solid was filtered off and dried and retained. The filtrate was then extracted with DCM (2×100 mL) and the combined organic layers dried ($Na_2SO_4$) and the solvent removed in vacuo to give a light yellow solid which was combined with the previously obtained solid (990 mg, 82%). m/z=236 $[M+H]^+$.

Stage 4—Reductive Amination

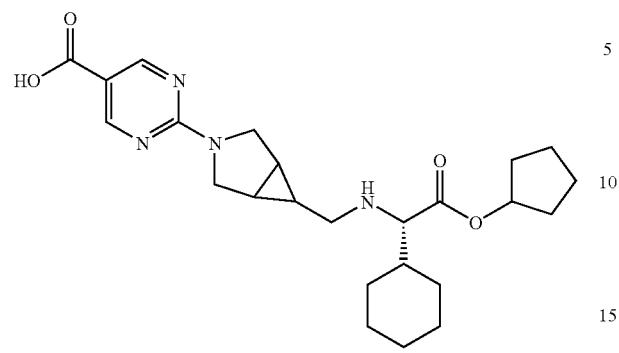

Stage 3 product (175 mg, 0.75 mmol) was stirred in DCE (10 mL) with intermediate B (196 mg, 0.75 mmol) and NaBH(OAc)$_3$ (222 mg, 1.05 mmol) at RT under a nitrogen atmosphere for 16 h. The reaction was then diluted with H$_2$O (50 mL) and extracted with Et$_2$O. The combined organic layers were dried (Na$_2$SO$_4$) and the solvent removed in vacuo to give the desired product as a yellow oil which was used in the next step without further purification (171 mg, 52%). m/z=443 [M+H]$^+$.

Stage 5—Protected Hydroxamate Formation

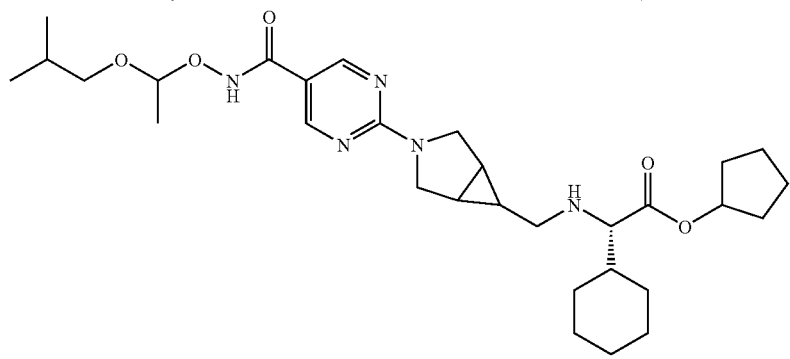

Stage 4 product (171 mg, 0.39 mmol) was stirred in DMF (10 mL) with intermediate E (539 µL, 3.9 mmol), EDCl (90 mg, 0.47 mmol), HOBt (63 mg, 0.47 mmol) and Et$_3$N (543 µL, 3.9 mmol) at RT under a nitrogen atmosphere for 16 h. The reaction was then diluted with H$_2$O (50 mL) and extracted with DCM (2×100 mL). The combined organic layers were dried (MgSO$_4$) and the solvent removed in vacuo. The residue was purified by column chromatography (0 to 10% MeOH in DCM) to give the product as a colourless oil (91 mg, 42%). m/z=558 [M+H]$^+$.

Stage 6—Hydroxamate Deprotection to Yield Cyclopentyl (2S)-cyclohexyl[({3-[5-(hydroxycarbamoyl)pyrimidin-2-yl]-3-azabicyclo[3.1.0]hex-6-yl}methyl)amino]acetate (14)

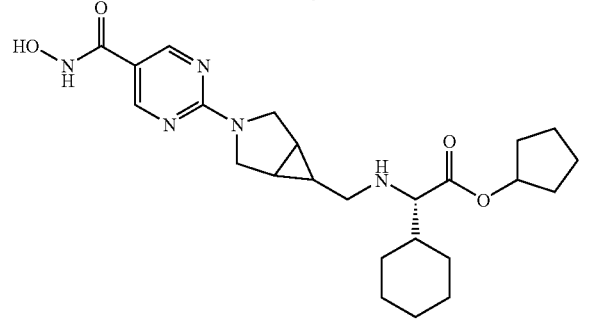 [SMILES: O=C(NO)c1cnc(N2CC3C(CN[C@H](C(=O)OC4CCCC4)C4CCCCC4)C3C2)nc1]

Stage 5 product (91 mg, 0.163 mmol) was stirred in 1:1 MeOH/DCM (4 mL) with TFA (2 mL) at RT for 1 h. The solvent was then removed in vacuo and the residue purified by preparative HPLC to give the desired product as a white solid (15 mg, 20%). LCMS purity 98%, m/z=558 [M+H]$^+$, $^1$H NMR (300 MHz, CD$_3$OD) δ: 0.92-1.38 (6H, m), 1.73-1.95 (16H, m), 3.09 (2H, m), 3.62 (2H, d, J=11.4 Hz), 3.91 (1H, d, J=3.6 Hz), 4.00 (2H, d, J=11.4 Hz), 5.51 (1H, m), 8.67 (2H, s).

Stage 7—Ester Hydrolysis

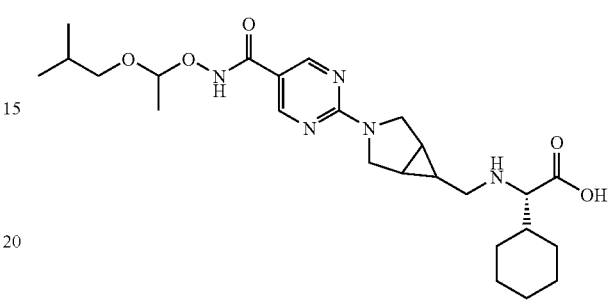

Stage 5 product (161 mg, 0.29 mmol) was stirred in THF (10 mL) with KOTMS (74 mg, 0.58 mmol) at RT under a nitrogen atmosphere for 48 h. More KOTMS (112 mg, 0.87 mmol) was then added and the reaction stirred at 50° C. for 48 h. The solvent was then removed in vacuo and the residue used in the next step without further purification. m/z=490 [M+H]$^+$.

Stage 8—Hydroxamate Deprotection to Yield (2S)-cyclohexyl[({3-[5-(hydroxycarbamoyl)pyrimidin-2-yl]-3-azabicyclo[3.1.0]hex-6-yl}methyl)amino]acetic acid (15)

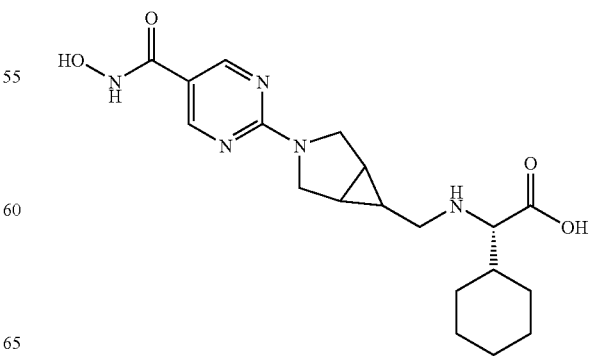

Stage 7 product (0.29 mmol) was stirred in DCM (10 mL) with TFA (1 mL) at RT for 30 minutes. The solvent was then removed in vacuo and the residue purified by preparative HPLC to give the product as a white solid (13 mg, 12%). LCMS purity 99%, m/z=390 [M+H]$^+$, $^1$H NMR (300 MHz, CD$_3$OD) δ: 0.96 (1H, m), 1.10-1.47 (6H, m), 1.72-1.87 (6H, m), 1.99 (1H, m), 2.99 (1H, m), 3.18 (1H, m), 3.63 (2H, dd, J=11.7, 3.3 Hz), 3.85 (1H, d, J=3.3 Hz), 3.99 (2H, d, J=11.7 Hz), 8.67 (2H, s).

The analogues outlined in FIG. 3 were prepared by the procedure described for (14) and (15). Data for each analogue is given.

(10)

LCMS purity 95%, m/z=452 [M+H]$^+$, $^1$H NMR (300 MHz, CD$_3$OD) δ: 1.41-1.64 (6H, m), 1.72-1.93 (5H, m), 2.88 (2H, m), 3.60 (2H, m), 3.97 (2H, d, J=10.5 Hz), 5.26 (1H, s), 5.32 (1H, m), 7.51 (5H, m), 8.67 (2H, s).

(11)

LCMS purity 97%, m/z=384 [M+H]$^+$, $^1$H NMR (300 MHz, CD$_3$OD) δ: 0.94 (1H, m), 1.83 (2H, m), 3.01 (2H, d, J=7.5 Hz), 3.62 (2H, m), 3.96 (2H, d, J=11.7 Hz), 5.07 (1H, s), 7.53 (5H, m), 8.67 (2H, s).

(12)

LCMS purity 95%, m/z=462 [M+H]$^+$, $^1$H NMR (300 MHz, CD$_3$OD) δ: 0.99 (1H, m), 1.24 (9H, s), 3.11 (2H, dd, J=7.5, 2.4 Hz), 3.63 (2H, dd, J=12.0, 3.1 Hz), 3.91 (2H, ddd, J=24.6, 10.8, 3.3 Hz), 4.01 (2H, d, J=11.7 Hz), 4.26 (1H, m), 5.35 (1H, m), 8.68 (2H, s).

(13)

LCMS purity 98%, m/z=394 [M+H]$^+$, $^1$H NMR (300 MHz, CD$_3$OD) δ: 1.01 (1H, m), 1.25 (9H, s), 1.88 (2H, m), 3.11 (2H, d, J=7.5 Hz), 3.64 (2H, dd, J=11.7, 3.9 Hz), 3.90 (2H, m), 4.01 (2H, d, J=11.7 Hz), 4.14 (1H, m), 8.67 (2H, s).

Example 3

Scheme 7

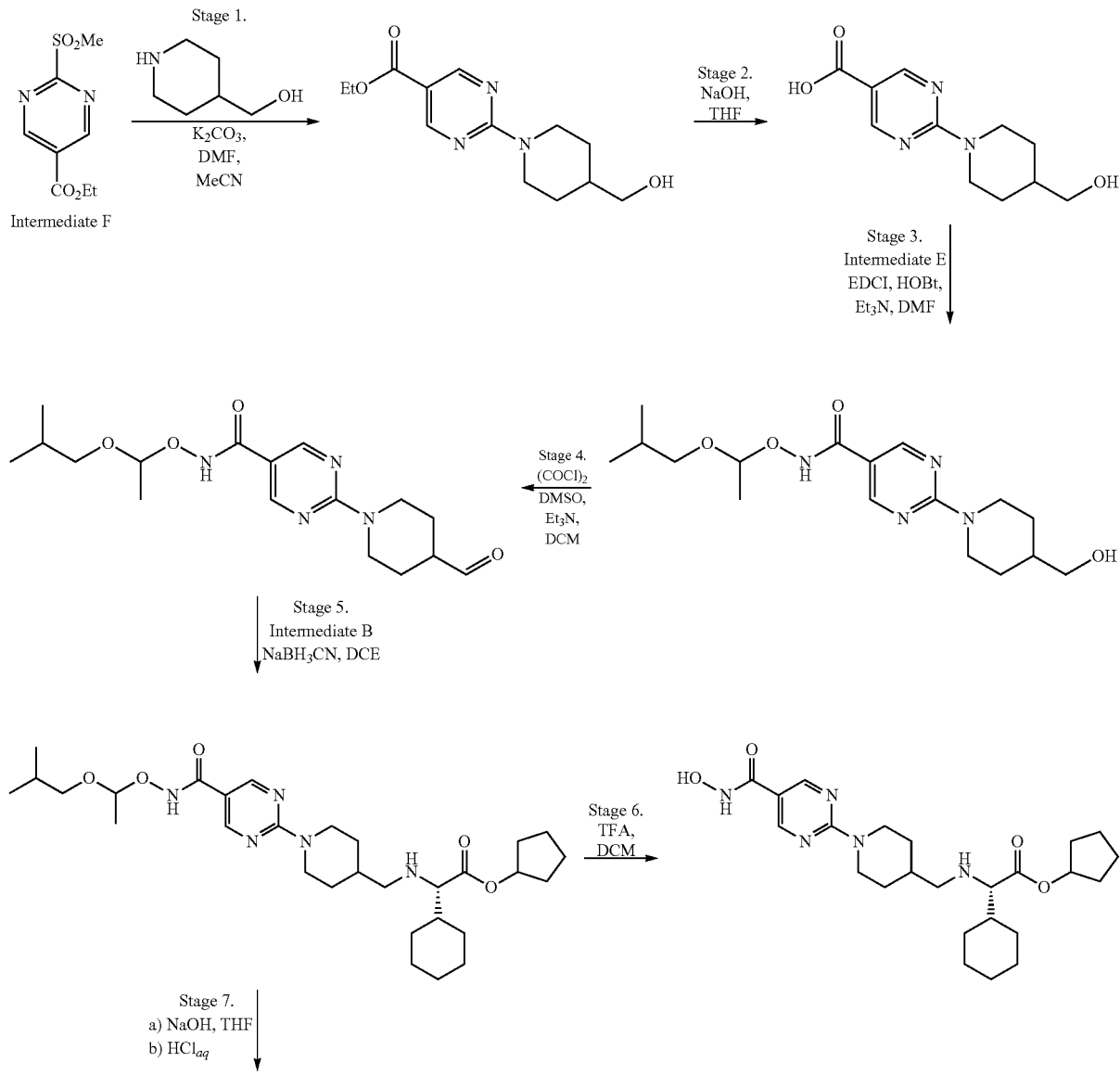

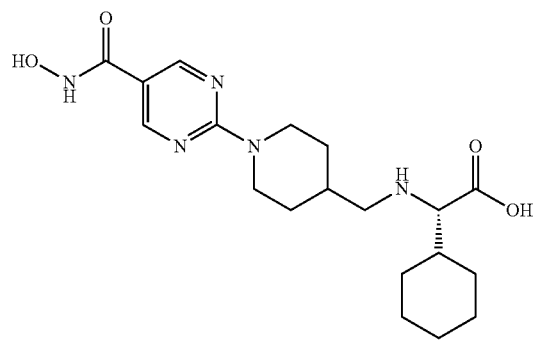
Compounds Prepared:
FIG. 4
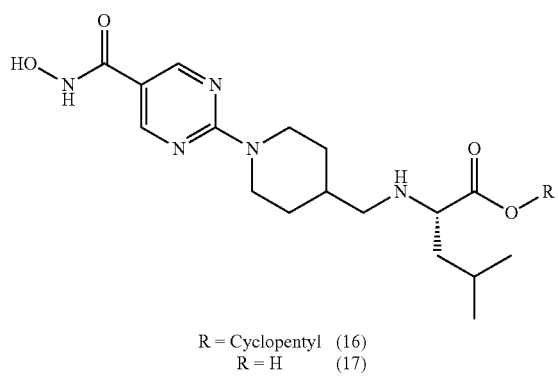
R = Cyclopentyl (16)
R = H (17)
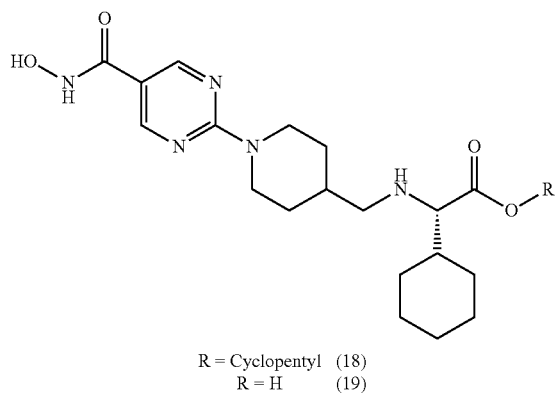
R = Cyclopentyl (18)
R = H (19)
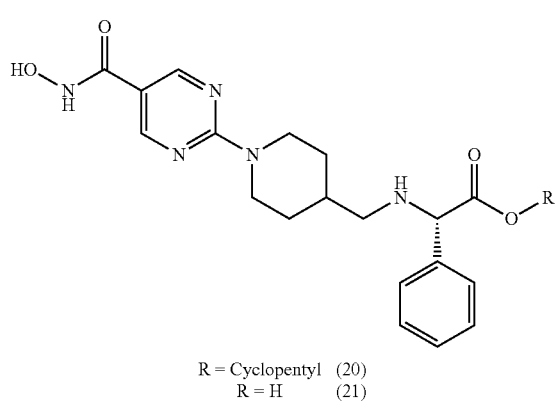
R = Cyclopentyl (20)
R = H (21)
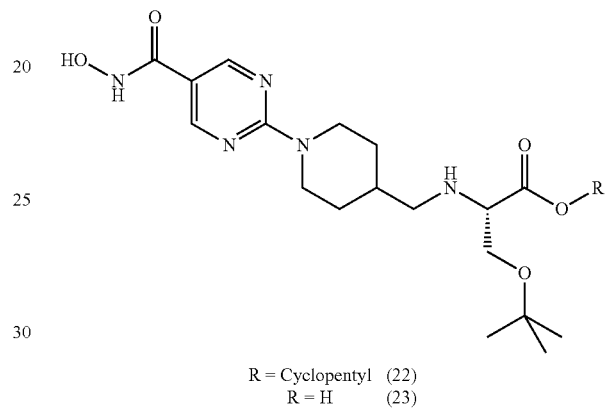
R = Cyclopentyl (22)
R = H (23)
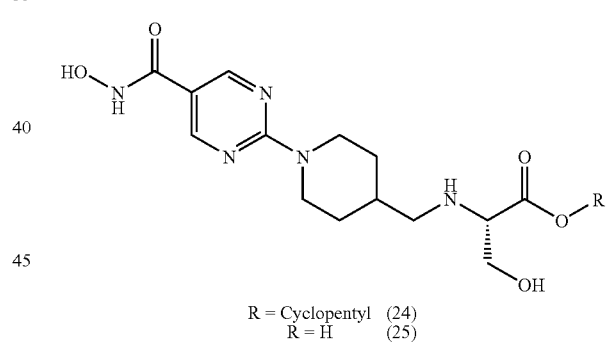
R = Cyclopentyl (24)
R = H (25)
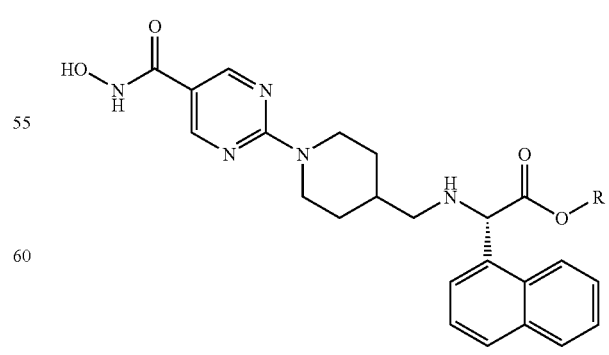
R = Cyclopentyl (26)

Synthesis of Compounds Outlined in FIG. 4 Exemplified for (18) and (19)

Stage 1—Coupling

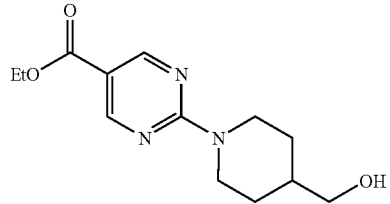 [SMILES: O=C(O)c1cnc(N2CCC(CO)CC2)nc1]

Piperidin-4yl-methanol (2.48 g, 21.55 mmol) was stirred in 1:1 DMF/MeCN (20 mL) with K$_2$CO$_3$ (8.9 g, 64.65 mmol) for 10 minutes at RT under a nitrogen atmosphere. Intermediate F (5 g, 21.55 mmol) was then added and the reaction allowed to stir for 20 minutes. It was then diluted with H$_2$O (100 mL) and extracted with EtOAc (2×100 mL). The combined organic layers were dried (MgSO$_4$) and the solvent removed in vacuo to give the product as an orange solid which was used in the next step without further purification (5.70 g, 99%). m/z=266 [M+H]$^+$.

Stage 2—Ester Hydrolysis

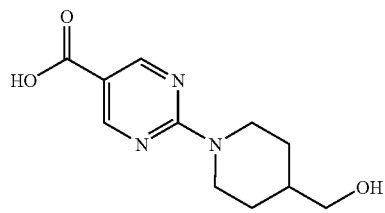

Stage 1 product (5.70 g, 21.51 mmol) was stirred in 1M NaOH$_{aq}$ (20 mL) and THF (20 mL) at RT for 48 h. The reaction was then acidified to pH ~3 with 2M HCl$_{aq}$ causing a solid to precipitate out. This was collected and dried in vacuo to give the product as a white solid (4.47 g, 89%). m/z=238 [M+H]$^+$.

Stage 3—Protected Hydroxamate Formation

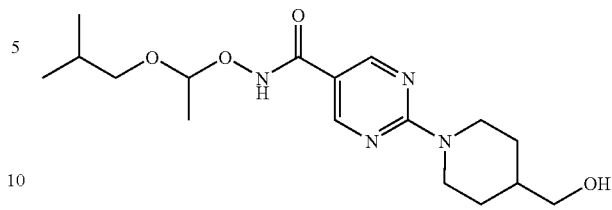

Stage 2 product (4.47 g, 18.86 mmol) was stirred in DMF (50 mL) with intermediate E (13.00 mL, 94.30 mmol), EDCl (4.33 g, 22.60 mmol), HOBt (3.05 g, 22.60 mmol) and Et$_3$N (13.10 mL, 94.30 mmol) at RT under a nitrogen atmosphere for 48 h. The reaction was then diluted with H$_2$O (200 mL) and extracted with DCM (2×200 mL). The combined organic layers were dried (MgSO$_4$) and the solvent removed in vacuo. The residue was purified by column chromatography (0 to 15% MeOH in DCM) to give the product as a yellow oil (5.12 g, 77%). m/z=353 [M+H]$^+$.

Stage 4—Alcohol Oxidation

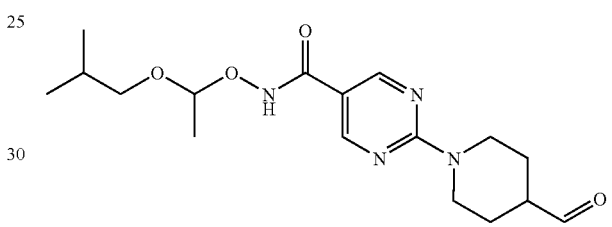

A solution of (COCl)$_2$ (253 µL, 2.90 mmol) in DCM (50 mL) was stirred under a nitrogen atmosphere and cooled to an internal temperature of −70° C. DMSO (363 µL, 5.11 mmol) was then slowly added, maintaining the temperature at −70° C. When the addition was complete, a solution of stage 3 product (1.00 g, 2.84 mmol) in DCM (50 mL) was slowly added, again maintaining the internal temperature at −70° C. When the addition was complete, Et$_3$N (1.70 mL, 12.21 mmol) was slowly added, again maintaining the internal temperature at −70° C. The reaction was allowed to warm to RT and then the solvent was removed in vacuo. The residue was then purified by column chromatography (0 to 10% MeOH in DCM) to give the product as a colourless oil (890 mg, 89%). m/z=351 [M+H]$^+$.

Stage 5—Reductive Amination

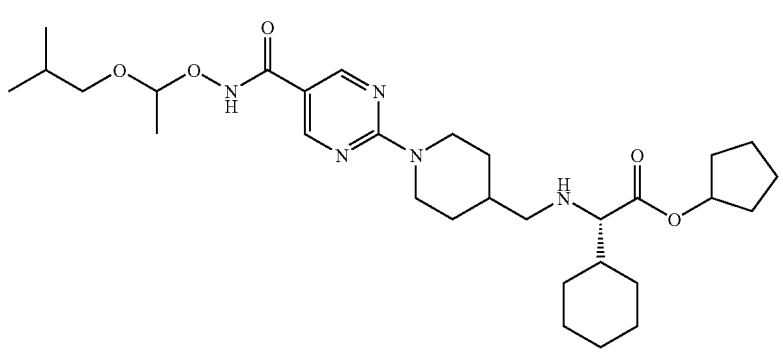 [SMILES: CC(C)COC(C)ONC(=O)c1cnc(N2CCC(CN[C@H](C(=O)OC3CCCC3)C3CCCCC3)CC2)nc1]

Stage 4 product (100 mg, 0.28 mmol) was stirred in DCE (10 mL) with intermediate B (73 mg, 0.28 mmol) and NaBH$_3$CN (35 mg, 0.56 mmol) at RT under a nitrogen atmosphere for 16 h. The reaction was then diluted with H$_2$O (50 mL) and extracted with DCM (2×100 mL). The combined organic layers were dried (MgSO$_4$) and the solvent removed in vacuo. The residue was purified by column chromatography (0 to 10% MeOH in DCM) to give the product as a colourless oil (145 mg, 92%). m/z=560 [M+H]$^+$.

Stage 6—Hydroxamate Deprotection to Yield Cyclopentyl (2S)-cyclohexyl[({1-[5-(hydroxycarbamoyl)pyrimidin-2-yl]piperidin-4-yl}methyl)amino]acetate (18)

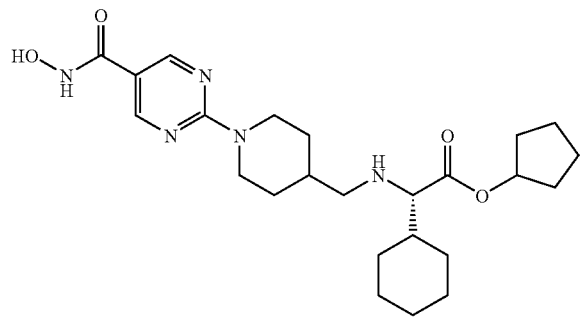 [SMILES: O=C(NO)c1cnc(N2CCC(CN[C@H](C(=O)OC3CCCC3)C3CCCCC3)CC2)nc1]

Stage 5 product (145 mg, 0.26 mmol) was stirred in DCM (10 mL) with TFA (0.5 mL) at RT for 10 minutes. The solvent was then removed in vacuo and the residue purified by preparative HPLC to give the product as a light purple solid (11 mg, 9%). LCMS purity >95%, m/z 460 [M+H]$^+$, $^1$H NMR (300 MHz, CD$_3$OD) δ: 1.02-1.37 (8H, m), 1.73-1.94 (19H, m), 3.02 (3H, m), 3.90 (1H, m), 5.37 (1H, m), 8.67 (2H, s).

Stage 7—Ester Hydrolysis and Hydroxamate Deprotection to Yield (2S)-cyclohexyl[({1-[5-(hydroxycarbamoyl)pyrimidin-2-yl]piperidin-4-yl}methyl)amino]acetic acid (19)

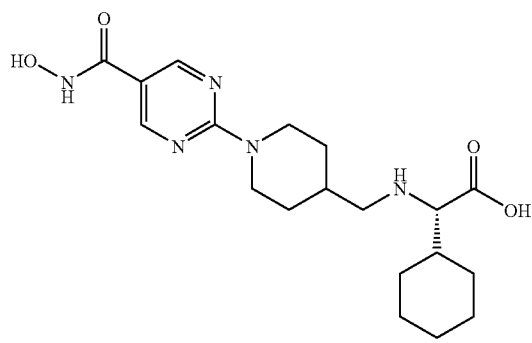 [SMILES: O=C(NO)c1cnc(N2CCC(CN[C@H](C(=O)O)C3CCCCC3)CC2)nc1]

Stage 5 product (78 mg, 0.14 mmol) was stirred in 1M NaOH$_{aq}$ (10 mL) and THF (10 mL) for 4 days at 40° C. After this time the reaction was cooled to RT and acidified to pH ~3 with 1M HCl$_{aq}$. This mixture was stirred for 10 minutes and then evaporated to dryness. The residue was purified by preparative HPLC to give the product as a white solid (1 mg, 2%). LCMS purity 98%, m/z=392 [M+H]$^+$, $^1$H NMR (300 MHz, CD$_3$OD) δ: 1.03-1.25 (9H, m), 1.60-1.87 (8H, m), 2.06 (1H, m), 2.85 (4H, m), 3.44 (1H, m), 8.55 (2H, s).

The analogues outlined in FIG. 4 were prepared by the procedure described for (18) and (19). Data for each analogue is given.

(16)
LCMS purity 98%, m/z=434 [M+H]$^+$, $^1$H NMR (300 MHz, CD$_3$OD) δ: 1.03 (6H, m), 1.32 (4H, m), 1.71-1.95 (15H, m), 2.90 (1H, m), 3.01 (2H, m), 4.01 (1H, m), 5.37 (1H, m), 8.68 (2H, m).

(17)
LCMS purity 97%, m/z=366 [M+H]$^+$, $^1$H NMR (300 MHz, CD$_3$OD) δ: 0.92 (6H, m), 1.19 (3H, m), 1.58 (2H, m), 1.75 (4H, m), 1.98 (1H, m), 2.89 (4H, m), 3.70 (1H, m), 8.55 (2H, s).

(20)
LCMS purity 98%, m/z=454 [M+H]$^+$, $^1$H NMR (300 MHz, CD$_3$OD) δ: 1.19-1.62 (10H, m), 1.79-1.92 (6H, m), 2.09 (1H, m), 2.84 (1H, m), 2.97 (2H, m), 5.32 (1H, m), 7.54 (5H, m), 8.67 (2H, m)

(21)
LCMS purity 98%, m/z=386 [M+H]$^+$, NMR (300 MHz, CD$_3$OD) δ: 1.08-1.28 (4H, m), 1.77 (2H, m), 1.98 (1H, m), 2.68-2.87 (4H, m), 4.90 (1H, m), 7.39 (5H, m), 8.54 (2H, s).

(22)
LCMS purity 98%, m/z=464 [M+H]$^+$, $^1$H NMR (300 MHz, CD$_3$OD) δ: 1.13 (9H, s), 1.56-1.71 (12H, m), 1.82 (3H, m), 2.04 (1H, m), 2.91 (3H, m), 3.81 (2H, m), 4.14 (1H, m), 5.39 (1H, m), 8.55 (2H, m).

(23)
LCMS purity 98%, m/z=396 [M+H]$^+$, $^1$H NMR (300 MHz, CD$_3$OD) δ: 1.26 (9H, s), 1.31 (4H, m), 1.94 (2H, m), 2.14 (1H, br s), 3.03 (4H, m), 3.95 (2H, m), 4.16 (1H, m), 8.67 (2H, s).

(24)
LCMS purity 98%, m/z=408 [M+H]$^+$, $^1$H NMR (300 MHz, CD$_3$OD) δ: 1.22-1.33 (3H, m), 1.53-1.73 (11H, m), 2.02 (1H, m), 2.93 (4H, m), 3.91 (2H, m), 4.02 (1H, m), 5.23 (1H, m), 8.55 (2H, s).

(25)
LCMS purity 95%, m/z=340 [M+H]$^+$, $^1$H NMR (300 MHz, CD$_3$OD) δ: 1.28 (2H, m), 1.97 (2H, m), 2.15 (1H, m), 3.07 (4H, m), 4.09 (4H, m), 4.93 (1H, m), 8.67 (2H, m).

(26)
LCMS purity 87%, m/z=504 [M+H]$^+$, $^1$H NMR (300 MHz, CD$_3$OD) δ: 1.02-1.48 (7H, br m), 1.67-1.82 (5H, m), 2.01 (1H, m), 2.97 (2H, m), 3.13 (4H, m), 5.19 (2H, m), 7.49 (3H, m), 7.83 (4H, m), 8.59 (2H, s).

Example 4

Scheme 8

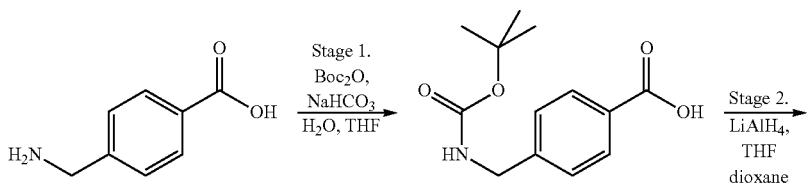

-continued
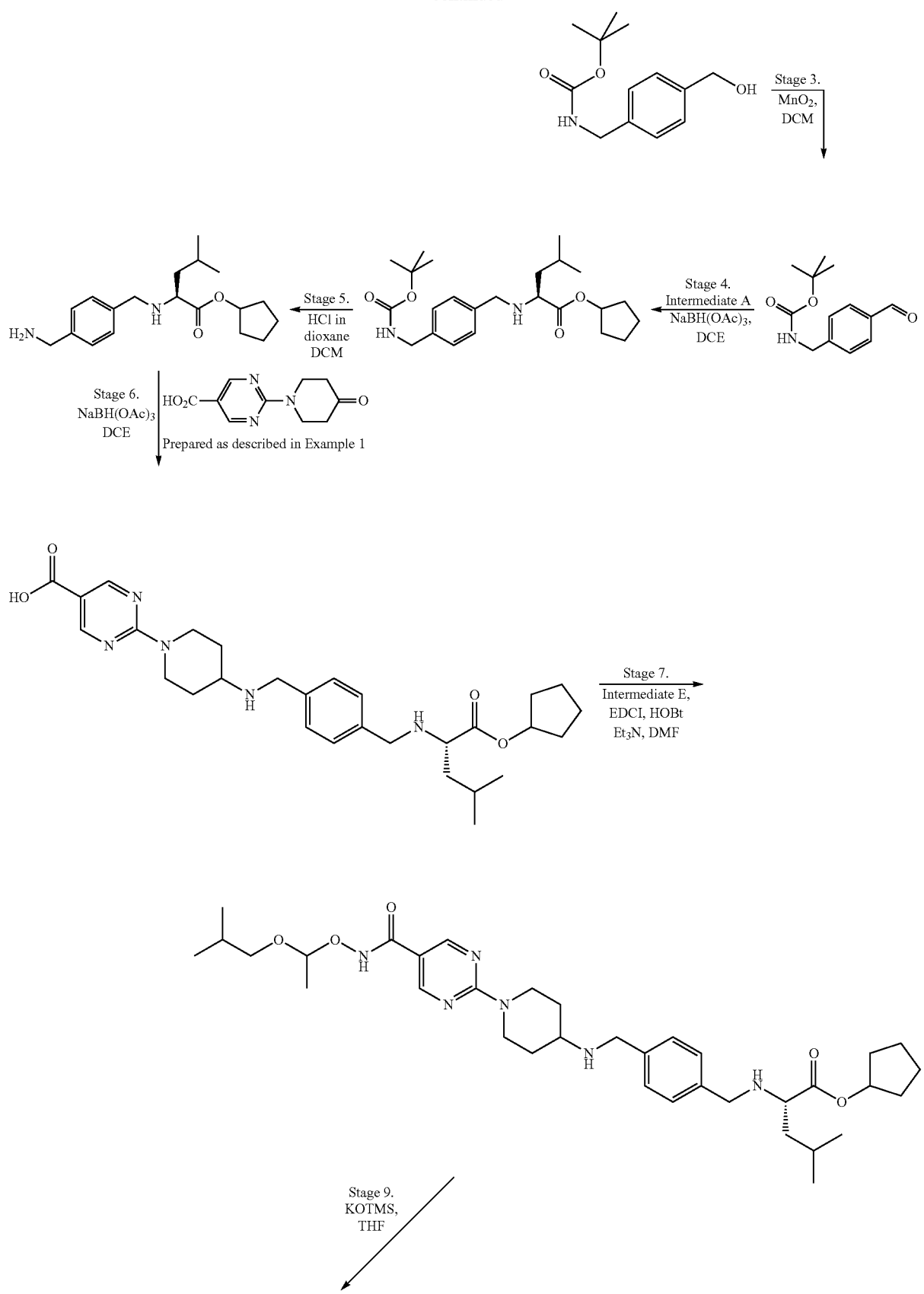

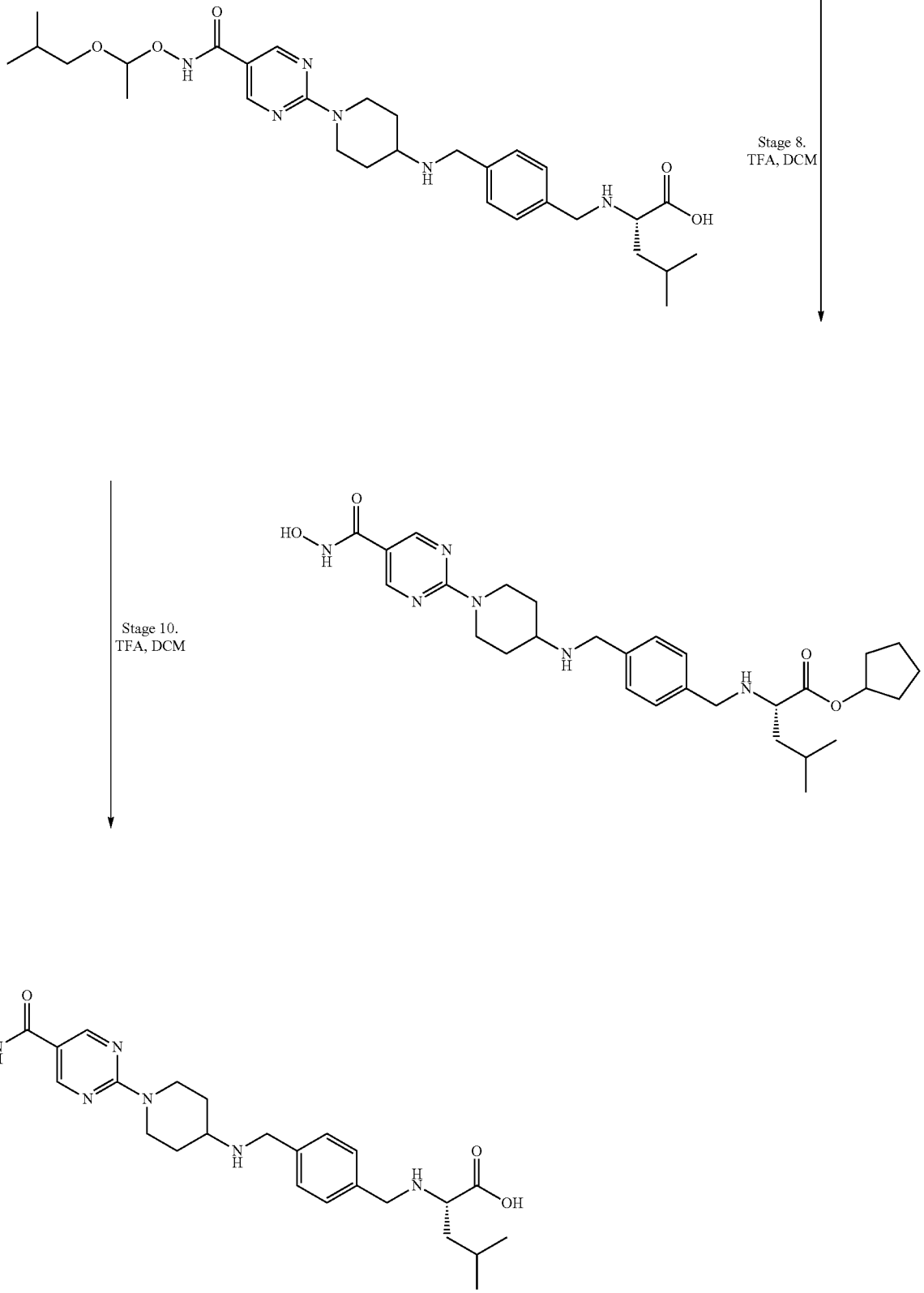

Compounds Prepared:
FIG. 5
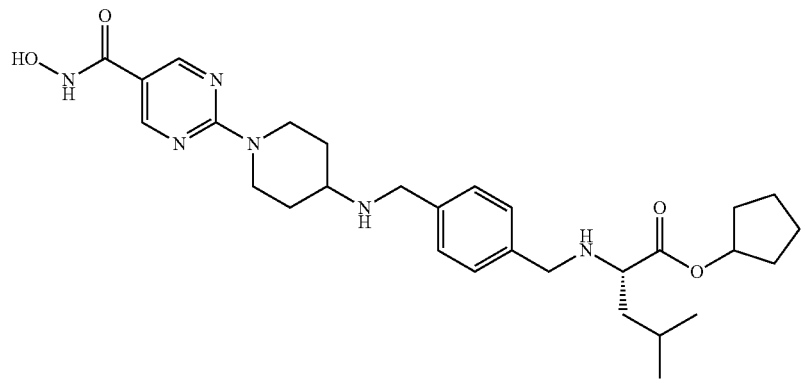
R = Cyclopentyl (27)
R = H (28)
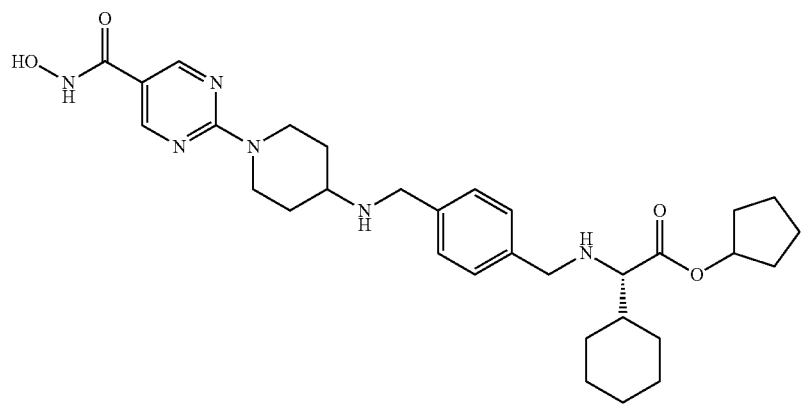
R = Cyclopentyl (29)
R = H (30)
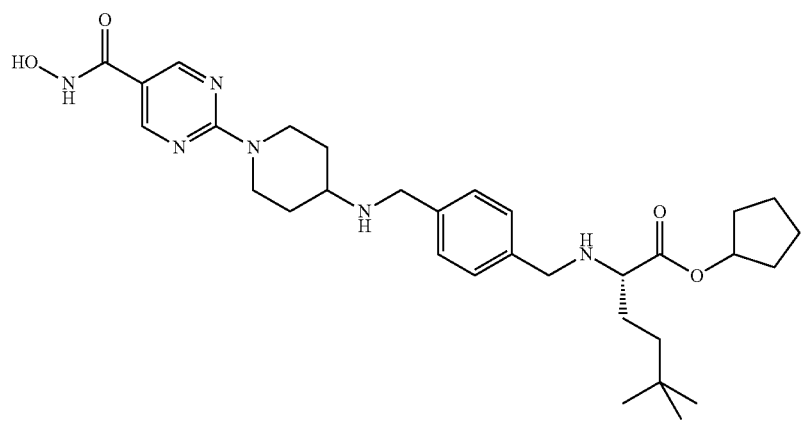
R = Cyclopentyl (31)
R = H (32)

-continued

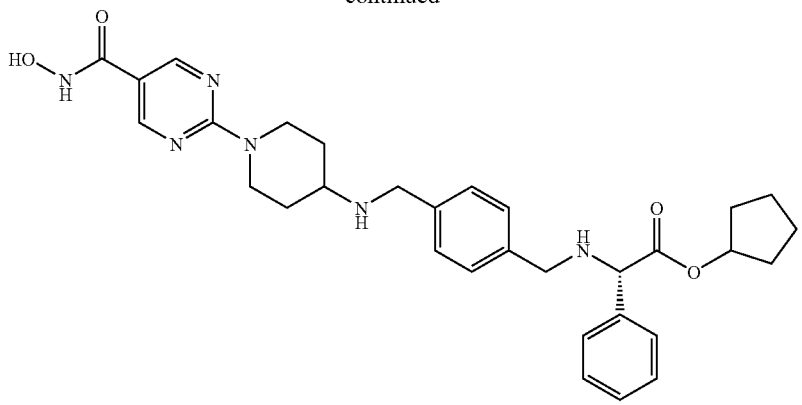

R = Cyclopentyl (33)
R = H (34)

Synthesis of Compounds Outlined in FIG. 5 Exemplified for (27) and (28)

Stage 1—Boc Protection

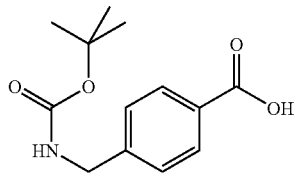 [SMILES: CC(C)(C)OC(=O)NCc1ccc(C(=O)O)cc1]

4-(Aminomethyl)benzoic acid (10.00 g, 65.36 mmol) was stirred with Boc$_2$O (28.00 g, 130.72 mmol) in H$_2$O (100 mL) and THF (100 mL) at RT. Sat NaHCO$_{3(aq)}$ was added until pH ~6 was reached and the reaction was allowed to stir for 16 h. The reaction was then carefully acidified to pH ~3 with 1M HCl$_{aq}$ which caused a solid to precipitate out. This was filtered and dried to give the product as a white solid (16.1 g, 97%). m/z=274 [M+Na]$^+$.

Stage 2—Acid Reduction

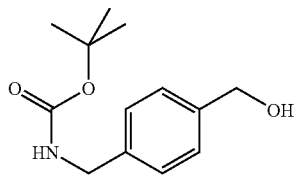 [SMILES: CC(C)(C)OC(=O)NCc1ccc(CO)cc1]

Stage 1 product (16.1 g, 64.14 mmol) was stirred in THF (300 mL) and dioxane (200 mL) at 0° C. under a nitrogen atmosphere. LiAlH$_4$ was then added and the reaction allowed to warm to RT and stir for 16 h. It was then cooled to 0° C. and quenched with sat. NH$_4$Cl$_{aq}$. Na$_2$SO$_4$ was added and the mixture stirred for 30 minutes. It was then filtered through celite and the filtrate concentrated in vacuo to give the product as a light yellow solid (13.1 g, 94%). m/z=260 [M+Na]$^+$.

Stage 3—Alcohol Oxidation

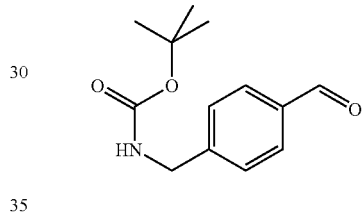

Stage 2 product (5.87 g, 24.73 mmol) was stirred in DCM (200 mL) with MnO$_2$ (16.71 g, 192.20 mmol) for 16 h at RT. The reaction was then filtered through celite and the solvent removed in vacuo to give the product as a yellow oil which was used in the next step without further purification (4.63 g, 80%). m/z=258 [M+Na]$^+$.

Stage 4—Reductive Amination

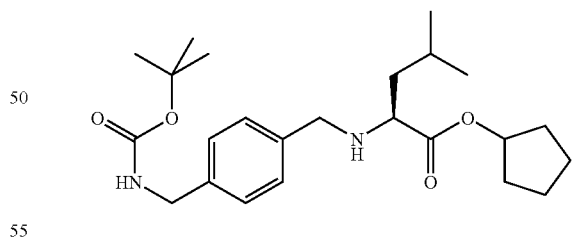

Stage 3 product (650 mg, 2.70 mmol) was stirred in DCE (20 mL), intermediate A (634 mg, 2.70 mmol) and NaBH(OAc)$_3$ (918 mg, 4.33 mmol) at RT under a nitrogen atmosphere for 3 h. After this time the reaction was diluted with H$_2$O (50 mL) and extracted with Et$_2$O (2×100 mL). The combined organic extracts were dried (MgSO$_4$) and solvent removed in vacuo to give the product as a brown oil which was used in the next step without further purification (1.1 g, 98%). m/z=419 [M+H]$^+$.

Stage 5—Boc Deprotection

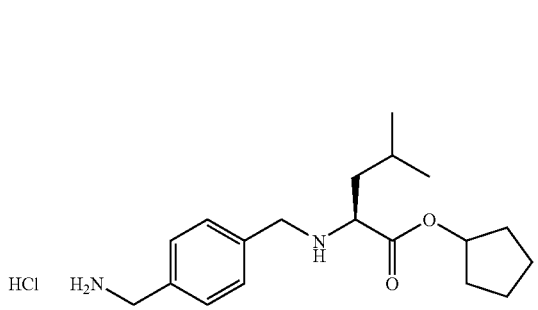 [SMILES: Cl ; CC(C)C[C@H](NCc1ccc(CN)cc1)C(=O)OC1CCCC1]

Stage 4 product (1.1 g, 2.63 mmol) was stirred in DCM (5 mL) with 4M HCl in dioxane (2 mL) at RT under a nitrogen atmosphere for 3 h. The solvent was removed in vacuo and the residue dried to give the product as a brown solid as the HCl salt (670 mg, 100%). m/z=319 [M+H]$^+$.

Stage 6—Reductive Amination

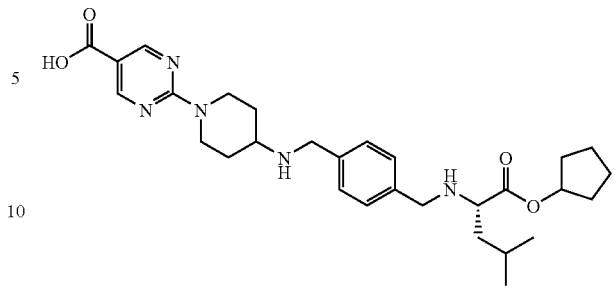

2-(4-Oxopiperidin-1-yl)pyrimidine-5-carboxylic acid (prepared as described in Example 1—100 mg, 0.45 mmol) was stirred in DCE (10 mL) with stage 5 product (159 mg, 0.45 mmol) and NaBH(OAc)$_3$ (191 mg, 0.9 mmol) at RT under a nitrogen atmosphere for 64 h. The reaction was then diluted with H$_2$O (100 mL) and extracted with DCM (2×100 mL). The combined organic layers were dried (Na$_2$SO$_4$) and solvent removed in vacuo. The residue was used in the next step without further purification. m/z=524 [M+H]$^+$.

Stage 7—Protected Hydroxamate Formation

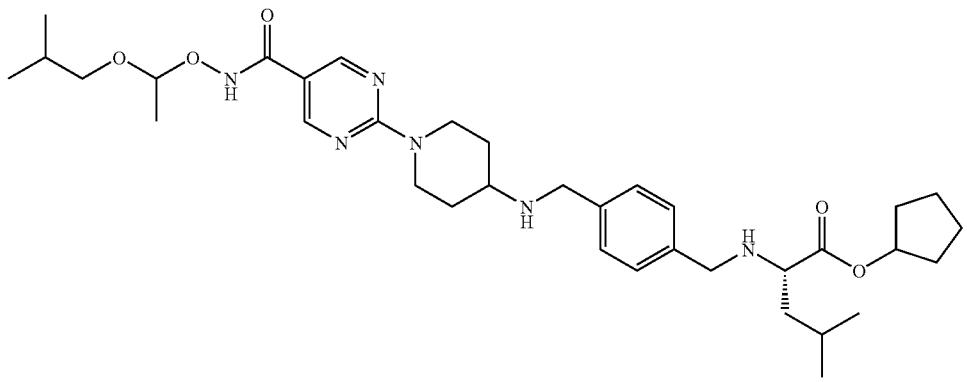 [SMILES: CC(C)COC(C)ONC(=O)c1cnc(N2CCC(NCc3ccc(CN[C@@H](CC(C)C)C(=O)OC4CCCC4)cc3)CC2)nc1]

Stage 6 product (0.45 mmol) was stirred in DMF (10 mL) with intermediate E (621 μL, 4.50 mmol), EDCl (103 mg, 0.54 mmol), HOBt (73 mg, 0.54 mmol) and Et$_3$N (313 μL, 2.25 mmol) at RT under a nitrogen atmosphere for 40 h. The reaction was then diluted with H$_2$O (50 mL) and extracted with DCM (2×100 mL). The combined organic layers were dried (MgSO$_4$) and the solvent removed in vacuo to give the product as a yellow oil which was used in the next step without further purification. m/z=639 [M+H]$^+$.

Stage 8—Hydroxamate Deprotection to Yield Cyclopentyl N-{4-[({1-[5-(hydroxycarbamoyl)pyrimidin-2-yl]piperidin-4-yl}amino)methyl]benzyl}-L-leucinate (27)

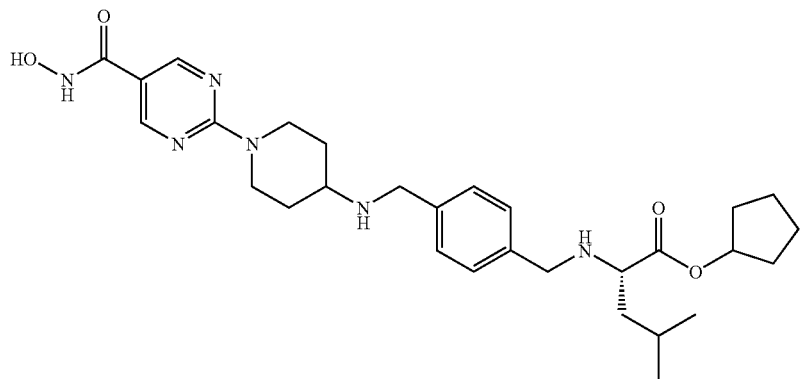 [SMILES: CC(C)C[C@H](NCc1ccc(CNC2CCN(c3ncc(C(=O)NO)cn3)CC2)cc1)C(=O)OC1CCCC1]

Stage 7 product (0.45 mmol) was stirred in DCM (10 mL) with TFA (1 mL) at RT for 30 minutes. The solvent was then removed in vacuo and the residue purified by preparative HPLC to give the product as a pink solid (15 mg, 6% over 3 steps). LCMS purity 96%, m/z=639 [M+H]+. 1H NMR (300 MHz, CD3OD) δ: 1.00 (6H, m), 1.61-1.95 (12H, m), 228 (2H, m), 3.04 (3H, m), 4.01 (1H, m), 4.29 (4H, m), 5.04 (2H, m), 5.34 (1H, m), 7.60 (4H, m), 8.70 (2H, s).

Stage 9—Ester Hydrolysis

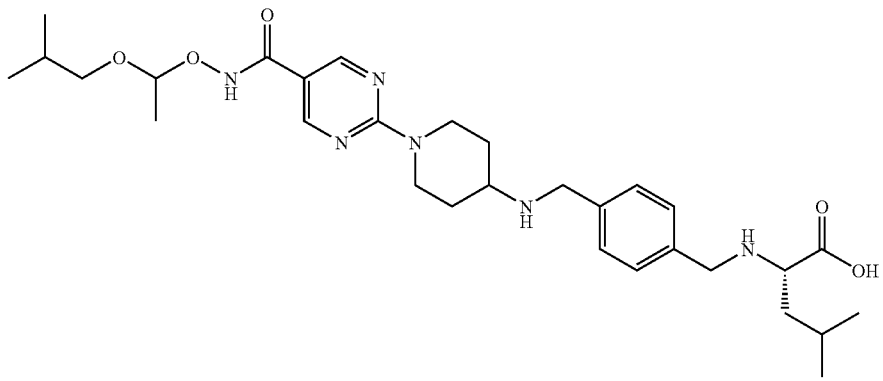 [SMILES: CC(C)COC(C)ONC(=O)c1cnc(N2CCC(NCc3ccc(CN[C@@H](CC(C)C)C(=O)O)cc3)CC2)nc1]

Stage 7 product (0.45 mmol) was stirred in THF (10 mL) with KOTMS (115 mg, 0.9 mmol) for 96 h at RT under a nitrogen atmosphere. The solvent was then removed in vacuo and the residue used in the next step without further purification. m/z=571 [M+H]+.

Stage 10—Hydroxamate Deprotection to Yield N-{-4-[({1-[5-(hydroxycarbamoyl)pyrimidin-2-yl]piperidin-4-yl}amino)methyl]benzyl}-L-leucine (28)

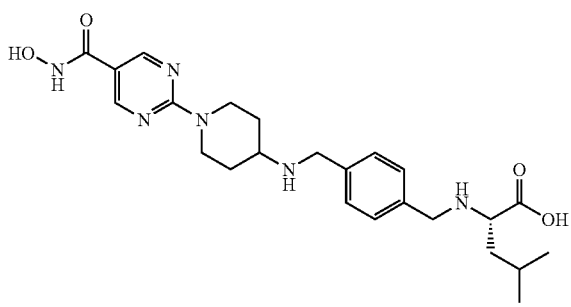 [SMILES: CC(C)C[C@H](NCc1ccc(CNC2CCN(c3ncc(C(=O)NO)cn3)CC2)cc1)C(=O)O]

Stage 9 product was stirred in DCM (10 mL) with TFA (1 mL) at RT for 30 minutes. The solvent was then removed in vacuo and the residue purified by preparative HPLC to give the product as a white solid (5 mg, 3%). m/z=471 [M+H]+, 1H NMR (300 MHz, d6-DMSO) δ: 0.9 (6H, d, J=4.8 Hz), 1.51 (2H, m), 1.71 (2H, m), 2.19 (2H, m), 3.00 (4H, m), 4.42 (2H, br s), 3.75 (1H, m), 4.22 (4H, m), 4.80 (2H, m), 7.52 (4H, m), 8.71 (2H, s), 8.98 (2H, br s), 11.01 (1H, s).

The analogues outlined in FIG. 5 were prepared by the procedure described for (27) and (28). Data for each analogue is given.

(29)

LCMS purity 99%, m/z=565 [M+H]+, 1H NMR (300 MHz, d6-DMSO) δ: 0.88 (2H, m), 1.05-1.30 (5H, m), 1.50-1.85 (18H, m), 2.18 (2H, m), 3.00 (2H, m), 2.25 (2H, m), 4.80 (2H, m), 5.17 (2H, m), 7.54 (4H, m), 8.71 (2H, s), 8.93 (2H, m), 9.45 (1H, br s), 11.10 (1H, s).

(30)

LCMS purity 95%, m/z=497 [M+H]+, 1H NMR (300 MHz, CD3OD) δ: 0.80-1.34 (6H, m), 1.49-1.68 (5H, m), 1.85 (1H, m), 2.17 (2H, m), 2.93 (4H, m), 3.58 (1H, m), 4.20 (4H, m), 4.93 (2H, m), 7.51 (4H, m), 8.59 (2H, m).

(31)

LCMS purity 98%, m/z=569 [M+H]+, 1H NMR (300 MHz, CD3OD) δ: 1.22 (9H, s), 1.51-1.84 (11H, m), 2.18 (2H, m), 2.93 (3H, m), 3.44 (1H, m), 3.79 (2H, qd, J=7.8, 3.3 Hz), 4.24 (4H, m), 4.93 (2H, m), 5.22 (1H, m), 7.52 (4H, m), 8.59 (2H, s).

(32)

LCMS purity 96%, m/z=501 [M+H]+, 1H NMR (300 MHz, CD3OD) δ: 1.25 (9H, s), 1.62 (2H, m), 2.29 (2H, m), 3.07 (4H, m), 3.85 (2H, m), 4.35 (4H, m), 5.07 (2H, m), 7.63 (4H, m), 8.71 (2H, m).

(33)

LCMS purity 98%, m/z=559 [M+H]+, 1H NMR (300 MHz, CD3OD) δ: 1.31-1.93 (12H, m), 2.29 (2H, m), 3.04 (3H, m), 3.56 (1H, m), 4.22 (4H, m), 5.17 (2H, m), 5.30 (1H, m), 7.47-7.43 (9H, m), 8.69 (2H, s).

(34)

LCMS purity 95%, m/z=491 [M+H]+, 1H NMR (300 MHz, CD3OD) δ: 1.63 (2H, m), 2.29 (2H, m), 3.06 (2H, m), 3.29 (2H, m), 3.56 (1H, m), 4.20 (4H, m), 5.07 (2H, m), 7.54 (9H, m), 8.70 (2H, s).

Example 5
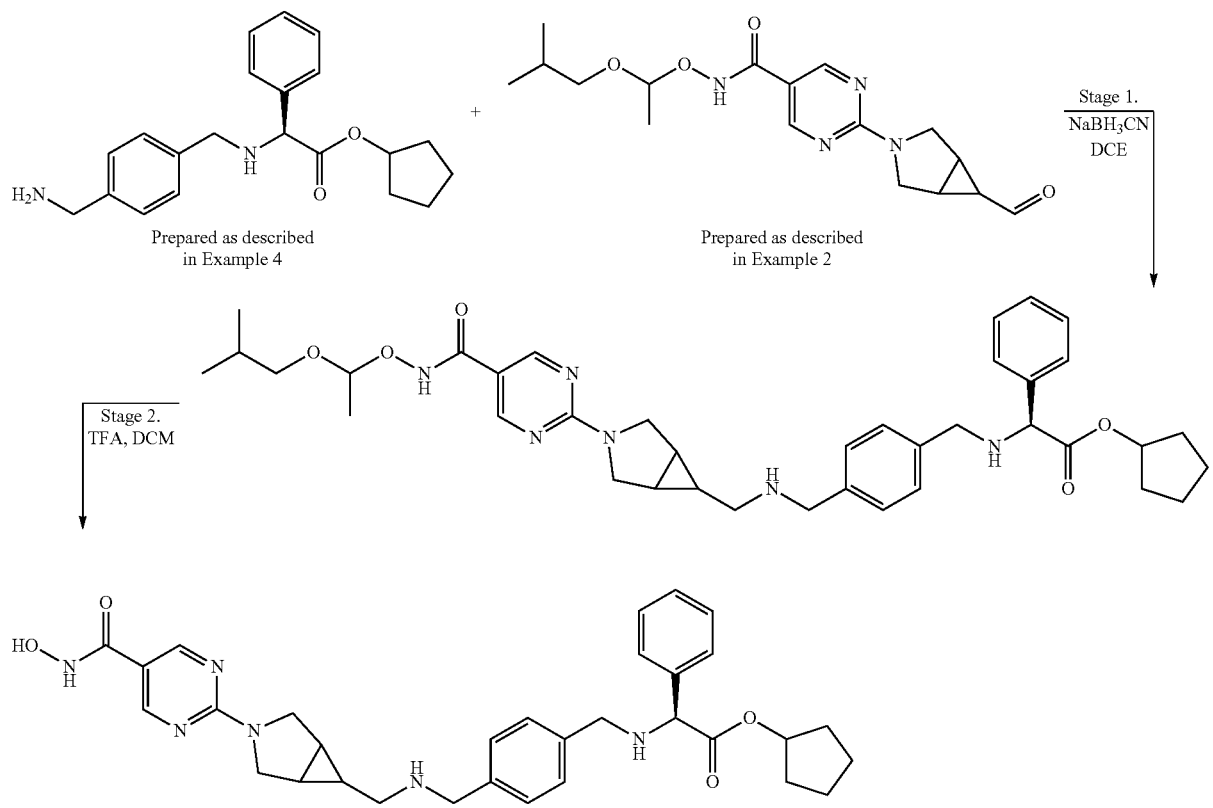
Compounds Prepared:
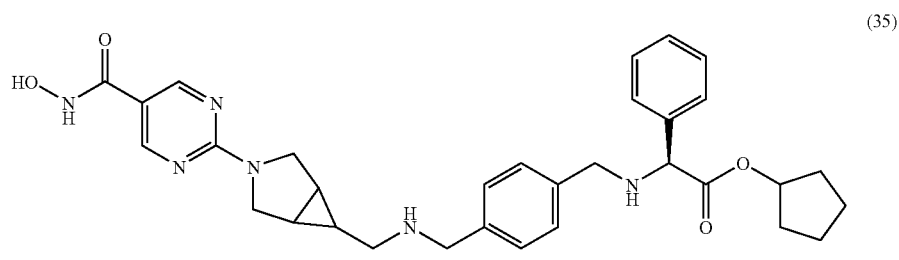
FIG. 6
Stage 1—Reductive Amination
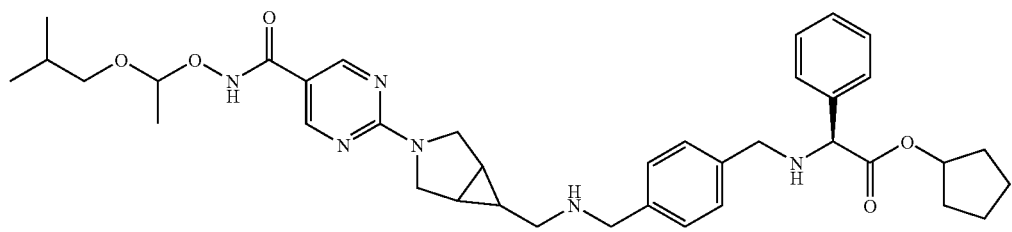 [SMILES: CC(C)COC(C)ONC(=O)c1cnc(N2CC3C(CNCc4ccc(CN[C@H](C(=O)OC5CCCC5)c5ccccc5)cc4)C3C2)nc1]

Cyclopentyl (2S)-{[4-(aminomethyl)benzyl]amino}(phenyl)acetate (prepared as described in Example 4—100 mg, 0.29 mmol) was stirred with 2-(6-formyl-3-azabicyclo[3.1.0]hex-3-yl)-N-(1-isobutoxyethoxy)pyrimidine-5-carboxamide (prepared as described in Example 2—108 mg, 0.29 mmol) and NaBH$_3$CN (36 mg, 0.58 mmol) in DCE (10 mL) at RT under a nitrogen atmosphere for 16 h. The reaction was then diluted with H$_2$O (50 mL) and extracted with DCM (2×100 mL). The combined organic extracts were dried (MgSO$_4$) and the solvent removed in vacuo. The residue was purified by column chromatography (0 to 10% MeOH in DCM) to give the product as a yellow oil (56 mg, 29%). m/z=671 [M+H]$^+$.

Stage 2—Hydroxamate Deprotection to Yield Cyclopentyl (2S)-[(4-{[({3-[5-(hydroxycarbamoyl)pyrimidin-2-yl]-3-azabicyclo[3.1.0]hex-6-yl}methyl)amino]methyl}benzyl)amino](phenyl)acetate (35)

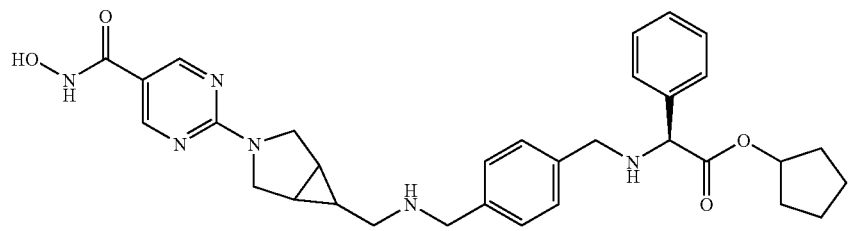 [SMILES: O=C(NO)c1cnc(N2CC3C(CNCc4ccc(CN[C@H](C(=O)OC5CCCC5)c5ccccc5)cc4)C3C2)nc1]

Stage 1 product (56 mg, 0.08 mmol) was stirred in DCM (10 mL) with TFA (1 mL) at RT for 15 minutes. The solvent was then removed in vacuo and the residue purified by preparative HPLC to give the product as a pink solid (12 mg, 25%). m/z=571 [M+H]$^+$, $^1$H NMR (300 MHz, CD$_3$OD) δ: 0.98 (1H, m), 1.31-1.64 (6H, m), 1.76-1.93 (4H, m), 3.09 (2H, d, J=7.5 Hz), 3.61 (2H, d, J=10.5 Hz), 3.98 (2H, d, J=10.5 Hz), 4.15 (2H, m), 4.27 (3H, m), 5.31 (1H, m), 7.57 (9H, m), 8.66 (2H, s).

Example 6

Scheme 10

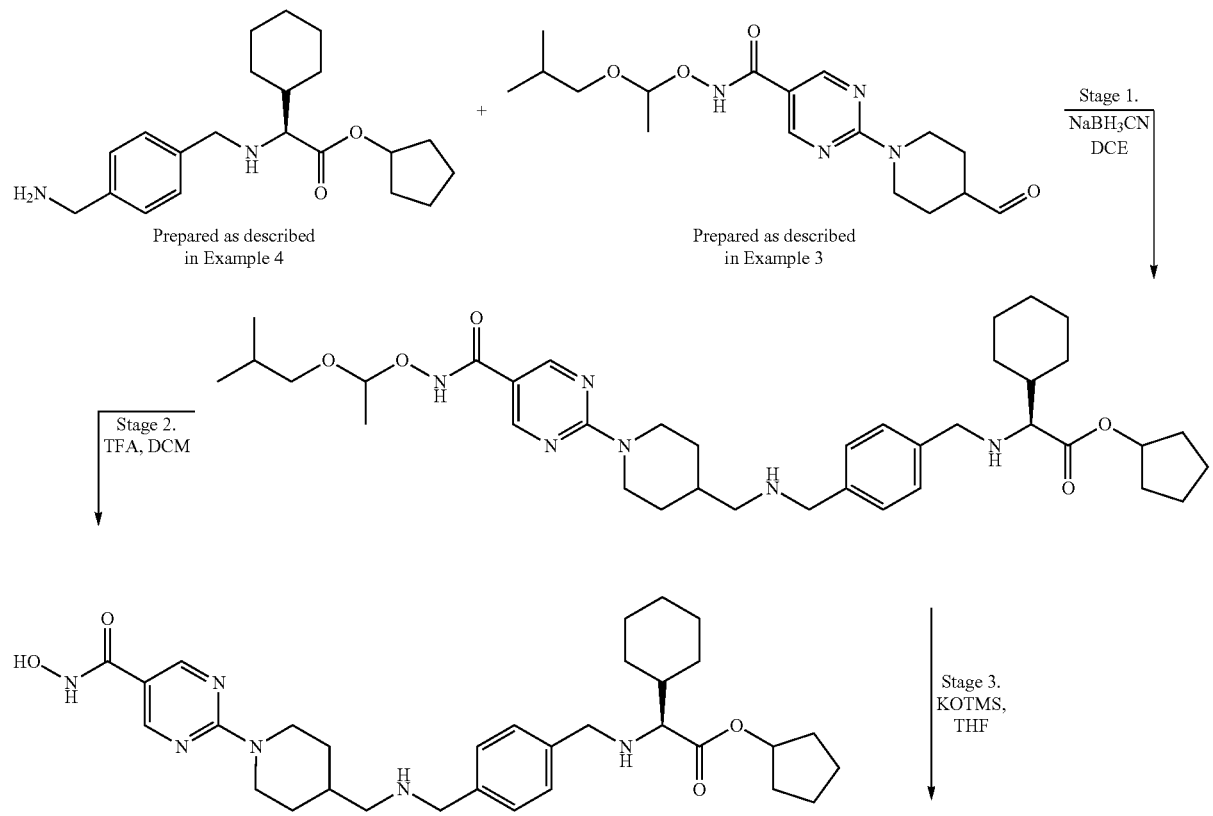

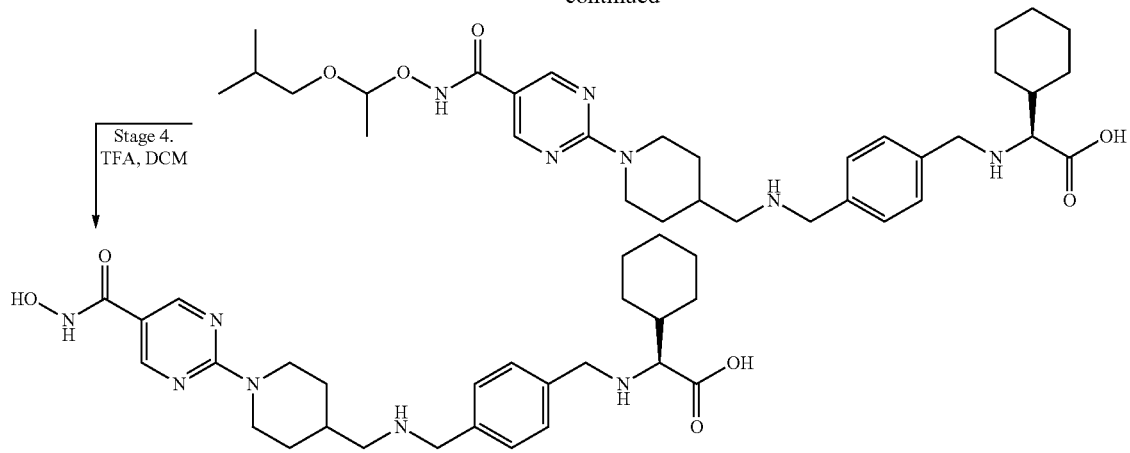
Compounds Prepared:
FIG. 7
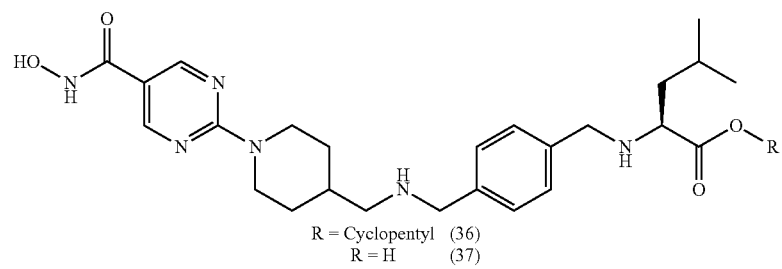
R = Cyclopentyl (36)
R = H (37)
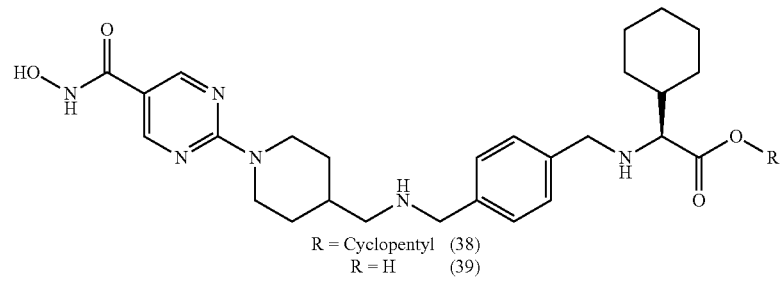
R = Cyclopentyl (38)
R = H (39)
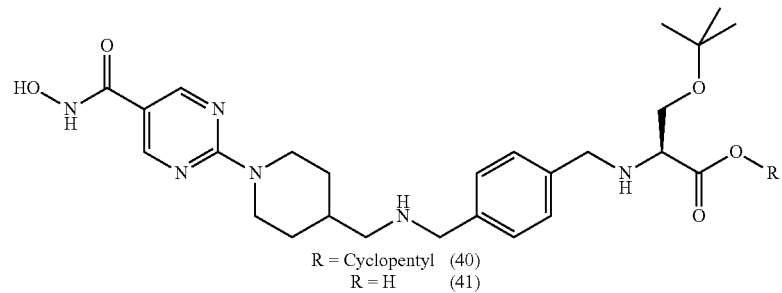
R = Cyclopentyl (40)
R = H (41)
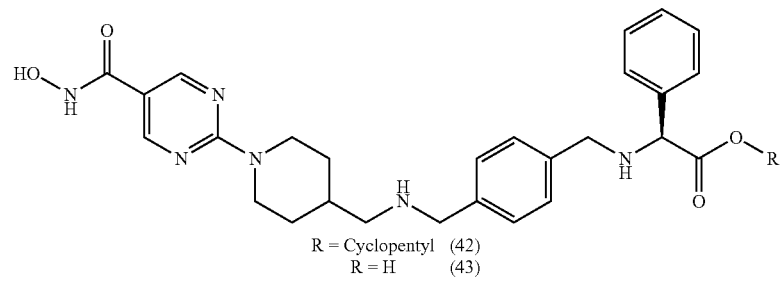
R = Cyclopentyl (42)
R = H (43)

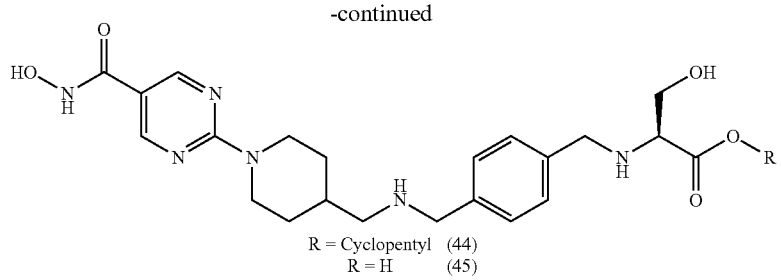

R = Cyclopentyl (44)
R = H (45)

Synthesis of Compounds Outlined in FIG. 7 Exemplified for (38) and (39)

Stage 1—Reductive Amination

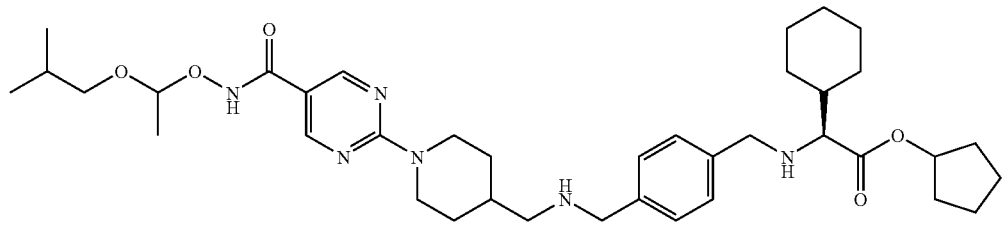

Cyclopentyl (2S)-{[4-(aminomethyl)benzyl]amino}(4-methylcyclohexyl)acetate (prepared as described in Example 4—100 mg, 0.29 mmol) was stirred with 2-(4-formylpiperidin-1-yl)-N-(1-isobutoxyethoxy)pyrimidine-5-carboxamide (prepared as described in Example 3—110 mg, 0.29 mmol) in DCE (10 mL) with NaCNBH$_3$ (36 mg, 0.58 mmol) at RT under a nitrogen atmosphere for 16 h. The reaction was then diluted with H$_2$O (50 mL) and extracted with DCM (2×100 mL). The combined organic extracts were dried (MgSO$_4$) and the solvent removed in vacuo to give the product as a yellow oil which was used in the next step without further purification. m/z=701 [M+Na]$^+$.

Stage 2—Hydroxamate Deprotection to Yield Cyclopentyl (2S)-cyclohexyl[(4-{[({1-[5-(hydroxycarbamoyl)pyrimidin-2-yl]piperidin-4-yl}methyl)amino]methyl}benzyl)amino]acetate (38)

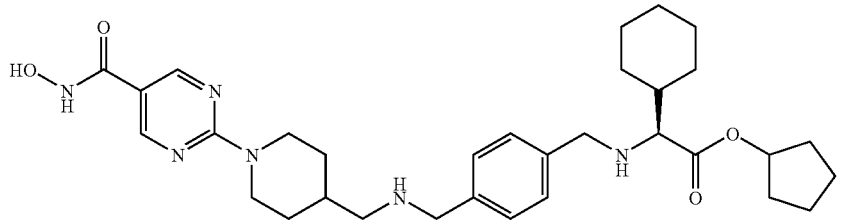 [SMILES: O=C(NO)c1cnc(N2CCC(CNCc3ccc(CN[C@H](C(=O)OC4CCCC4)C4CCCCC4)cc3)CC2)nc1]

Stage 1 product was stirred in DCM (10 mL) with TFA (1 mL) at RT for 30 minutes. The solvent was then removed in vacuo and the residue purified by preparative HPLC to give the product as a purple solid (14 mg, 8% over two steps). LCMS purity >95%, m/z=579 [M+H]$^+$, $^1$H NMR (300 MHz, CD$_3$OD) δ: 1.01-1.42 (10H, m), 1.74-2.12 (18H, m), 3.01 (2H, m), 3.82 (1H, m), 4.28 (4H, m), 5.31 (1H, m), 7.61 (4H, m), 8.66 (2H, m).

Stage 3—Ester Hydrolysis

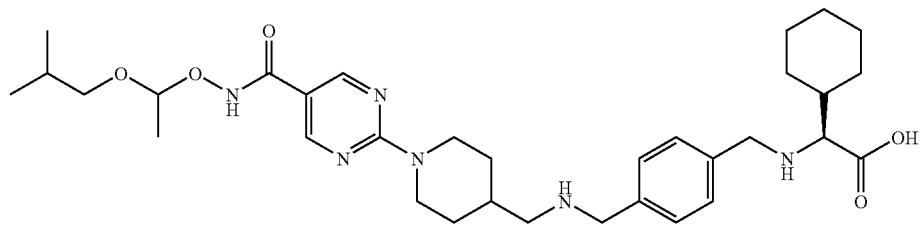

Stage 1 product (100 mg, 0.28 mmol) was stirred in THF (10 mL) with KOTMS (180 mg, 1.40 mmol) at 50° C. under a nitrogen atmosphere. The reaction was allowed to cool to RT and then the solvent was removed in vacuo and the residue used in the next step without further purification. m/z=611 [M+H]+.

Stage 4—Hydroxamate Deprotection to Yield (2S)-cyclohexyl[(4-{[({1-[5-(hydroxycarbamoyl)pyrimidin-2-yl]piperidin-4-yl}methyl)amino]methyl}benzyl)amino]acetic acid (39)

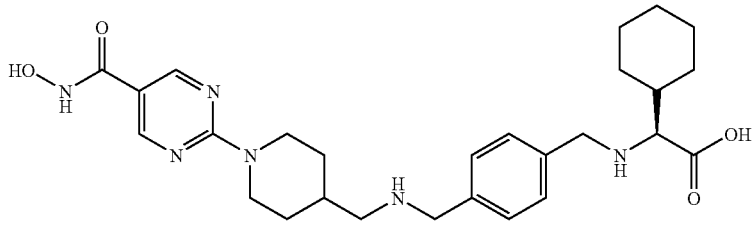 [SMILES: O=C(NO)c1cnc(N2CCC(CNCc3ccc(CN[C@H](C(=O)O)C4CCCCC4)cc3)CC2)nc1]

Stage 3 product was stirred in DCM (10 mL) with TFA (1 mL) at RT for 30 minutes. The solvent was then removed in vacuo and the residue purified by preparative HPLC to give the product as a pink solid (19 mg, 13% over two steps). LCMS purity >95%, m/z=511 [M+H]+, 1H NMR (300 MHz, CD3OD) δ: 1.16-1.41 (9H, m), 1.69-1.91 (8H, m), 2.12 (1H, m), 2.99 (4H, m), 4.29 (4H, m), 4.92 (1H, m), 7.62 (4H, m), 8.66 (2H, s).

The analogues outlined in FIG. 7 were prepared by the procedure described for (38) and (39). Data for each analogue is given.

(36)
LCMS purity 98%, m/z=553 [M+H]+, 1H NMR (300 MHz, d6-DMSO) δ: 0.90 (6H, m), 1.12 (2H, m), 1.28 (2H, d, J=6.6 Hz), 1.65 (9H, m), 1.72 (3H, m), 2.03 (1H, m), 2.73 (2H, m), 2.96 (2H, t, J=12 Hz), 4.20 (4H, m), 4.72 (2H, d, J=13.5 Hz), 5.20 (1H, m), 7.54 (4H, m), 8.66 (2H, s), 8.95 (2H, br s), 9.60 (1H, br s), 11.05 (1H, s).

(37)
LCMS purity 97%, m/z=485 [M+H]+, 1H NMR (300 MHz, CD3OD) δ: 0.87 (6H, m), 1.29 (4H, m), 1.77 (5H, m), 2.00 (1H, m), 2.88 (4H, m), 3.88 (1H, m), 4.18 (4H, m), 7.52 (4H, s), 8.61 (2H, s).

(40)
LCMS purity 99%, m/z=583 [M+H]+, 1H NMR (300 MHz, CD3OD) δ: 1.24 (9H, s), 1.41 (2H, d, J=6.6 Hz), 1.69-1.95 (12H, br m), 2.15 (1H, br s), 3.00 (4H, m), 3.93 (2H, m), 4.20 (1H, m), 4.31 (4H, m), 5.34 (1H, m), 7.63 (4H, m), 8.66 (2H, s).

(41)
LCMS purity 99%, m/z=515 [M+H]+, 1H NMR (300 MHz, CD3OD) δ: 1.25 (9H, s), 1.29 (4H, m), 1.89 (2H, m), 2.12 (1H, br s), 3.01 (4H, m), 3.94 (2H, qd, J=9.0, 3.9 Hz), 4.12 (1H, t, J=3.6 Hz), 4.33 (4H, app. d, J=18.6 Hz), 7.63 (4H, s), 8.66 (2H, s).

(42)
LCMS purity 98%, m/z=573 [M+H]+, 1H NMR (300 MHz, d6-DMSO) δ: 1.13-1.83 (12H, br m), 2.04 (1H, m), 2.85 (2H, m), 2.96 (2H, t, J=12 Hz), 3.99 (2H, m), 4.15 (2H, m), 4.70 (2H, d, J=13.2 Hz), 5.16 (2H, m), 7.51 (9H, m), 8.66 (2H, s), 8.97 (2H, br s), 10.13 (1H, br s), 11.05 (1H, s).

(43)
LCMS purity 99%, m/z=505 [M+H]+, 1H NMR (300 MHz, CD3OD) δ: 0.89 (1H, m), 1.08 (2H, m), 1.77 (3H, m), 2.01 (1H, m), 2.90 (4H, m), 4.08 (4H, m), 4.94 (1H, s), 7.45 (9H, m), 8.55 (2H, s).

(44)
LCMS purity 99%, m/z=528 [M+H]+, 1H NMR (300 MHz, CD3OD) δ: 1.30 (3H, m), 1.67-1.78 (11H, m), 2.12 (1H, m), 3.02 (4H, m), 4.06 (3H, m), 4.33 (4H, app. d, J=18 Hz), 5.34 (1H, m), 7.66 (4H, m), 8.66 (2H, s).

(45)
LCMS purity 96%, m/z=459 [M+H]+, 1H NMR (300 MHz, CD3OD) δ: 1.25 (4H, m), 1.89 (2H, m), 2.15 (1H, m), 2.99 (4H, m), 4.00 (1H, m), 4.09 (2H, m), 4.34 (4H, app. d, J=21.9 Hz), 7.64 (4H, m), 8.66 (2H, s).

Example 7

Scheme 11

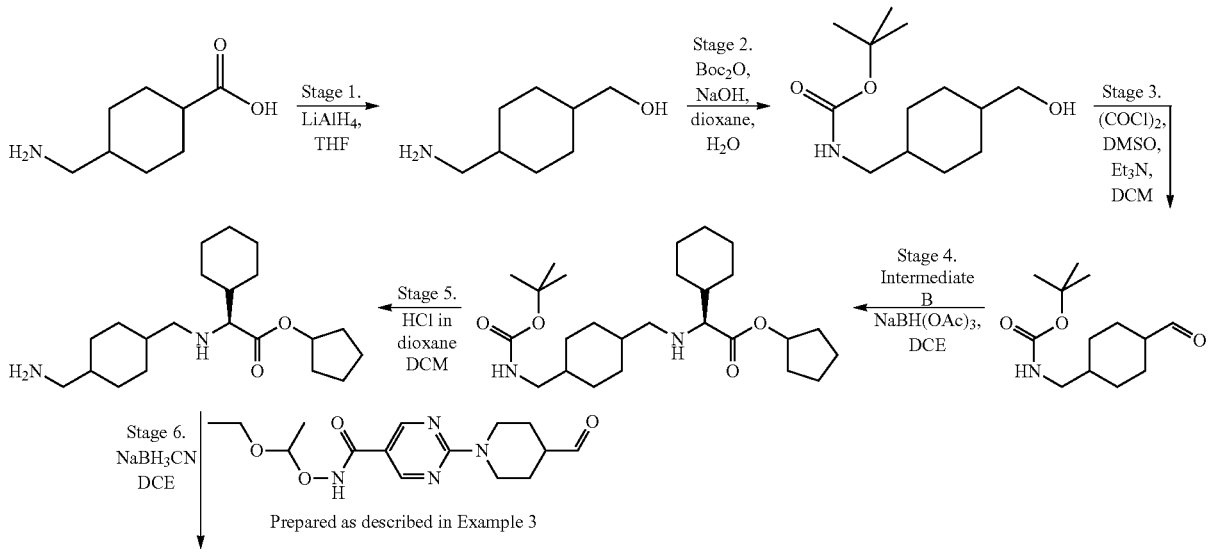

Prepared as described in Example 3

-continued
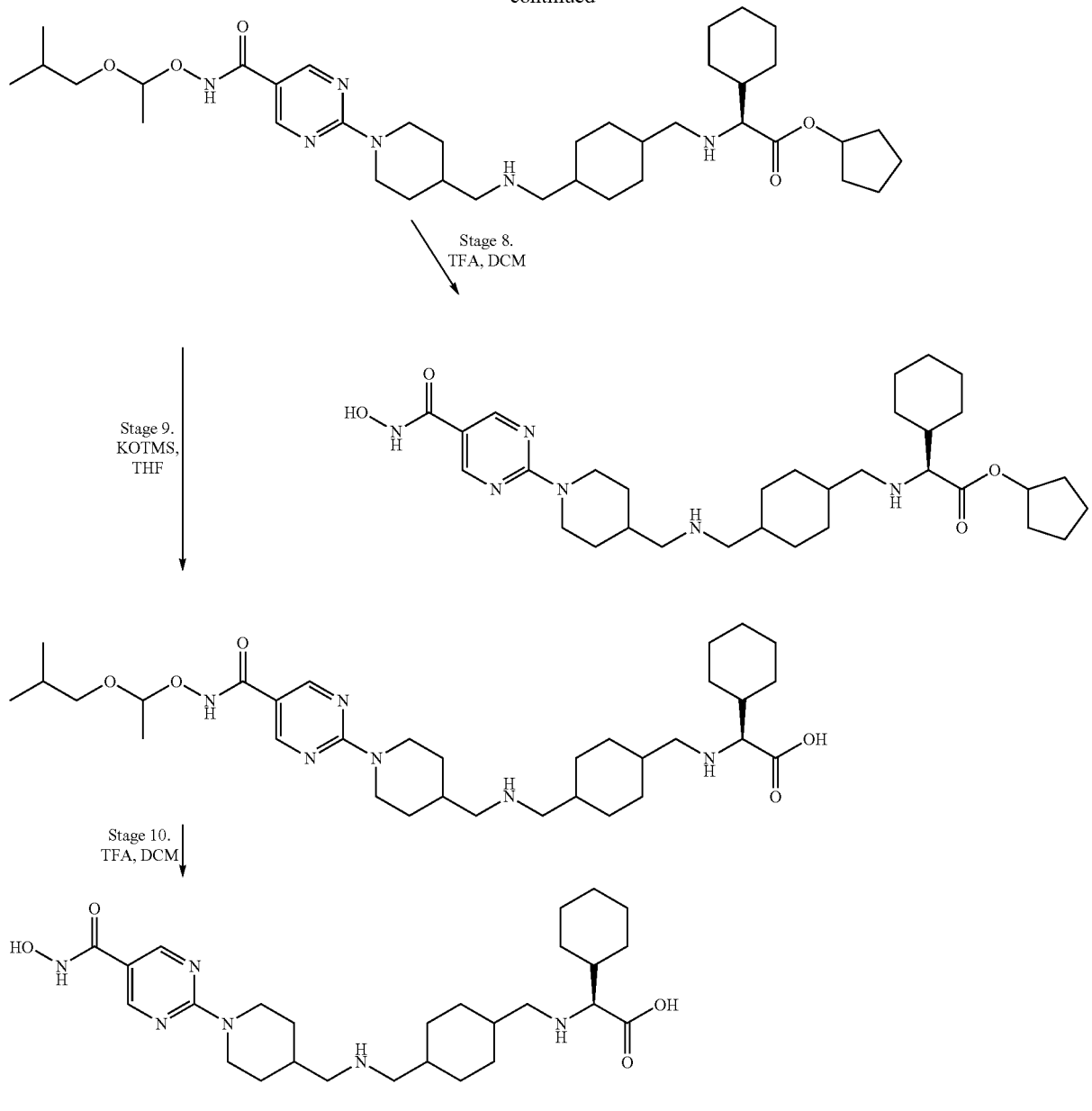
Compounds Prepared:
FIG. 8
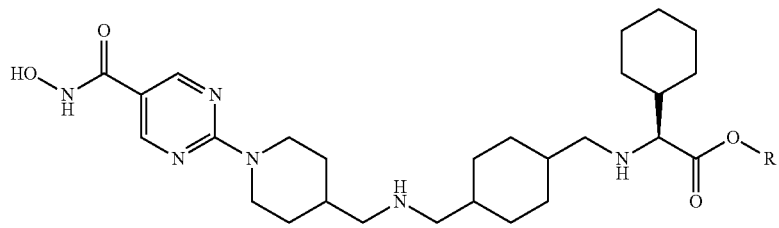
R = cyclopentyl (46)
R = H (47)

Stage 1—Acid Reduction

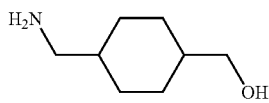

4-(Aminomethyl)cyclohexanecarboxylic acid (4.00 g, 25.44 mmol) was stirred in THF (100 mL) at 0° C. under a nitrogen atmosphere. LiAlH$_4$ (2.90 g, 76.33 mmol) was then added and the reaction allowed to warm to RT and stir for 3 h. It was then cooled to 0° C. and quenched with H$_2$O. Na$_2$SO$_4$ was then added and the mixture stirred for 10 minutes. It was then filtered through celite and the filtrate concentrated in vacuo to give the product as a colourless oil which solidified on standing to give the product as a white solid (3.72 g, 100%). $^1$H NMR (300 MHz, d$_6$-DMSO) δ: 0.95 (4H, m), 1.22-1.47 (5H, m), 1.86 (4H, m), 2.55 (2H, d, J=6.6 Hz), 4.46 (2H, d, J=6.3 Hz).

Stage 2—Boc Protection

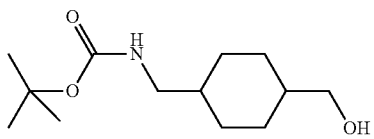 [SMILES: CC(C)(C)OC(=O)NCC1CCC(CO)CC1]

Stage 1 product (3.72 g, 26.01 mmol) was stirred with NaOH (1.00 g, 26.01 mmol) and di-tert-butyl-dicarbonate (6.24 g, 28.61 mmol) in H$_2$O (50 mL) and dioxane (50 mL) at RT for 16 h. The reaction was then concentrated in vacuo. When approximately 50% had been evaporated, a solid precipitated out of solution and was collected and dried to give the product as a white solid (5.5 g, 87%). m/z=266 [M+Na]$^+$, $^1$H NMR (300 MHz, CDCl$_3$) δ: 0.82 (4H, m), 1.28 (2H, m), 1.37 (9H, s), 1.70 (4H, m), 2.76 (2H, t, J=6.3 Hz), 3.19 (2H, d, J=6.3 Hz), 4.32 (1H, br s), 6.75 (1H, m).

Stage 3—Alcohol Oxidation

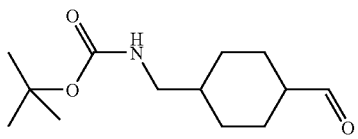 [SMILES: CC(C)(C)OC(=O)NCC1CCC(C=O)CC1]

A solution of DCM (100 mL) and (COCl)$_2$ (1.58 mL, 18.14 mmol) was stirred under a nitrogen atmosphere and cooled to −78° C. DMSO (2.27 mL, 32.02 mmol) was then added whilst maintaining the temperature below −65° C. A solution of stage 2 product (4.5 g, 17.79 mmol) in DCM (50 mL) was then prepared and added slowly to the reaction mixture, again maintaining the temperature below −65° C. When addition was complete Et$_3$N (9.99 mL, 71.69 mmol) was slowly added, again maintaining the temperature below −65° C. When addition was complete the reaction was allowed to warm to RT and then the solvent removed in vacuo. The residue was purified by column chromatography (0 to 10% MeOH in DCM) to give the product as a light yellow oil (5 g, >100%—contains some Et$_3$N). m/z=264 [M+Na]$^+$, $^1$H NMR (300 MHz, CDCl$_3$) δ: 1.02 (2H, m), 1.30 (2H, m), 1.45 (9H, s), 1.90 (2H, m), 2.03 (2H, m), 3.01 (2H, t, J=6.3 Hz), 4.57 (1H, br s), 9.63 (1H, s).

Stage 4—Reductive Amination

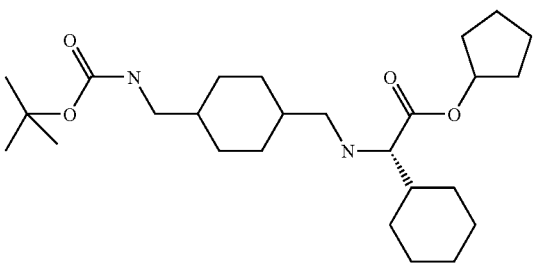 [SMILES: CC(C)(C)OC(=O)NCC1CCC(CN[C@H](C(=O)OC2CCCC2)C2CCCCC2)CC1]

Stage 3 product (1.00 g, 4.14 mmol) was stirred with intermediate B (1.08 g, 4.14 mmol) and sodium triacetoxyborohydride (1.33 g, 6.21 mmol) in DCE (20 mL) at RT for 16 h. The reaction was then diluted with H$_2$O (100 mL) and extracted with DCM (2×100 mL). The combined organic extracts were dried (MgSO$_4$) and the solvent removed in vacuo to give the product as a grey solid which was used in the next step without further purification (1.74 g, 94%). m/z=451 [M+H]$^+$.

Stage 5—Boc Deprotection

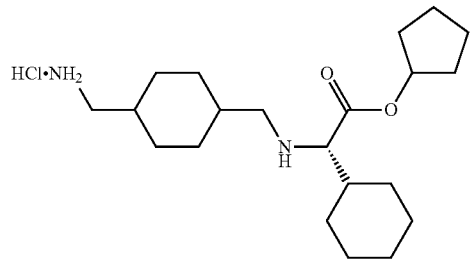

Stage 4 product (1.74 g, 3.87 mmol) was stirred in DCM (10 mL) with 4M HCl in dioxane (3 mL) at RT for 16 h. The solvent was then removed in vacuo and the residue dried under vacuum to give the product as a white solid (1.36 g, 98%). m/z=351 [M+H]$^+$, $^1$H NMR (300 MHz, d$_6$-DMSO) δ: 0.90-1.20 (9H, m), 1.50-2.00 (21H, m), 2.65 (4H, m), 3.85 (1H, m), 5.25 (1H, m), 7.83 (2H, m).

Stage 6—Reductive Amination

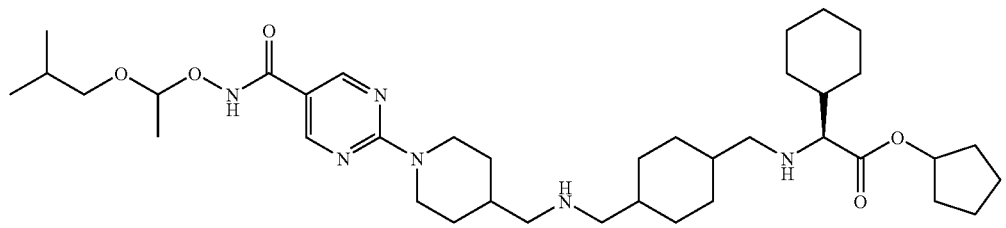

Stage 5 product (216 mg, 0.56 mmol) was stirred with 2-(4-formylpiperidin-1-yl)-N-(1-isobutoxyethoxy)pyrimidine-5-carboxamide (prepared as described in Example 3—200 mg, 0.57 mmol) and NaBH₃CN (70 mg, 1.12 mmol) in DCE (10 mL) at RT under a nitrogen atmosphere for 48 h. The reaction was then diluted with H₂O (100 mL) and extracted with DCM (2×100 mL). The combined organic extracts were dried (MgSO₄) and the solvent removed in vacuo to give the product as a yellow oil which was used in the next step without further purification.

Stage 7—Hydroxamate Deprotection to Yield Cyclopentyl (2S)-cyclohexyl{[(4-{[({1-[5-(hydroxycarbamoyl)pyrimidin-2-yl]piperidin-4-yl}methyl)amino]methyl}cyclohexyl)methyl]amino}acetate (46)

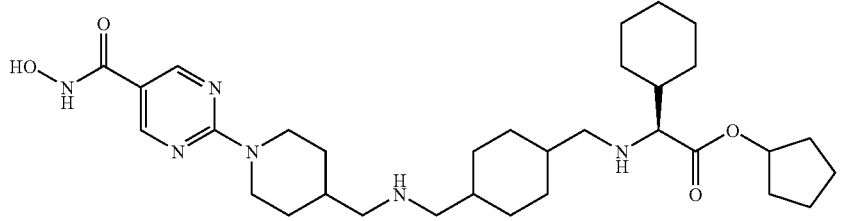

Stage 6 product (0.28 mmol) was stirred in DCM (10 mL) with TFA (0.5 mL) at RT for 30 minutes. The solvent was then removed in vacuo and the residue purified by preparative HPLC to give the product as a pink solid (15 mg, 9% over two steps). LCMS purity >95%, m/z=585 [M+H]⁺, ¹H NMR (300 MHz, CD₃OD) δ: 0.96-1.39 (13H, m), 1.72-2.16 (23H, m), 2.81-3.04 (7H, m), 3.84 (2H, d, J=3.9 Hz), 5.36 (1H, m), 8.66 (2H, s).

Stage 8—Ester Hydrolysis

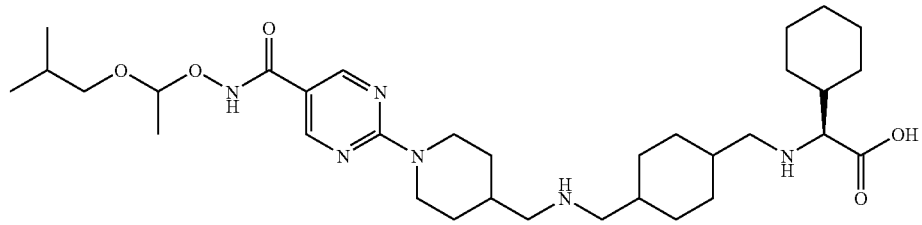

Stage 6 product (0.28 mmol) was stirred with KOTMS (180 mg, 1.4 mmol) and THF (10 mL) at 50° C. under a nitrogen atmosphere for 16 h. The reaction was the cooled to RT and the solvent removed in vacuo and the residue used in the next step without further purification. m/z=617 [M+H]⁺.

Stage 9—Hydroxamate Deprotection to Yield (2S)-cyclohexyl{[(4-{[({1-[5-(hydroxycarbamoyl)pyrimidin-2-yl]piperidin-4-yl}methyl)amino]methyl}cyclohexyl)methyl]amino}acetic acid (47)

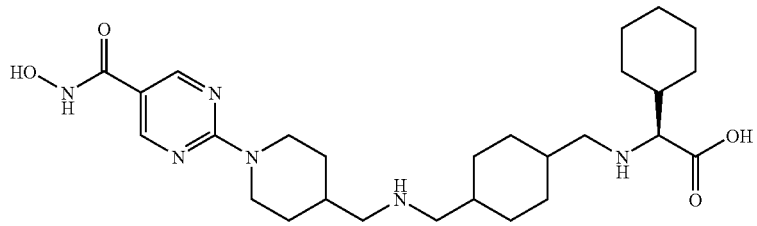 [SMILES: O=C(NO)c1cnc(N2CCC(CNCC3CCC(CN[C@H](C(=O)O)C4CCCCC4)CC3)CC2)nc1]

Stage 8 product (0.28 mmol) was stirred in DCM (10 mL) with TFA (1 mL) at RT for 30 minutes. The solvent was then removed in vacuo and the residue purified by preparative HPLC to give the product as a white solid (5 mg, 3% over two steps). m/z=517 [M+H]⁺, ¹H NMR (300 MHz, CD₃OD) δ: 1.13-1.44 (11H, m), 1.75-1.94 (15H, m), 2.82-3.09 (8H, m), 3.39 (1H, m), 3.65 (1H, m), 4.94 (1H, m), 8.67 (2H, m).

Example 8
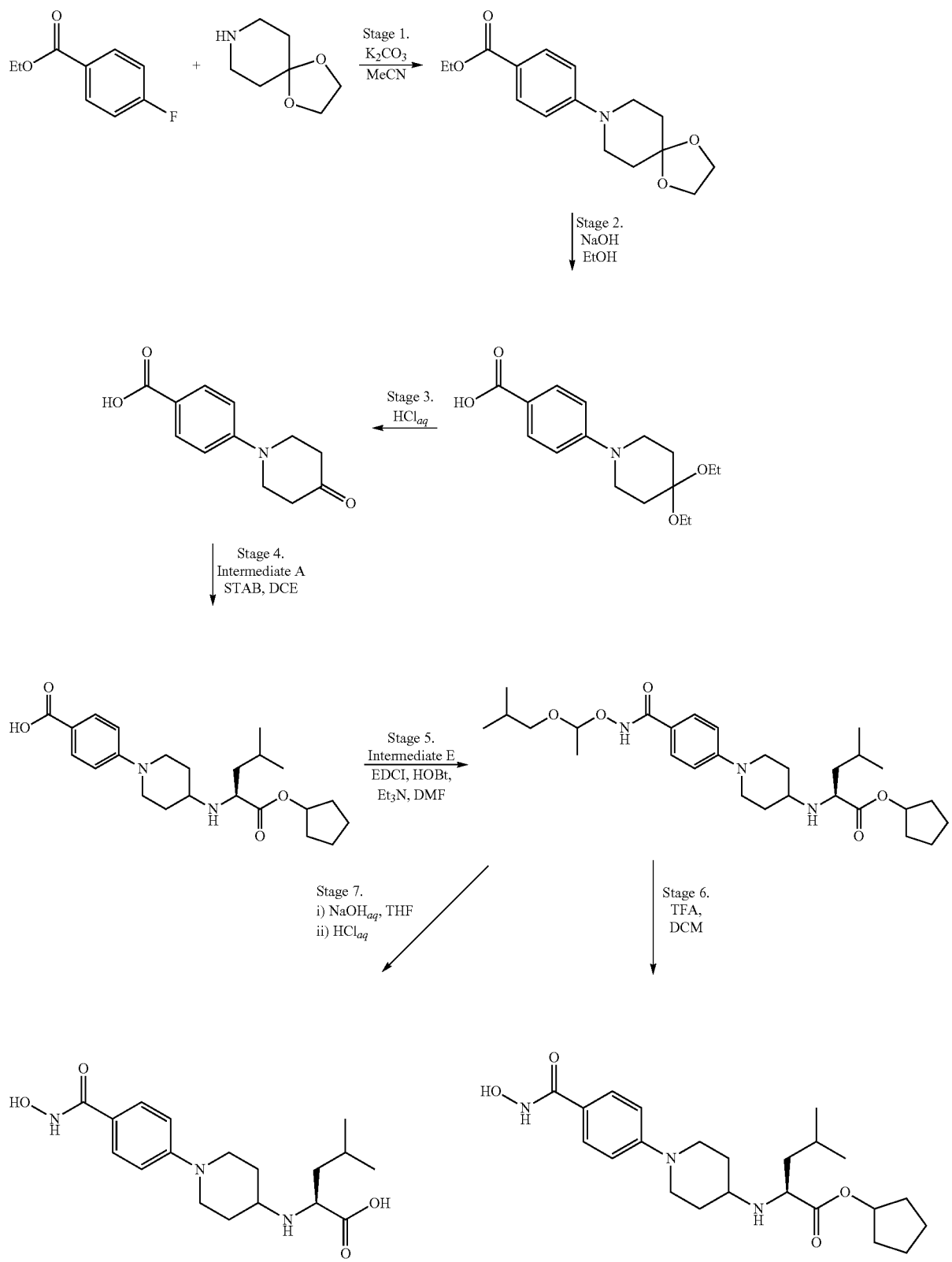
Scheme 12

Compounds Prepared:

FIG. 9

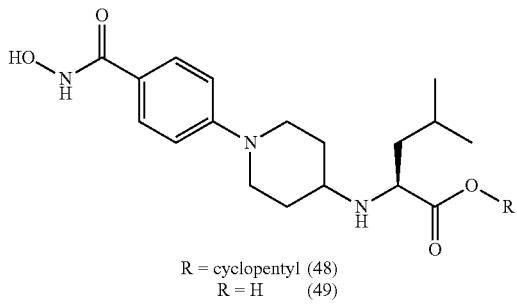

R = cyclopentyl (48)
R = H (49)

Stage 1—Coupling

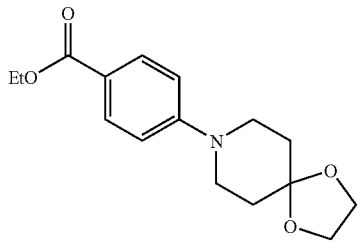 [SMILES: CCOC(=O)c1ccc(N2CCC3(CC2)OCCO3)cc1]

Ethyl 4-fluorobenzoate (6.75 g, 40.1 mmol) and 1,4-dioxa-8-azaspiro[4.5]decane (2.73 g, 19.1 mmol) were stirred with K$_2$CO$_3$ (8.5 g, 61.5 mmol) in MeCN (10 mL) at 95° C. for 1 week. The mixture was added to EtOAc (50 mL) and washed with water (3×50 mL). The organic was dried (MgSO$_4$), filtered and concentrated in vacuo. The product was purified by flash chromatography (2% MeOH in DCM) to yield a yellow oil (5.58 g, 48%). m/z=292 [M+H]$^+$.

Stage 2—Ester Hydrolysis

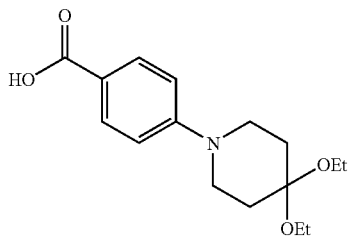 [SMILES: CCOC1(OCC)CCN(c2ccc(C(=O)O)cc2)CC1]

Stage 1 product (5.58 g, 19.15 mmol) was dissolved in EtOH (25 mL) and stirred with 50% NaOH$_{aq}$ (25 mL) at 60° C. for 3 h. The mixture was cooled to RT and 2M HCl$_{aq}$ (50 mL) added. The mixture was then stirred at 30° C. for 3 days. The product was extracted with DCM (4×50 mL), dried (MgSO$_4$), concentrated in vacuo and recrystallised from EtOH to yield a white solid (1.459 g, 26%). m/z=294 [M+H]$^+$.

Stage 3—Acetal Deprotection

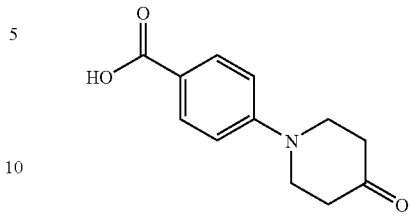

Stage 2 product (509 mg, 1.735 mmol) was stirred in 1M HCl$_{aq}$ (15 ml) at RT for 30 minutes. The mixture was concentrated in vacuo, added to minimal water, filtered and dried in a desiccator. The product was obtained as a white solid (279 mg, 73%). m/z=220 [M+H]$^+$ Stage 4—Reductive Amination

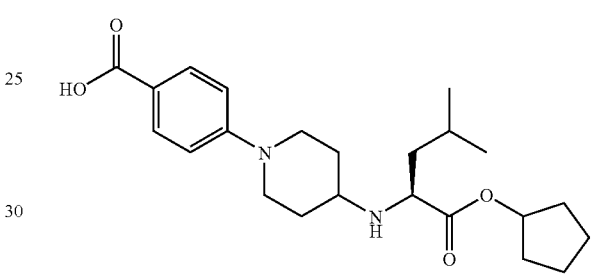

Stage 3 product (279 mg, 1.27 mmol) and intermediate A (303 mg, 1.28 mmol) were stirred in 1,2-dichloroethane (10 mL) with sodium triacetoxyborohydride (405 mg, 1.91 mmol) at RT overnight. The mixture was added to DCM (100 mL) and washed with water (2×100 mL). The combined aqueous layers were re-extracted with DCM (100 mL), then the combined organics were dried (Na$_2$SO$_4$), filtered and concentrated in vacuo to yield a brown oil (495 mg, 97%). m/z=403 [M+H]$^+$.

Stage 5—Protected Hydroxamate Coupling

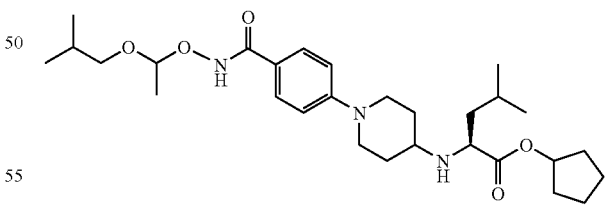

Stage 4 product (495 mg, 1.20 mmol), was dissolved in DMF and stirred with intermediate E (0.84 mL, 6.12 mmol), triethylamine (0.84 mL, 6.03 mmol), HOBt (228 mg, 1.49 mmol) and EDCl (295 mg, 1.54 mmol) at RT for 2 days. The mixture was added to DCM (100 mL) and washed with water (2×100 mL). The combined aqueous layers was re-extracted with DCM (100 mL), then the combined organics were dried (Na$_2$SO$_4$), filtered and concentrated in vacuo to yield a yellow oil (638 mg, quant). m/z=518 [M+H]$^+$.

Stage 6—Hydroxamate Deprotection to Yield Cyclopentyl N-{1-[4-(hydroxycarbamoyl)phenyl]piperidin-4-yl}-L-leucinate (48)

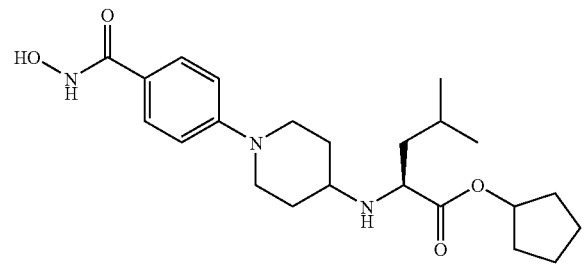 [SMILES: CC(C)C[C@H](NC1CCN(c2ccc(C(=O)NO)cc2)CC1)C(=O)OC1CCCC1]

Stage 5 product (309 mg, 597 μmol) was stirred in DCM (5 mL) and TFA (0.5 mL) at RT for 1 h. The reaction mixture was purified directly by preparative HPLC to give a white solid (75 mg, 30%). LCMS purity 95%, m/z=418 [M+H]$^+$. $^1$H NMR (300 MHz, CD$_3$OD) δ: 7.67 (2H, d, J=8.5 Hz), 7.02 (2H, d, J=8.5 Hz), 5.38 (1H, m), 4.13 (1H, m), 4.04 (2H, d, J=12.4 Hz), 2.92 (2H, m), 1.97 (2H, m), 1.88-1.68 (13H, m), 1.04 (6H, dd, J=6.2, 7.8 Hz).

Stage 7—Ester Hydrolysis and Hydroxamate Deprotection to Yield N-{1-[4-(hydroxycarbamoyl)phenyl]piperidin-4-yl}-L-leucine (49)

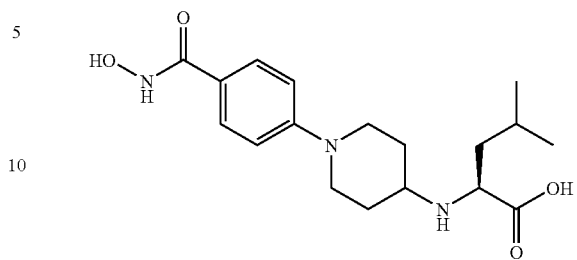

Stage 5 product (50 mg, 120 μmol) was stirred in THF (5 mL) and 1M NaOH$_{aq}$ (5 mL, 5 mmol) at RT for 3 days. The mixture was acidified to pH ~3 with 2M HCl$_{aq}$, and stirred for 20 minutes, then it was concentrated in vacuo and purified by preparative HPLC to give a white solid (5 mg, 12%). LCMS purity 90%, m/z=350 [M+H]$^+$. $^1$H NMR (300 MHz, d$_6$-DMSO) δ: 10.90 (1H, s), 7.63 (2H, d, J=8.8 Hz), 6.93 (2H, d, J=9.0 Hz), 3.84 (2H, d, J=12.9 Hz), 3.24 (1H, t, J=6.9 Hz), 2.97-2.76 (3H, m), 1.96-1.74 (3H, m), 1.54-1.32 (4H, m), 0.89 (6H, t, J=6.4 Hz).

Example 9

Scheme 13

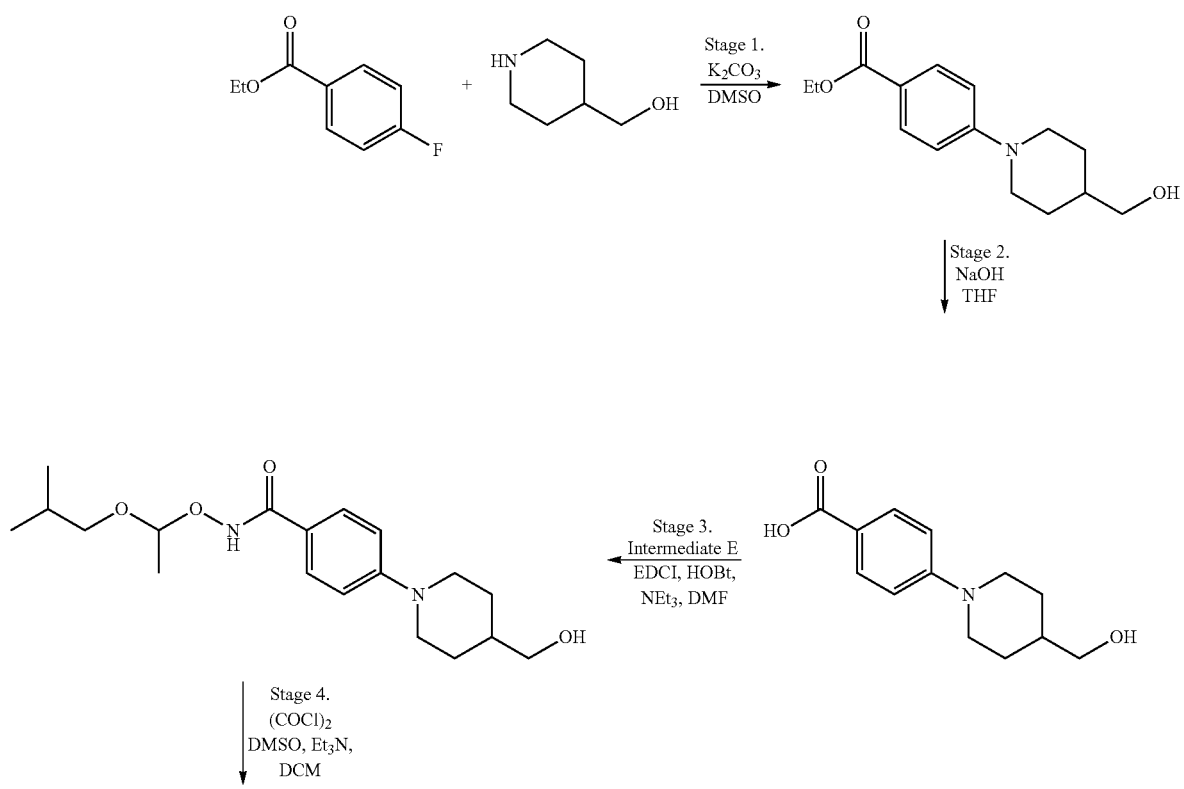

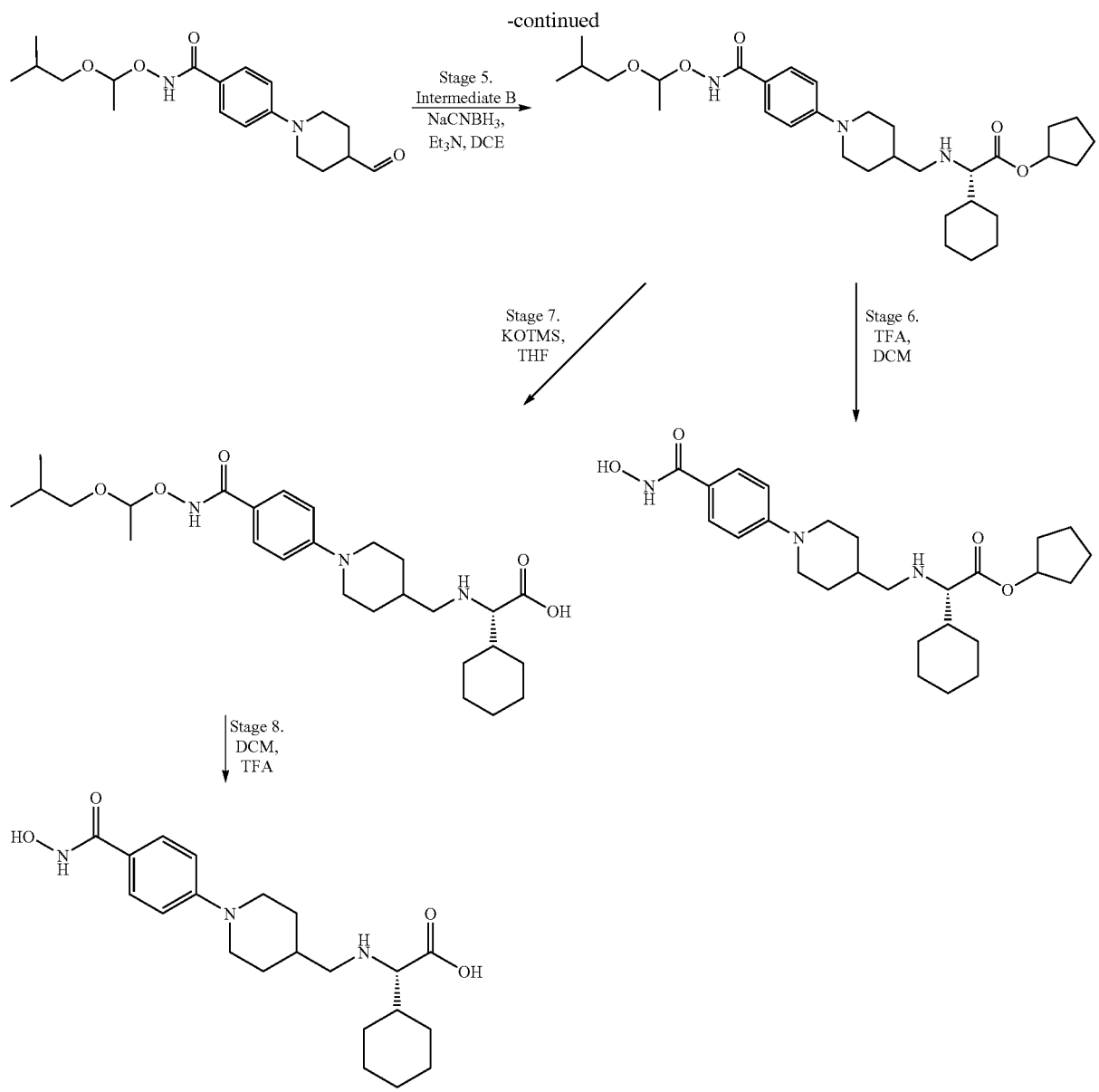

Compounds Prepared:

FIG. 10

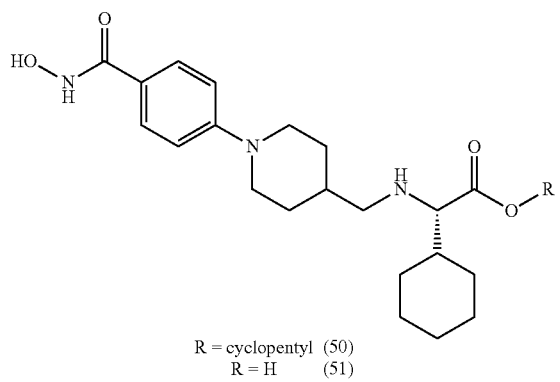

R = cyclopentyl (50)
R = H (51)

Stage 1—Coupling

Ethyl 4-fluorobenzoate (2.740 g, 16.29 mmol) and 4-piperidinemethanol (1.876 g, 16.29 mmol) were stirred in DMSO (100 mL) with $K_2CO_3$ (6.765 g, 48.95 mmol) at 100° C. overnight. The mixture was cooled to RT and added to water (100 mL). The product was extracted with DCM (2×100 mL), dried ($Na_2SO_4$) and evaporated in vacuo to give a yellow oil. This was used in the next stage without further purification or characterisation.

Stage 2—Ester Hydrolysis

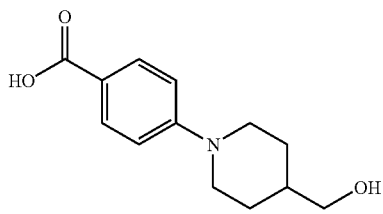

Stage 1 product (16.29 mmol) was stirred in 2M NaOH$_{aq}$ (40 mL, 80 mmol) and THF (40 mL) at RT for 2 days. Since the reaction had shown little progress, 50% NaOH$_{aq}$ (10 mL) was added, and the mixture stirred at 55° C. for 2 further days. The mixture was then cooled to RT and the resulting precipitate was filtered and retained. The filtrate was acidified to pH 3 with 2M HCl$_{aq}$ and stirred for 1 h at RT. A second crop of precipitate was then filtered. Both crops were dried to yield white solids (combined 3.052 g, 80%). m/z=236 [M+H]$^+$.

Stage 3—Protected Hydroxamate Formation

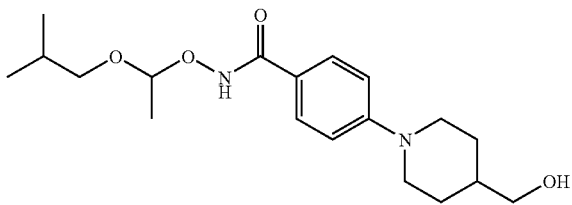 [SMILES: CC(C)COC(C)ONC(=O)c1ccc(N2CCC(CO)CC2)cc1]

Stage 2 product (3.031 g, 12.17 mmol) was stirred in DMF (100 mL) with intermediate E (8.0 mL, 58.27 mmol), triethylamine (8 mL, 57.39 mmol), HOBt (2.759 g, 18.02 mmol) and EDCl (3.390 g, 17.72 mmol) at RT overnight. The mixture was added to DCM (100 mL) and washed with water (2×100 mL). The combined aqueous layers were re-extracted with DCM (100 mL), then the combined organic was dried (Na$_2$SO$_4$), and concentrated in vacuo. The crude product was purified by column chromatography (1 to 10% MeOH in DCM) to yield a yellow oil (3.076 g, 75%). m/z=351 [M+H]$^+$.

Stage 4—Swern Oxidation

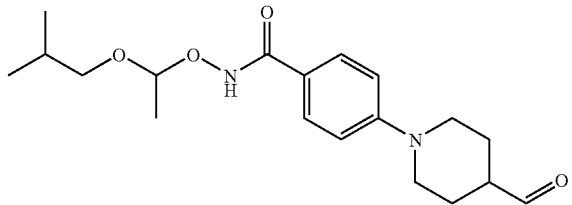 [SMILES: CC(C)COC(C)ONC(=O)c1ccc(N2CCC(C=O)CC2)cc1]

DCM (200 mL) was stirred with oxalyl chloride (0.80 mL, 9.17 mmol) at −72° C. To this DMSO (1.1 mL, 15.50 mmol) was added dropwise, maintaining the temperature at −72° C. Stage 3 product (3.08 g, 8.78 mmol) was dissolved in DCM (100 mL) and added to the mixture dropwise, maintaining the temperature at −72° C. The reaction was then stirred at this temperature for a further 5 minutes before being allowed to warm to RT. The mixture was then concentrated in vacuo and purified by flash chromatography (1 to 10% MeOH in DCM) to yield an off white solid (3.05 g, quant). m/z=349 [M+H]$^+$.

Stage 5—Reductive Amination

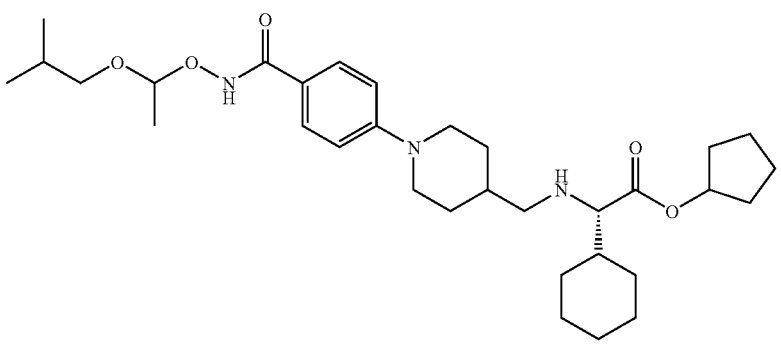 [SMILES: CC(C)COC(C)ONC(=O)c1ccc(N2CCC(CN[C@H](C(=O)OC3CCCC3)C3CCCCC3)CC2)cc1]

Stage 4 product (206 mg, 0.591 mmol), was stirred with intermediate B (155 mg, 0.592 mmol) in 1,2-dichloroethane (20 mL). To this was added triethylamine (0.85 ml, 6.10 mmol) and sodium cyanoborohydride (525 mg, 8.35 mmol) and the mixture stirred at RT for 2 days. The reaction was quenched with water (50 mL) and extracted with DCM (2×50 mL). The organic phase was dried (MgSO$_4$), and concentrated in vacuo to yield a yellow oil (313 mg, 95%). m/z=558 [M+H]$^+$.

Stage 6—Hydroxamate Deprotection to Yield Cyclopentyl (2S)-cyclohexyl[({1-[4-(hydroxycarbamoyl)phenyl]piperidin-4-yl}methyl)amino]acetate (50)

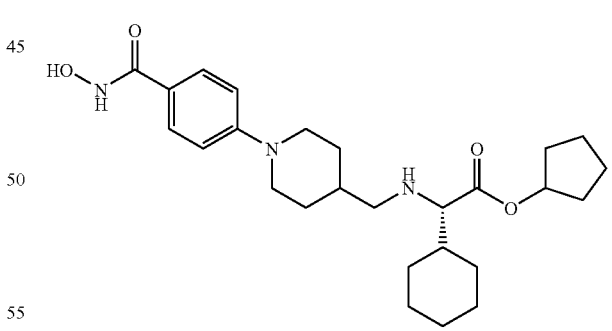

Stage 5 product (180 mg, 323 μmol) was stirred in DCM (10 mL) and TFA (0.5 mL) at RT for 1 h. The product was purified directly by preparative HPLC to yield a white solid (7.4 mg, 5%). LCMS purity 95%, m/z=458 [M+H]$^+$. $^1$H NMR (300 MHz, CD$_3$OD) δ: 7.67 (2H, d, J=8.3 Hz), 7.02 (2H, d, J=8.3 Hz), 5.40 (1H, t, J=5.4 Hz), 3.93 (3H, m), 3.07-2.85 (4H, m), 2.05-1.70 (20H, m), 1.47-1.06 (8H, m).

Stage 7—Ester Hydrolysis

Stage 8—Hydroxamate Deprotection to Yield (2S)-cyclohexyl[({1-[4-(hydroxycarbamoyl)phenyl]piperidin-4-yl}methyl)amino]acetic acid (51)

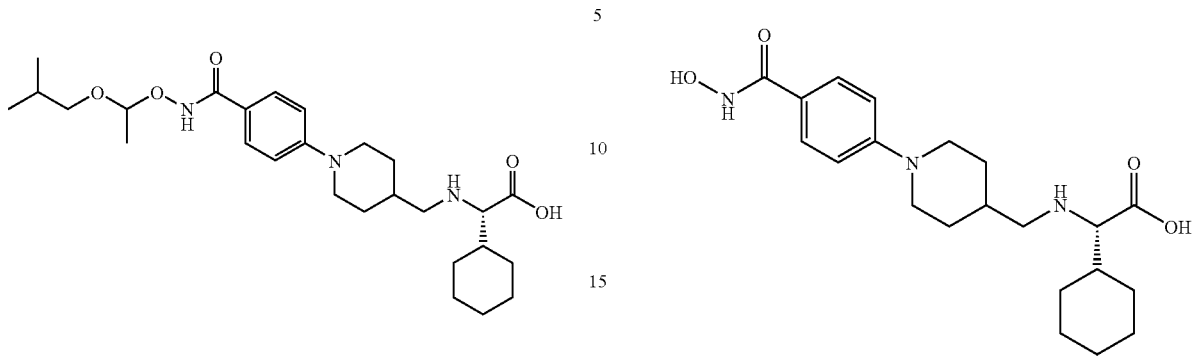

Stage 5 product (184 mg, 330 μmol) was stirred in THF (10 mL) with potassium trimethylsilanolate (428 mg, 3.34 mmol) at 50° C. for 4 days. The mixture was concentrated in vacuo and the residue used crude for next stage.

Stage 7 product was stirred in DCM (10 mL) with TFA (0.5 mL) at RT for 1 h. The mixture was concentrated in vacuo and the product purified by preparative HPLC to yield a white solid (6.8 mg, 5%). LCMS purity 93%, m/z=390 [M+H]$^+$. $^1$H NMR (300 MHz, CD$_3$OD) δ: 7.65 (2H, s), 6.99 (2H, s), 3.90 (2H, d, J=12.5 Hz), 3.84 (1H, s), 2.89 (4H, m), 2.01-1.65 (10H, m), 1.45-1.05 (8H, m).

Example 10

Scheme 14

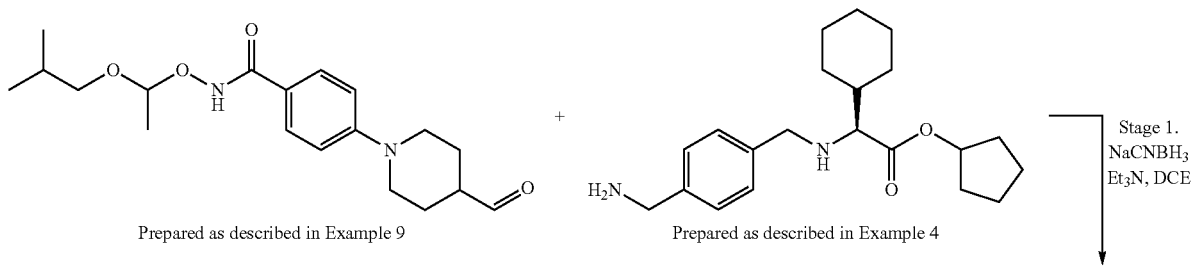

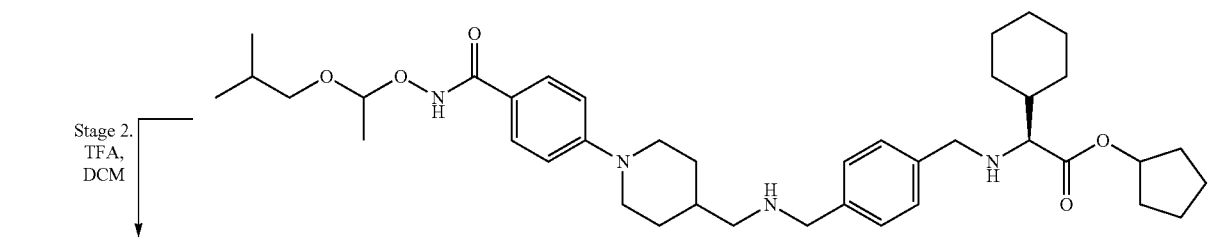

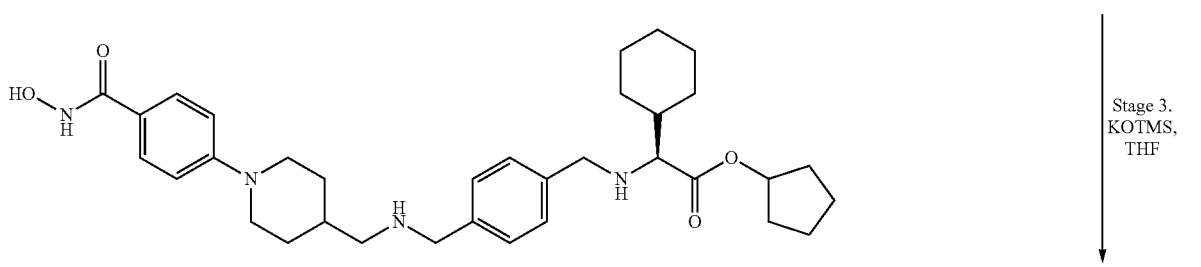

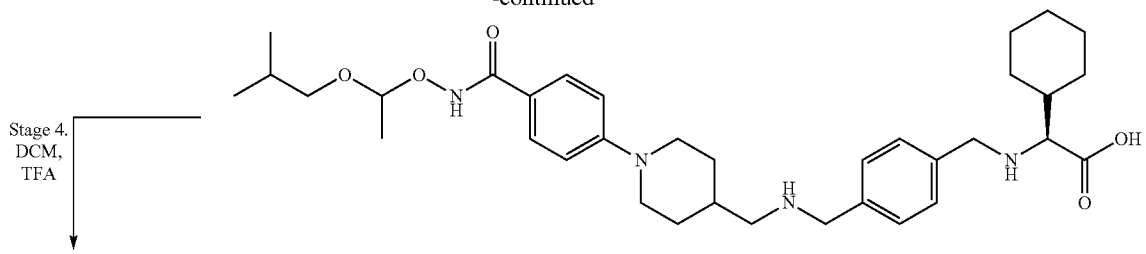

Stage 4.
DCM,
TFA

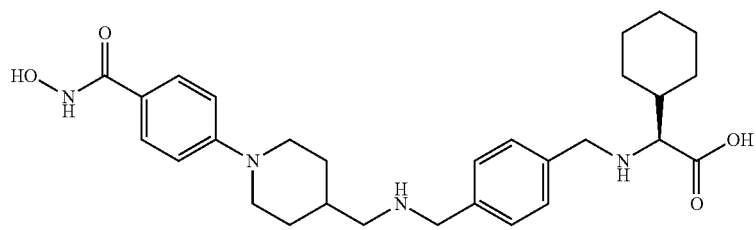

Compounds Prepared

FIG. 11

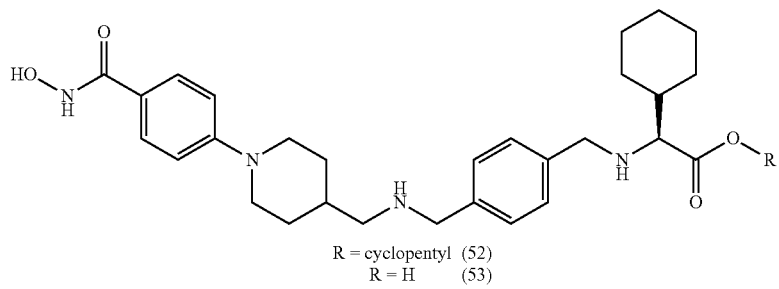

R = cyclopentyl (52)
R = H (53)

Stage 1—Reductive Amination

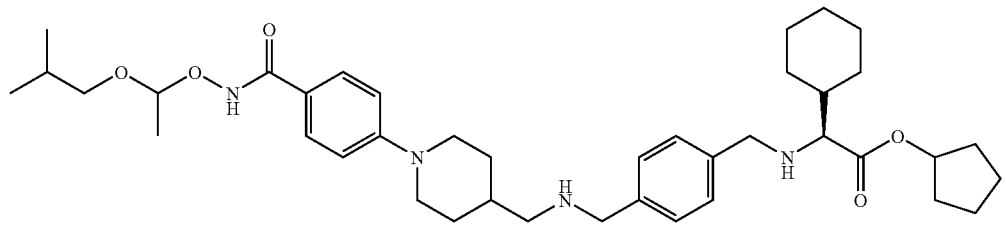 [SMILES: CC(C)COC(C)ONC(=O)c1ccc(N2CCC(CNCc3ccc(CN[C@H](C(=O)OC4CCCC4)C4CCCCC4)cc3)CC2)cc1]

4-(4-Formylpiperidin-1-yl)-N-(1-isobutoxyethoxy)benzamide (prepared as described in Example 9—210 mg, 0.603 mmol), was stirred with cyclopentyl (2S)-{[4-(aminomethyl)benzyl]amino}(cyclohexyl)acetate (prepared as described in Example 4—230 mg, 0.604 mmol) in 1,2-dichloroethane (20 mL). To this was added triethylamine (0.85 mL, 6.10 mmol) and sodium cyanoborohydride (540 mg, 8.59 mmol) and the mixture stirred at RT for 2 days. The mixture was added to water (50 mL) and extracted with DCM (2×50 mL). The organic phase was dried (MgSO$_4$), and concentrated in vacuo to yield a brown oil (408 mg, 92%). m/z=677 [M+H]$^+$.

Stage 2—Hydroxamate Deprotection to Yield Cyclopentyl (2S)-cyclohexyl[(4-{[({1-[4-(hydroxycarbamoyl)phenyl]piperidin-4-yl}methyl)amino]methyl}benzyl)amino]acetate (52)

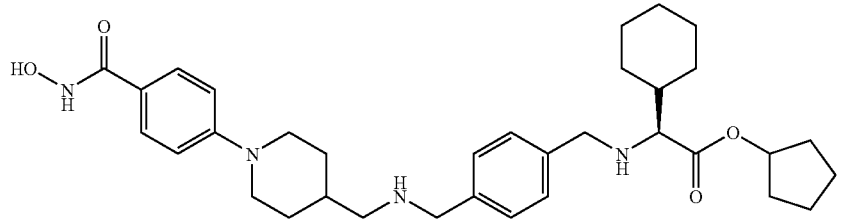 [SMILES: O=C(NO)c1ccc(N2CCC(CNCc3ccc(CN[C@H](C(=O)OC4CCCC4)C4CCCCC4)cc3)CC2)cc1]

Stage 1 product (226 mg, 334 μmol) was stirred in DCM (10 mL) and TFA (0.5 mL) at RT for 1 h. The product was purified by preparative HPLC to yield an off white solid (33.5 mg, 17%). LCMS purity 95%, m/z=577 [M+H]⁺. ¹H NMR (300 MHz, CD₃OD) δ: 7.64 (6H, m), 7.02 (2H, d, J=8.2 Hz), 5.31 (1H, t, J=5.3 Hz), 4.30 (4H, br s), 3.86 (3H, m), 3.01 (1H, s), 2.92 (2H, t, J=11.1 Hz), 2.05-1.68 (20H, m), 1.48-0.95 (8H, m).

Stage 3—Ester Hydrolysis

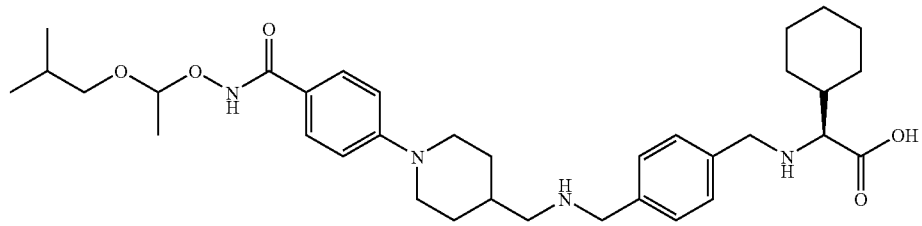 [SMILES: CC(C)COC(C)ONC(=O)c1ccc(N2CCC(CNCc3ccc(CN[C@H](C(=O)O)C4CCCCC4)cc3)CC2)cc1]

Stage 1 product (218 mg, 322 μmol) was stirred in THF (10 mL) with potassium trimethylsilanolate (418 mg, 3.26 mmol) at 50° C. for 4 days. The mixture was concentrated in vacuo and the residue used crude in the next stage.

Stage 4—Hydroxamate Deprotection to Yield {(2S)-2-cyclohexyl-2-[(4-{[({1-[4-(hydroxycarbamoyl)phenyl]piperidin-4-yl}methyl)amino]methyl}benzyl)amino]acetyl}oxy (53)

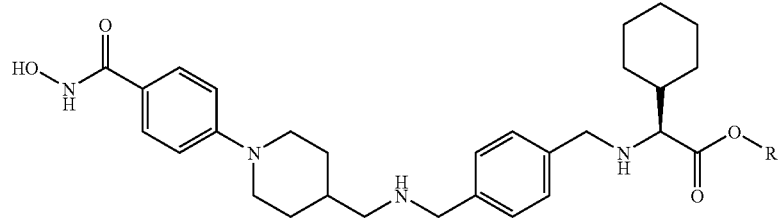

Stage 3 product was stirred in DCM (10 mL) with TFA (0.5 mL) at RT for 1 h. The mixture was concentrated in vacuo and the product purified by preparative HPLC to yield a white solid (28.0 mg, 17%). LCMS purity 95%, m/z=509 [M+H]⁺. ¹H NMR (300 MHz, CD₃OD) δ: 7.66 (6H, m), 7.02 (2H, d, J=8.6 Hz), 4.30 (4H, s), 3.89 (2H, d, J=12.2 Hz), 3.76 (1H, d, J=3.2 Hz), 3.01 (2H, d, J=6.4 Hz), 2.90 (2H, t, J=12.1 Hz), 2.03-1.68 (10H, m), 1.46-1.05 (8H, m).

Example 11

Scheme 15

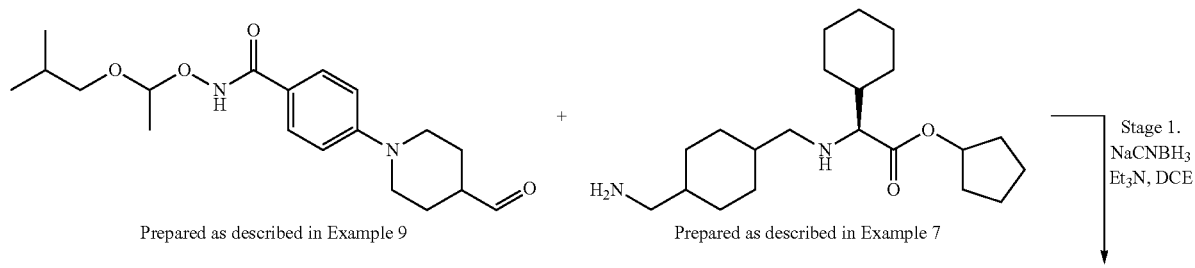

Prepared as described in Example 9     Prepared as described in Example 7

Stage 1. NaCNBH₃ Et₃N, DCE

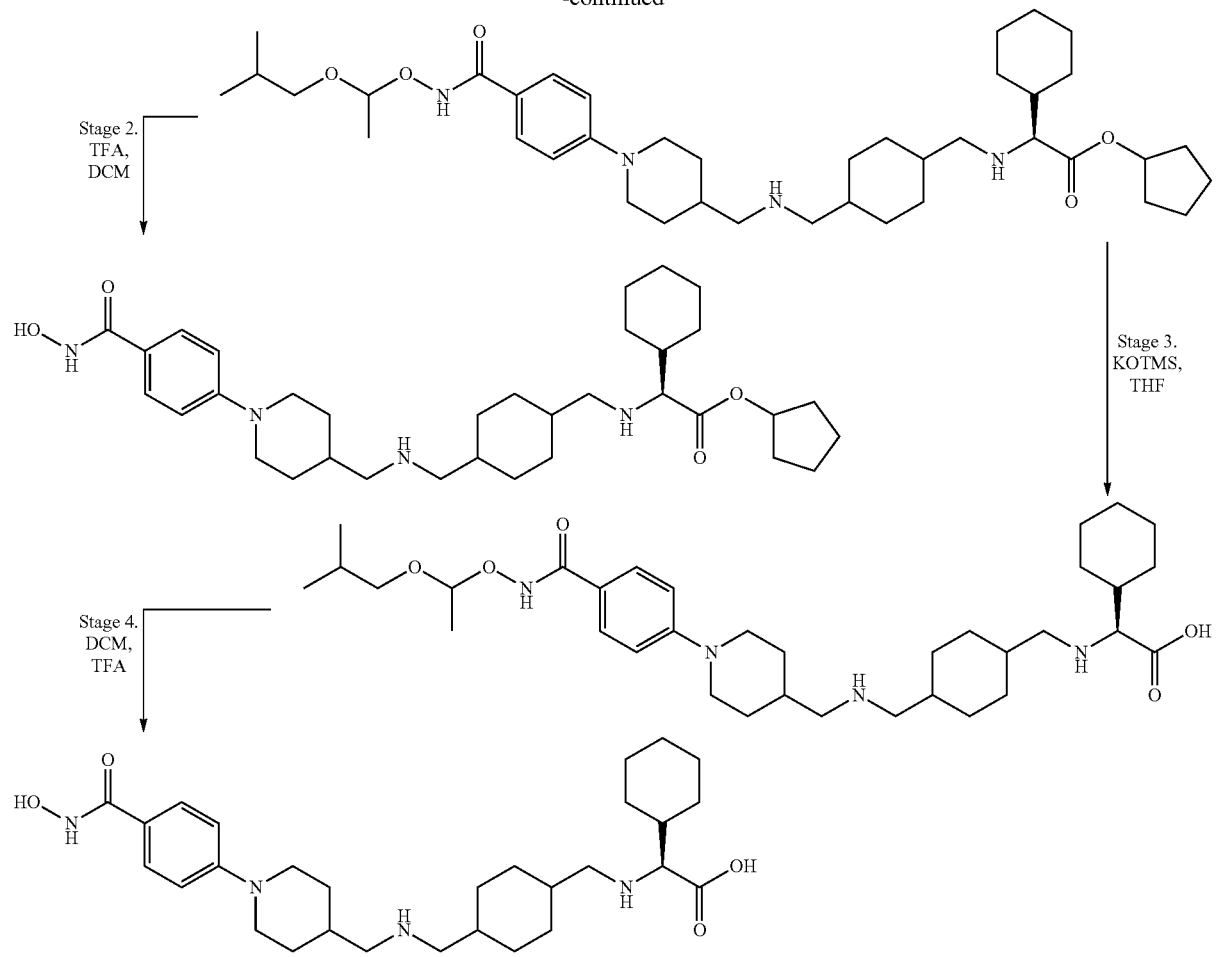
Compounds Prepared:
FIG. 12
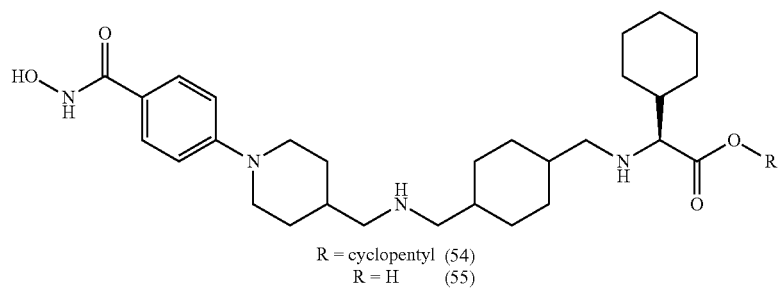
R = cyclopentyl (54)
R = H (55)
Stage 1—Reductive Amination
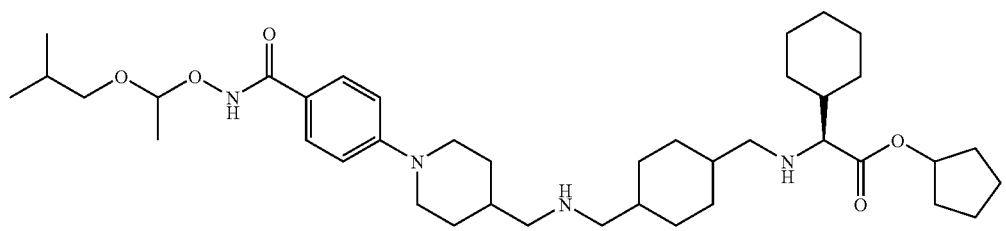 [SMILES: CC(C)COC(C)ONC(=O)c1ccc(N2CCC(CNCC3CCC(CN[C@H](C(=O)OC4CCCC4)C4CCCCC4)CC3)CC2)cc1]

4-(4-formylpiperidin-1-yl)-N-(1-isobutoxyethoxy)benzamide (prepared as described in Example 9—212 mg, 0.608 mmol), was stirred with cyclopentyl (2S)-({[4-(aminomethyl)cyclohexyl]methyl}amino)(cyclohexyl)acetate (prepared as described in Example 7—236 mg, 0.609 mmol) in 1,2-dichloroethane (20 mL). To this was added triethylamine (0.85 mL, 6.10 mmol) and sodium cyanoborohydride (555 mg, 8.83 mmol) and the mixture stirred at RT for 2 days. The mixture was then added to water (50 mL) and extracted with DCM (2×50 mL). The organic phase was dried (MgSO$_4$), and concentrated in vacuo to yield a brown oil (318 mg, 77%). m/z=683 [M+H]$^+$.

Stage 2—Hydroxamate Deprotection to Yield cyclopentyl (2S)-cyclohexyl{[(4-{[({1-[4-(hydroxycarbamoyl)phenyl]piperidin-4-yl}methyl)amino]methyl}cyclohexyl)methyl]amino}acetate (54)

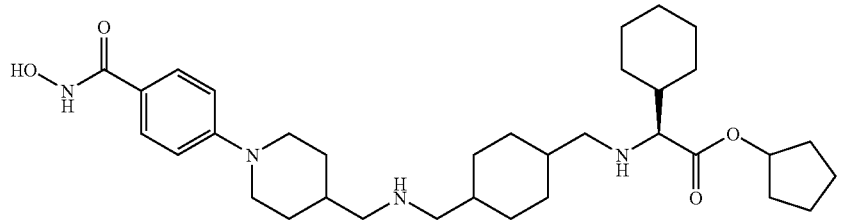 [SMILES: O=C(NO)c1ccc(N2CCC(CNCC3CCC(CN[C@H](C(=O)OC4CCCC4)C4CCCCC4)CC3)CC2)cc1]

Stage 1 product (257 mg, 376 μmol) was stirred in DCM (10 mL) and TFA (0.5 mL) at RT for 1 h. The product was purified by preparative HPLC to yield an off white solid (18.7 mg, 9%). LCMS purity 98%, m/z=583 [M+H]$^+$. $^1$H NMR (300 MHz, CD$_3$OD) δ: 7.68 (2H, d, J=8.5 Hz), 7.04 (2H, d, J=8.6 Hz), 5.36 (1H, m), 3.04-2.81 (8H, m), 2.06-1.64 (25H, m), 1.53-0.97 (12H, m).

Stage 3—Ester Hydrolysis

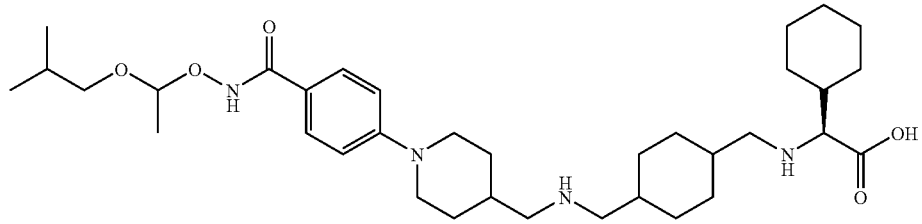 [SMILES: CC(C)COC(C)ONC(=O)c1ccc(N2CCC(CNCC3CCC(CN[C@H](C(=O)O)C4CCCCC4)CC3)CC2)cc1]

Stage 1 product (196 mg, 287 μmol) was stirred in THF (10 mL) with potassium trimethylsilanolate (399 mg, 3.11 mmol) at 50° C. for 4 days. The mixture was concentrated in vacuo and the residue used crude for the next stage.

Stage 4—Hydroxamate Deprotection to Yield (2S)-cyclohexyl{[(4-{[({1-[4-(hydroxycarbamoyl)phenyl]piperidin-4-yl}methyl)amino]methyl}cyclohexyl)methyl]amino}acetic acid (55)

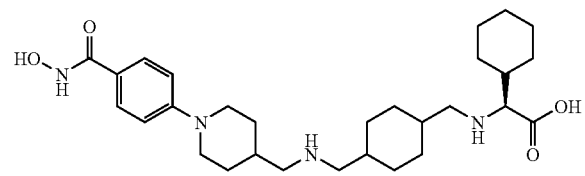 [SMILES: O=C(NO)c1ccc(N2CCC(CNCC3CCC(CN[C@H](C(=O)O)C4CCCCC4)CC3)CC2)cc1]

Stage 3 product was stirred in DCM (10 mL) with TFA (0.5 mL) at RT for 1 h. The mixture was concentrated in vacuo and the product purified by preparative HPLC to yield an off white solid (36.7 mg, 25%). LCMS purity 98%, m/z=515 [M+H]$^+$. $^1$H NMR (300 MHz, CD$_3$OD) δ: 7.68 (2H, d, J=8.7 Hz), 7.05 (2H, d, J=8.5 Hz), 3.89 (2H, d, J=12.6 Hz), 3.79 (1H, d, J=3.6 Hz), 3.03-2.82 (8H, m), 2.07-1.65 (16H, m), 1.54-1.04 (12H, m).

Broken Cell Carboxylesterase Assay

Any given compound of the present invention wherein R$_1$ is an ester group, may be tested to determine whether it meets the requirement that it be hydrolysed by intracellular esterases, by testing in the following assay.

Preparation of Cell Extract

U937 or HCT 116 tumour cells (~10$^9$) were washed in 4 volumes of Dulbeccos PBS (~1 liter) and pelleted at 525 g for 10 min at 4° C. This was repeated twice and the final cell pellet was resuspended in 35 ml of cold homogenising buffer (Trizma 10 mM, NaCl 130 mM, CaCl$_2$ 0.5 mM pH 7.0 at 25° C.). Homogenates were prepared by nitrogen cavitation (700 psi for 50 min at 4° C.). The homogenate was kept on ice and supplemented with a cocktail of inhibitors at final concentrations of:

Leupeptin 1 μM
Aprotinin 0.1 μM
E64 8 μM
Pepstatin 1.50 μM
Bestatin 162 μM
Chymostatin 33 μM After clarification of the cell homogenate by centrifugation at 525 g for 10 min, the resulting supernatant was used as a source of esterase activity and was stored at −80° C. until required.

Measurement of Ester Cleavage

Hydrolysis of esters to the corresponding carboxylic acids can be measured using the cell extract, prepared as above. To this effect cell extract (~30 μg/total assay volume of 0.5 ml) was incubated at 37° C. in a Tris-HCl 25 mM, 125 mM NaCl buffer, pH 7.5 at 25° C. At zero time the ester (substrate) was then added at a final concentration of 2.50M and the samples were incubated at 37° C. for the appropriate time (usually 0 or 80 min). Reactions were stopped by the addition of 3× volumes of acetonitrile. For zero time samples the acetonitrile was added prior to the ester compound. After centrifugation at 12000 g for 5 min, samples were analysed for the ester and its corresponding carboxylic acid at room temperature by LCMS (Sciex API 3000, HP1100 binary pump, CTC PAL). Chromatography was based on an AceCN (75*2.1 mm) column and a mobile phase of 5-95% acetonitrile in water/0.1% formic acid.

Measurement of Biological Activities

Histone Deacetylase Activity

The ability of compounds to inhibit histone deacetylase activities was measured using the commercially available HDAC fluorescent activity assay from Biomol. In brief, the Fluor de Lys™ substrate, a lysine with an epsilon-amino acetylation, is incubated with the source of histone deacetylase activity (HeLa nuclear extract) in the presence or absence of inhibitor. Deacetylation of the substrate sensitises the substrate to Fluor de Lys™ developer, which generates a fluorophore. Thus, incubation of the substrate with a source of HDAC activity results in an increase in signal that is diminished in the presence of an HDAC inhibitor.

Data are expressed as a percentage of the control, measured in the absence of inhibitor, with background signal being subtracted from all samples, as follows:

$$\% \text{ activity} = [(S^i - B)/(S^o - B)] \times 100$$

where $S^i$ is the signal in the presence of substrate, enzyme and inhibitor, $S^o$ is the signal in the presence of substrate, enzyme and the vehicle in which the inhibitor is dissolved, and B is the background signal measured in the absence of enzyme.

$IC_{50}$ values were determined by non-linear regression analysis, after fitting the results of eight data points to the equation for sigmoidal dose response with variable slope (% activity against log concentration of Compound), using Graphpad Prism software.

Histone deacetylase activity from crude nuclear extract derived from HeLa cells was used for screening. The preparation, purchased from 4C (Seneffe, Belgium), was prepared from HeLa cells harvested whilst in exponential growth phase. The nuclear extract was prepared according to the methodology described by J. D. Dignam, Nucl. Acid. Res., 1983, 11, 1475-1489, snap frozen in liquid nitrogen and stored at −80° C. The final buffer composition was 20 mM Hepes, 100 mM KCl, 0.2 mM EDTA, 0.5 mM DTT, 0.2 mM PMSF and 20% (v/v) glycerol.

$IC_{50}$ results were allocated to one of 3 ranges as follows:
Range A: $IC_{50} < 100$ nM,
Range B: $IC_{50}$ from 101 nM to 1000 nM;
and Range C: $IC_{50} > 1001$ nM.

U937 and HUT Cell Inhibition Assay

Cancer cell lines (U937 and HUT) growing in log phase were harvested and seeded at 1000-2000 cells/well (100 µl final volume) into 96-well tissue culture plates. Following 24 h of growth cells were treated with Compound. Plates were then re-incubated for a further 72-96 h before a WST-1 cell viability assay was conducted according to the suppliers (Roche Applied Science) instructions.

Data were expressed as a percentage inhibition of the control, measured in the absence of inhibitor, as follows:—

$$\% \text{ inhibition} = 100 - [(S^i/S^o) \times 100]$$

where $S^i$ is the signal in the presence of inhibitor and $S^o$ is the signal in the presence of DMSO.

Dose response curves were generated from 8 concentrations (top final concentration 10 µM, with 3-fold dilutions), using 6 replicates.

$IC_{50}$ values were determined by non-linear regression analysis, after fitting the results to the equation for sigmoidal dose response with variable slope (% activity against log concentration of Compound), using Graphpad Prism software.

$IC_{50}$ results were allocated to one of 3 ranges as follows:
Range A: $IC_{50} < 330$ nM,
Range B: $IC_{50}$ from 331 nM to 3300 nM;
Range C: $IC_{50} > 3301$ nM;
and n/d: not determined.

HeLa Cell Inhibition Assay

HeLa cells growing in log phase were harvested and seeded at 1000 cells/well (200 µl final volume) into 96-well tissue culture plates. Following 24 h of cell growth cells were treated with Compounds (final concentration of 20 µM). Plates were then re-incubated for a further 72 h before a sulphorhodamine B (SRB) cell viability assay was conducted according to the methodology described by Skehan et al, J. Natl. Canc. Inst., 1990, 82, 1107-1112.

Data were expressed as a percentage inhibition of the control, measured in the absence of inhibitor, as follows:—

$$\% \text{ inhibition} = 100 - [(S^i/S^o) \times 100]$$

where $S^i$ is the signal in the presence of inhibitor and $S^o$ is the signal in the presence of DMSO.

$IC_{50}$ values were determined by non-linear regression analysis, after fitting the results of eight data points to the equation for sigmoidal dose response with variable slope (% activity against log concentration of Compound), using Graphpad Prism software.

$IC_{50}$ results were allocated to one of 3 ranges as follows:
Range A: $IC_{50} < 330$ nM,
Range B: $IC_{50}$ from 331 nM to 3300 nM;
Range C: $IC_{50} > 3301$ nM;
and n/d: not determined.

Results Table

| Example No. | HDAC activity | U937 activity | HUT activity | HeLa activity |
|---|---|---|---|---|
| 1 | B | A | B | C |
| 2 | B | n/d | n/d | n/d |
| 3 | B | B | C | C |
| 4 | C | n/d | n/d | n/d |
| 5 | B | B | B | C |
| 6 | C | n/d | n/d | n/d |
| 7 | B | A | B | C |
| 8 | B | n/d | n/d | n/d |
| 9 | B | B | B | C |
| 10 | A | B | B | B |
| 11 | B | n/d | n/d | n/d |
| 12 | A | A | B | B |
| 13 | B | n/d | n/d | n/d |
| 14 | A | B | B | B |
| 15 | B | n/d | n/d | n/d |
| 16 | A | A | A | B |
| 17 | B | n/d | n/d | n/d |
| 18 | A | A | B | B |
| 19 | B | n/d | n/d | n/d |
| 20 | A | A | B | B |
| 21 | A | n/d | n/d | n/d |
| 22 | A | A | A | B |
| 23 | B | n/d | n/d | n/d |
| 24 | A | A | A | B |
| 25 | B | n/d | n/d | n/d |
| 26 | B | B | B | C |
| 27 | A | A | A | B |
| 28 | B | n/d | n/d | n/d |
| 29 | A | A | B | B |
| 30 | A | n/d | n/d | n/d |
| 31 | B | A | B | B |

| Results Table | | | | |
|---|---|---|---|---|
| Example No. | HDAC activity | U937 activity | HUT activity | HeLa activity |
| 32 | B | n/d | n/d | n/d |
| 33 | A | A | A | B |
| 34 | A | n/d | n/d | n/d |
| 35 | A | B | B | B |
| 36 | A | A | A | A |
| 37 | A | n/d | n/d | n/d |
| 38 | A | A | B | A |
| 39 | A | n/d | n/d | n/d |
| 40 | A | A | A | B |
| 41 | A | n/d | n/d | n/d |
| 42 | A | A | A | A |
| 43 | A | n/d | n/d | n/d |
| 44 | A | A | A | B |
| 45 | A | n/d | n/d | n/d |
| 46 | B | B | B | n/d |
| 47 | A | n/d | n/d | n/d |
| 48 | C | B | C | n/d |
| 49 | C | n/d | n/d | n/d |
| 50 | C | C | C | n/d |
| 51 | C | n/d | n/d | n/d |
| 52 | C | B | B | n/d |
| 53 | C | n/d | n/d | n/d |
| 54 | C | B | B | n/d |
| 55 | C | n/d | n/d | n/d |

The invention claimed is:

1. A compound of formula (I), or a salt, or N-oxide thereof:

(I)

wherein n is 0 or 1;

Q, V and W independently represent —N= or —C=;

B is a divalent radical selected from (B1), (B2), (B3), (B4), (B5) and (B6):

(B1)

(B2)

(B3)

(B4)

(B5)

(B6)

wherein the bond marked * is linked to the ring containing Q, V and W;

A is an optionally substituted mono-, bi- or tri-cyclic carbocyclic or heterocyclic ring system;

-[Linker]- represents a bond, or a divalent linker radical;

$Z^1$ is (a) a radical of formula $R_1R_2CHNH-Y-L^1-X^1-(CH_2)_n-$ or (b) a radical of formula $R-L^1-Y^1-(CH_2)_z-$, wherein:

R is a radical of formula (X) or (Y)

(X)

(Y)

$R_1$ is a carboxylic acid group (—COOH), or an ester group which is hydrolysable by one or more intracellular esterase enzymes to a carboxylic acid group;

$R_6$ is hydrogen; or optionally substituted $C_1$-$C_6$ alkyl, $C_3$-$C_7$ cycloalkyl, aryl or heteroaryl or —(C=O)$R_3$, —(C=O)O$R_3$, or —(C=O)N$R_3$ wherein $R_3$ is hydrogen or optionally substituted ($C_1$-$C_6$)alkyl;

$R_2$ is the side chain of a natural or non-natural alpha amino acid;

Y is a bond, —C(=O)—, —S(=O)$_2$—, —C(=O)O—, —C(=O)N$R_3$—, —C(=S)—N$R_3$, —C(=NH)—N$R_3$ or —S(=O)$_2$N$R_3$— wherein $R_3$ is hydrogen or optionally substituted $C_1$-$C_6$ alkyl;

$Y^1$ is a bond, —(C=O)—, —S(O$_2$)—, —C(=O)O—, —OC(=O)—, —N$R_3$(C=O)—, —S(O$_2$)N$R_3$—, —N$R_3$S(O$_2$)—, or —N$R_3$(C=O)N$R_4$—, wherein $R_3$ and $R_4$ are independently hydrogen or optionally substituted ($C_1$-$C_6$)alkyl, $L^1$ is a divalent radical of formula -(Alk$^1$)$_m$(Q)$_n$(Alk$^2$)$_p$- wherein m, n and p are independently 0 or 1, Q is (i) an optionally substituted divalent mono- or bicyclic carbocyclic or heterocyclic radical having 5-13 ring members, or (ii), in the case where p is 0, a divalent radical of formula -Q'-X$^2$— wherein X$^2$ is —O—, —S— or NR$^A$— wherein R$^A$ is hydrogen or optionally substituted $C_1$-$C_3$ alkyl, and Q' is an optionally substituted divalent mono- or bicyclic carbocyclic or heterocyclic radical having 5-13 ring members, Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^A$—) link wherein R$^A$ is hydrogen or optionally substituted $C_1$-$C_3$ alkyl;

$X^1$ is a bond, —C(=O)—; or —S(=O)$_2$—; —NR$_4$C(=O)—, —C(=O)NR$_4$—, —NR$_4$C(=O)—NR$_5$—, —NR$_4$S(=O)$_2$—, or —S(=O)$_2$NR$_4$— wherein R$_4$ and R$_5$ are independently hydrogen or optionally substituted C$_1$-C$_6$ alkyl; and
z is 0 or 1.
2. A compound as claimed in claim 1 wherein Q is —C= and V and W are each —N=.
3. A compound as claimed in claim 1 wherein A is one of the following ring systems, optionally substituted:
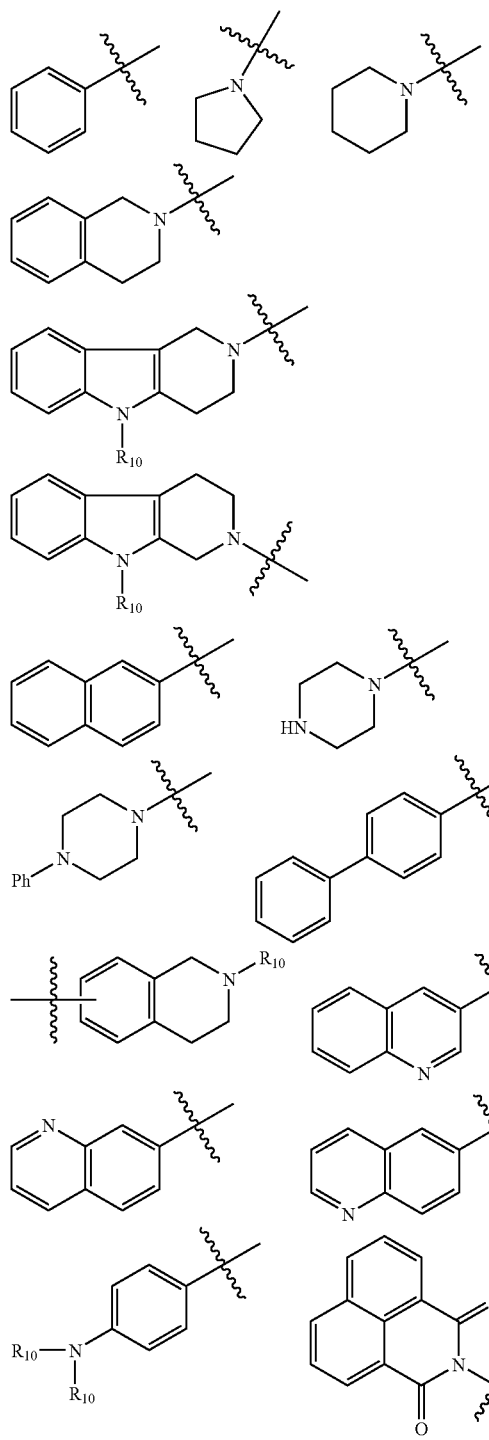
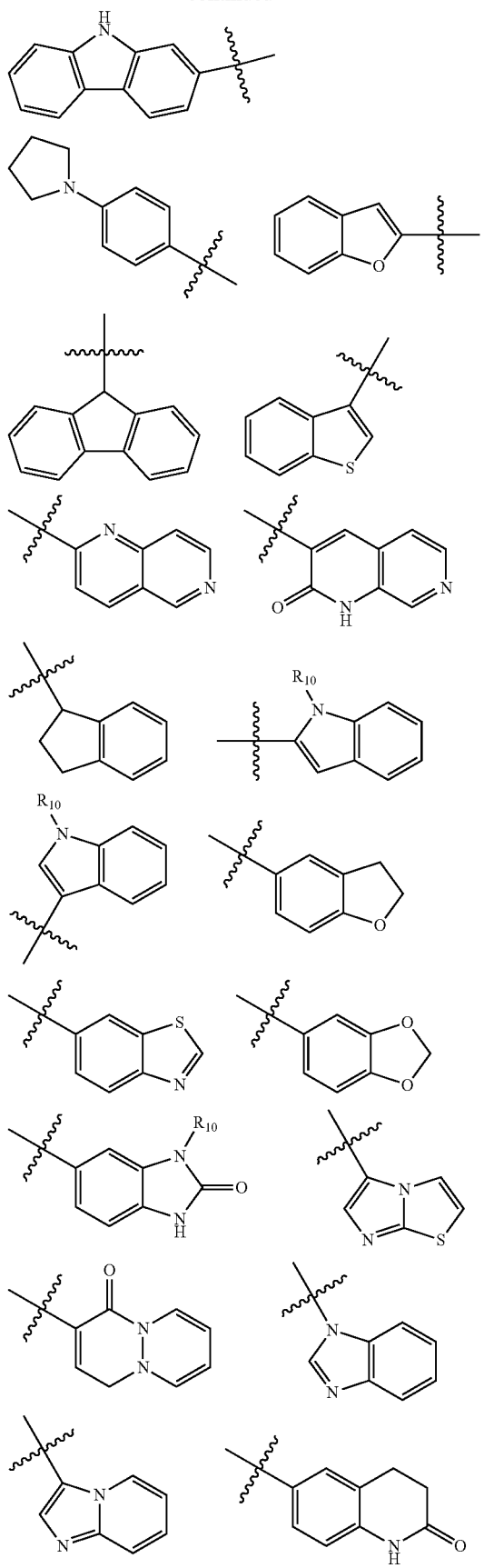

-continued

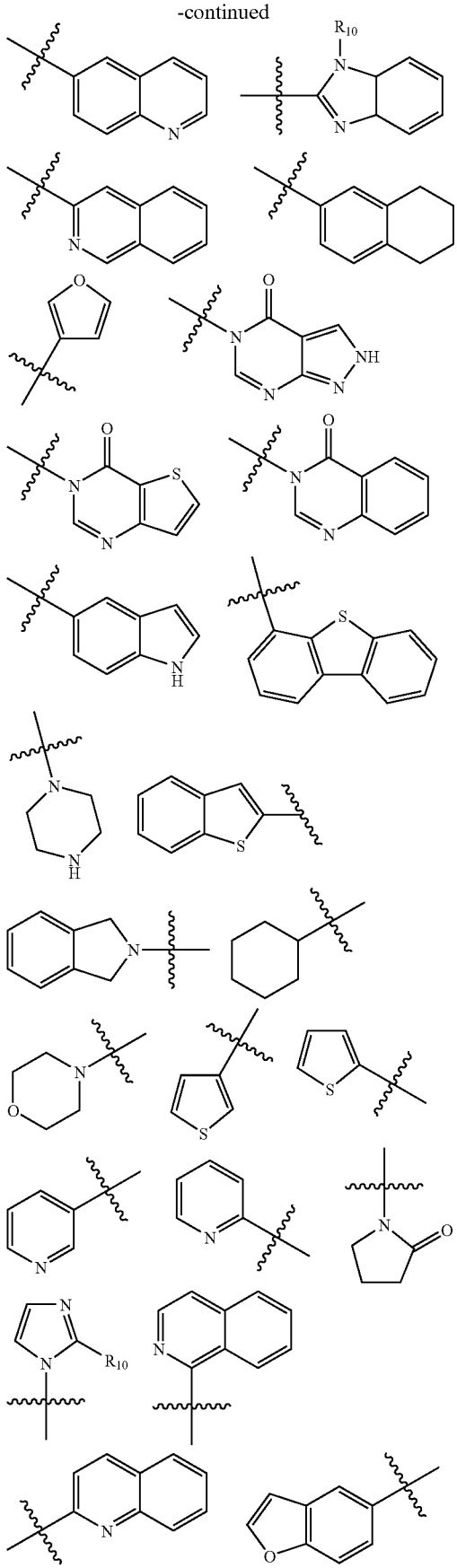

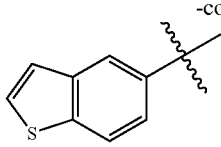

wherein $R_{10}$ is hydrogen or $C_1$-$C_6$ alkyl, the bond intersected by the wavy line connects to the -[Linker]- radical, and R is attached to an available ring atom.

4. A compound as claimed in claim 1 wherein ring A is selected from optionally substituted phenyl, cyclohexyl, naphthyl, quinolin-2-yl, and 1,3-dihydro-isoindol-2-yl.

5. A compound as claimed in claim 4 wherein optional substituents in ring A are selected from fluoro and chloro.

6. A compound as claimed in claim 1 wherein -[Linker]- is selected from:
   (i) a bond;
   (ii) —O—, —S—, —C(═O)—, —S(═O)$_2$—, —NR$^C$—, —C(═O)NR$^C$—, —S(═O)$_2$NR$^C$—, —NR$^C$S(═O)$_2$—, —NR$^C$(CH$_2$)$_m$—, —NR$^C$C(═O)(CH$_2$)$_m$—, —NR$^C$S(═O)$_2$(CH$_2$)$_m$, —NR$^D$C(═O)NR$^C$—, or —NR$^C$C(═O)(CH$_2$)$_m$Ar—, or —NR$^C$S(═O)$_2$(CH$_2$)$_m$Ar— wherein R$^C$ and R$^D$ are independently hydrogen, $C_1$-$C_4$ alkyl or a nitrogen substituent, m is 1, 2 or 3, and Ar is a divalent phenyl radical or a divalent mono-, or bi-cyclic heteroaryl radical having 5 to 13 ring members; and
   (iii) an optionally substituted, straight or branched, $C_1$-$C_6$ alkylene, $C_2$-$C_6$ alkenylene or $C_2$-$C_6$ alkynylene radical which may optionally contain or terminate in an ether (—O—), thioether (—S—) or amino (—NR$^A$—) link wherein R$^A$ is hydrogen, $C_1$-$C_3$ alkyl or a nitrogen substituent.

7. A compound as claimed in claim 6 wherein —Ar— is present in -[Linker]- and is a divalent radical selected from the following:

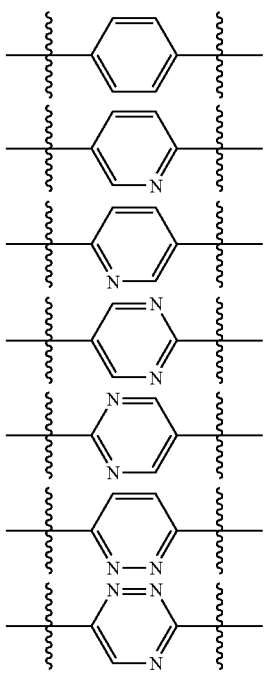

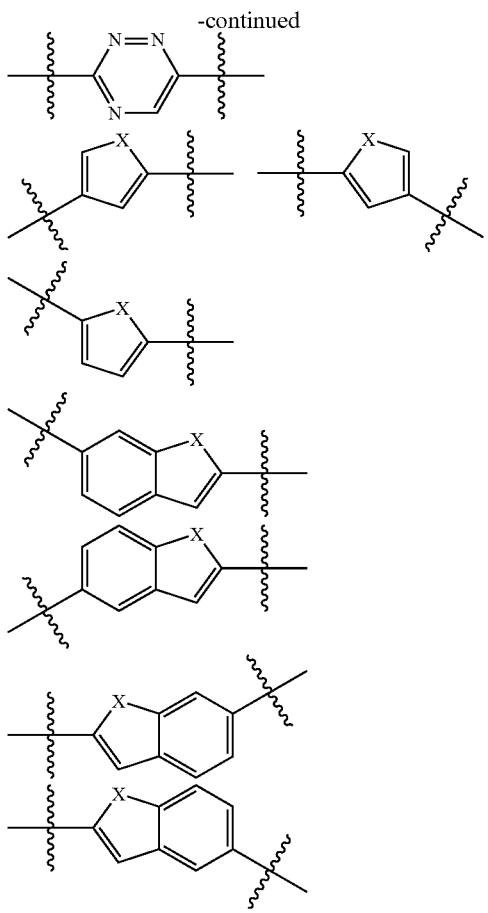

wherein X is O, S or NH.

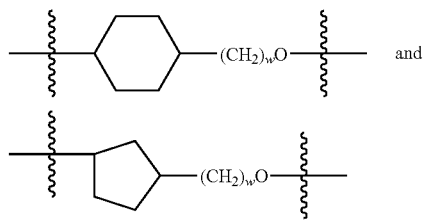

wherein v is 1, 2, 3 or 4 and w is 1, 2 or 3.

8. A compound as claimed in claim 6 wherein —Ar— is present in -[Linker]- and is a divalent phenylene radical.

9. A compound as claimed in claim 1 wherein -[Linker]- is a bond when n is 0.

10. A compound as claimed in claim 1 wherein z is 0.

11. A compound as claimed in claim 1 wherein Y is —S(=O)$_2$—, —C(=S)—NR$_3$, —C(=NH)—NR$_3$ or —S(=O)$_2$NR$_3$— wherein R$_3$ is hydrogen or C$_1$-C$_6$ alkyl.

12. A compound as claimed in claim 1 wherein Y is a bond.

13. A compound as claimed in claim 1 wherein, in the radical L$^1$, Alk$^1$ and Alk$^2$, when present, are selected from —CH$_2$—, —CH$_2$CH$_2$—, —CH$_2$CH$_2$CH$_2$—, and divalent cyclopropyl, cyclopentyl and cyclohexyl radicals.

14. A compound as claimed in claim 1 wherein, in the radical L$^1$, Q$^1$ is a divalent phenyl radical or a mono-, or bi-cyclic heteroaryl radical having 5 to 13 ring members.

15. A compound as claimed in claim 12 wherein Q$^1$ is 1,4-phenylene.

16. A compound as claimed in claim 1 wherein, in the radical L$^1$, p and r are 0.

17. A compound as claimed in claim 1 wherein, in the radical L$^1$, q and r are 0 and p is 1.

18. A compound as claimed in claim 1 wherein, in the radical L$^1$, p, q and r are all 0.

19. A compound as claimed in claim 1 wherein Z$^1$ is a radical of formula R$_1$R$_2$CHNH—Y-L$^1$-X$^1$—(CH$_2$)$_z$— wherein the radical —Y-L$^1$-X$^1$-[CH$_2$]$_z$— is selected from —C(=O)—, —C(=O)NH—, —(CH$_2$)$_v$—, —(CH$_2$)$_v$O—, —C(=O)—(CH$_2$)$_v$—, —C(=O)—(CH$_2$)$_v$O—, —C(=O)—NH—(CH$_2$)$_w$—, —C(=O)—NH—(CH$_2$)$_w$O—

20. A compound as claimed in claim 1 wherein Z$^1$ is a radical of formula R$_1$R$_2$CHNH—Y-L$^1$-X$^1$—(CH$_2$)$_z$— wherein the radical —Y-L$^1$-X$^1$—[CH$_2$]$_z$— is —CH$_2$—, —CH$_2$O—, —C(=O)—CH$_2$—, —C(=O)—CH$_2$O—, —C(=O)—NH—CH$_2$—, or —C(=O)—NH—CH$_2$O—.

21. A compound as claimed in claim 1 wherein R$_1$ is an ester group of formula —(C=O)OR$_9$ wherein R$_9$ is R$_7$R$_8$CH— wherein (i) R$_7$ is hydrogen or optionally substituted (C$_1$-C$_3$)alkyl-(Z$^1$)$_a$-[(C$_1$-C$_3$)alkyl]$_b$— or (C$_2$-C$_3$)alkenyl-(Z$^1$)$_a$-[(C$_1$-C$_3$)alkyl]$_b$— wherein a and b are independently 0 or 1 and Z$^1$ is —O—, —S—, or —NR$_{10}$— wherein R$_{10}$ is hydrogen or C$_1$-C$_3$ alkyl, and R$_8$ is hydrogen or (C$_1$-C$_3$) alkyl-;

(ii) R$_7$ is hydrogen or optionally substituted R$_{10}$R$_{11}$N—(C$_1$-C$_3$)alkyl- wherein R$_{10}$ is hydrogen or C$_1$-C$_3$ alkyl and R$_{11}$ is hydrogen or C$_1$-C$_3$ alkyl; or R$_{10}$ and R$_{11}$ together with the nitrogen to which they are attached form an optionally substituted monocyclic heterocyclic ring of 5- or 6-ring atoms or bicyclic heterocyclic ring system of 8 to 10 ring atoms, and R$_8$ is hydrogen or (C$_1$-C$_3$)alkyl-; or (iii) R$_7$ and R$_8$ taken together with the carbon to which they are attached form an optionally substituted monocyclic carbocyclic ring of from 3 to 7 ring atoms or bicyclic carbocyclic ring system of 8 to 10 ring atoms.

22. A compound as claimed in claim 21 wherein R$_9$ is methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl, methoxyethyl, indanyl, norbornyl, dimethylaminoethyl, or morpholinoethyl.

23. A compound as claimed in claim 21 wherein R$_9$ is cyclopentyl.

24. A compound as claimed in claim 1 wherein Z$^1$ is a radical of formula R$_1$R$_2$CHNH—Y-L$^1$-X$^1$—(CH$_2$)$_z$— and wherein R$_2$ is cyclohexylmethyl, pyridin-3-ylmethyl, sec-butyl, tert-butyl, 1-benzylthio-1-methylethyl, 1-methylthio-1-methylethyl, 1-mercapto-1-methylethyl, or phenylethyl.

25. A compound as claimed in claim 1 wherein Z$^1$ is a radical of formula R$_1$R$_2$CHNH—Y-L$^1$-X$^1$—(CH$_2$)$_z$— and wherein R$_2$ is hydrogen.

26. A compound as claimed in claim 1 wherein Z$^1$ is a radical of formula R$_1$R$_2$CHNH—Y-L$^1$-X$^1$—(CH$_2$)$_z$— and wherein R$_2$ is phenyl, benzyl, iso-butyl, cyclohexyl or t-butoxymethyl.

27. A pharmaceutical composition comprising a compound as claimed in claim 1, together with a pharmaceutically acceptable carrier.

28. A compound as claimed in claim 1 wherein n is 0 or 1;

Q, V and W independently represent —N= or —C=;

B is a divalent radical selected from (B1), (B2), (B3), (B4), (B5) and (B6):

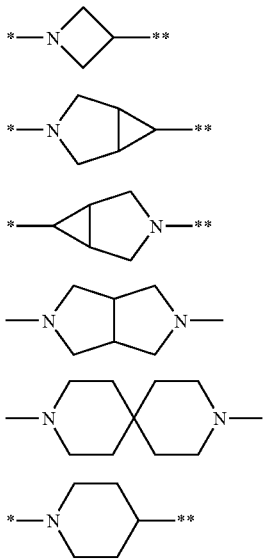

wherein the bond marked * is linked to the ring containing Q, V and W;

A is an optionally substituted mono-, bi- or tri-cyclic carbocyclic or heterocyclic ring system;

-[Linker]- is selected from:
  (i) a bond;
  (ii) —O—, —S—, —C(=O)—, —S(=O)$_2$—, —NR$^C$—, —C(=O)NR$^C$—, —S(=O)$_2$NR$^C$—, —NR$^C$S(=O)$_2$—, —NR$^C$(CH$_2$)$_m$—, —NR$^C$C(=O)(CH$_2$)$_m$—, —NR$^C$S(=O)$_2$(CH$_2$)$_m$—, —NR$^D$C(=O)NR$^C$—, or —NR$^C$C(=O)(CH$_2$)$_m$Ar—, or —NR$^C$S(=O)$_2$(CH$_2$)$_m$Ar— wherein R$^C$ and R$^D$ are independently hydrogen, C$_1$-C$_4$ alkyl or a nitrogen substituent, m is 1, 2 or 3, and Ar is a divalent phenyl radical or a divalent mono-, or bi-cyclic heteroaryl radical having 5 to 13 ring members; and
  (iii) an optionally substituted, straight or branched, C$_1$-C$_6$ alkylene, C$_2$-C$_6$ alkenylene or C$_2$-C$_6$ alkynylene radical which may optionally contain or terminate in an ether (—O—), thioether (—S—) or amino (—NR$^A$—) link wherein R$^A$ is hydrogen, C$_1$-C$_3$ alkyl or a nitrogen substituent;

Z$^1$ is (a) a radical of formula R$_1$R$_2$CHNH—Y-L$^1$-X$^1$—(CH$_2$)$_n$— or (b) a radical of formula R-L$^1$-Y$^1$—(CH$_2$)$_z$—, wherein:

R is a radical of formula (X) or (Y)

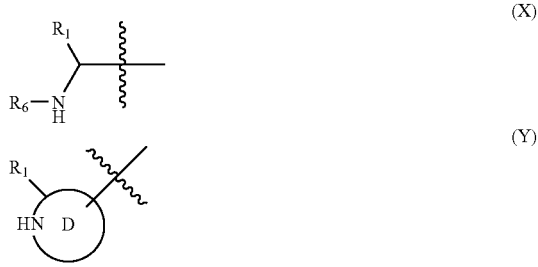

R$_1$ is a carboxylic acid group (—COOH), or an ester group which is hydrolysable by one or more intracellular esterase enzymes to a carboxylic acid group;

R$_6$ is hydrogen; or optionally substituted C$_1$-C$_6$ alkyl, C$_3$-C$_7$ cycloalkyl, aryl or heteroaryl or —(C=O)R$_3$, —(C=O)OR$_3$, or —(C=O)NR$_3$ wherein R$_3$ is hydrogen or optionally substituted (C$_1$-C$_6$)alkyl.

R$_2$ is the side chain of a natural or non-natural alpha amino acid;

Y is a bond, —C(=O)—, —S(=O)$_2$—, —C(=O)O—, —C(=O)NR$_3$—, —C(=S)—NR$_3$, —C(=NH)—NR$_3$ or —S(=O)$_2$NR$_3$— wherein R$_3$ is hydrogen or optionally substituted C$_1$-C$_6$ alkyl;

Y' is a bond, —(C=O)—, —S(O$_2$)—, —C(=O)O—, —OC(=O)—, —NR$_3$(C=O)—, —S(O$_2$)NR$_3$—, —NR$_3$S(O$_2$)—, or —NR$_3$(C=O)NR$_4$—, wherein R$_3$ and R$_4$ are independently hydrogen or optionally substituted (C$_1$-C$_6$)alkyl, L$^1$ is a divalent radical of formula -(Alk$^1$)$_m$(Q)$_n$(Alk$^2$)$_p$— wherein
  m, n and p are independently 0 or 1,
  Q is (i) an optionally substituted divalent mono- or bicyclic carbocyclic or heterocyclic radical having 5-13 ring members, or (ii), in the case where p is 0, a divalent radical of formula -Q$^1$-X$^2$—wherein X$^2$ is —O—, —S— or NR$^A$— wherein R$^A$ is hydrogen or optionally substituted C$_1$-C$_3$ alkyl, and Q' is an optionally substituted divalent mono- or bicyclic carbocyclic or heterocyclic radical having 5-13 ring members,
  Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl;

X$^1$ is a bond, —C(=O)—; or —S(=O)$_2$—; —NR$_4$C(=O)—, —C(=O)NR$_4$—, —NR$_4$C(=O)—NR$_5$—, —NR$_4$S(=O)$_2$—, or —S(=O)$_2$NR$_4$— wherein R$_4$ and R$_5$ are independently hydrogen or optionally substituted C$_1$-C$_6$ alkyl; and z is 0 or 1.

* * * * *